(12) United States Patent
Grimes et al.

(10) Patent No.: US 10,988,508 B2
(45) Date of Patent: Apr. 27, 2021

(54) SYNTHETIC N-ACETYL-MURAMIC ACID DERIVATIVES AND USES THEREOF

(71) Applicants: Catherine Leimkuhler Grimes, Newark, DE (US); James E. Melnyk, Newark, DE (US); Kristen E. Demeester, Newark, DE (US); Hai Liang, Newark, DE (US)

(72) Inventors: Catherine Leimkuhler Grimes, Newark, DE (US); James E. Melnyk, Newark, DE (US); Kristen E. Demeester, Newark, DE (US); Hai Liang, Newark, DE (US)

(73) Assignee: University of Delaware, Newark, DE (US)

( * ) Notice: Subject to any disclaimer, the term of this patent is extended or adjusted under 35 U.S.C. 154(b) by 352 days.

(21) Appl. No.: 15/568,559

(22) PCT Filed: Apr. 22, 2016

(86) PCT No.: PCT/US2016/029026
§ 371 (c)(1),
(2) Date: Oct. 23, 2017

(87) PCT Pub. No.: WO2016/172615
PCT Pub. Date: Oct. 27, 2016

(65) Prior Publication Data
US 2018/0298061 A1    Oct. 18, 2018

Related U.S. Application Data

(60) Provisional application No. 62/152,160, filed on Apr. 24, 2015.

(51) Int. Cl.
| | |
|---|---|
| *C07K 9/00* | (2006.01) |
| *C07H 15/04* | (2006.01) |
| *C07H 15/12* | (2006.01) |
| *C12N 1/20* | (2006.01) |
| *A61K 38/00* | (2006.01) |
| *A61K 39/02* | (2006.01) |
| *A61K 39/00* | (2006.01) |
| *C07H 11/04* | (2006.01) |
| *C07H 5/06* | (2006.01) |

(52) U.S. Cl.
CPC .............. *C07K 9/005* (2013.01); *C07H 5/06* (2013.01); *C07H 11/04* (2013.01); *C07H 15/04* (2013.01); *C07H 15/12* (2013.01); *C12N 1/20* (2013.01); *A61K 38/00* (2013.01); *A61K 39/02* (2013.01); *A61K 2039/52* (2013.01); *Y02A 50/30* (2018.01)

(58) Field of Classification Search
CPC .......... C07K 9/005; C07K 9/00; C07H 15/12; C07H 5/06; C07H 15/04; C07H 15/06; C07H 11/04
See application file for complete search history.

(56) References Cited

U.S. PATENT DOCUMENTS

| 4,082,736 A * | 4/1978 | Jones ..................... C07K 9/005 536/53 |
| 2004/0028702 A1 * | 2/2004 | Maletic ................ A61K 31/739 424/234.1 |

FOREIGN PATENT DOCUMENTS

WO    WO 2014065661 A1 *   5/2014

OTHER PUBLICATIONS

Kim, Sung J. et al., Biochimica et Biophysica Acta, "Peptidoglycan architecture of Gram-positive bacteria by solid-state NMR", published online Jun. 2014, vol. 1848, pp. 350-362 (Year: 2014).*
Xing, Shuo et al., Organic & Biomolecular Chemistry, "A robust synthesis of N-glycolyl muramyl dipeptide via azidonitration/reduction", published online Nov. 2014, vol. 13, pp. 1515-1520 (Year: 2014).*
International Preliminary Report for International Application No. PCT/US2016/029026 dated Nov. 2, 2017.
Boneca, Current Opinion in Microbiology, 8:46-53 (2005).
Chopra et al., Microbiology, 144:2673-78 (1998).
Hiebert et al., J. Med. Chem., 26:1729-32 (1983).
PCT/US2016/029026 International Search Report issued by Lee W. Young, dated Aug. 26, 2016.
Raymond et al., Journal Biological Chemistry, 280(1):326-33 (2005).
Renner-Schneck et al., Journal Biological Chemistry, 290(17):10804-13 (2015).

* cited by examiner

*Primary Examiner* — Bahar Craigo
(74) *Attorney, Agent, or Firm* — RatnerPrestia

(57) ABSTRACT

The present invention provides N-acetyl-muramic acid (NAM) derivatives having Formula I, wherein Xa is selected from the group consisting of X1-X59, Ya is selected from the group consisting of H, monophosphate, uridine diphosphate and ethyl azide linker prepared from 2-azido-ethanol, and Za is selected from the group consisting of OH, an ethylene diamine coupled fluorophore, a peptide and a peptide with an ethylene diamine coupled fluorophore, wherein the peptide is selected from the group consisting of a monopeptide, a dipeptide, a tripeptide and a pentapeptide. Also provided are methods for synthesizing NAM derivatives and methods for modulating Nod2 in cells, modifying bacterial cell wall or modulating innate immune response by a subject to bacterial cells upon exposure to NAM derivatives.

15 Claims, 8 Drawing Sheets

SYNTHETIC N-ACETYL-MURAMIC ACID DERIVATIVES AND USES THEREOF

CROSS-REFERENCE TO RELATED APPLICATION

This application is a U.S. national phase application of International Application No. PCT/US2016/029026, filed Apr. 22, 2016, claiming the benefit of U.S. Provisional Application No. 62/152,160, filed Apr. 24, 2015, the contents of each of which are incorporated herein by reference in their entireties for all purposes.

REFERENCE TO U.S. GOVERNMENT SUPPORT

This work is supported by grants from the U.S. National Institutes of Health (NIH) (NIH Grant #1P20GM104316-01A1 and 5 P30 GM110758-02). The United States has certain rights in the invention.

FIELD OF THE INVENTION

The invention relates generally to synthesis of unnatural N-acetyl-muramic acid (NAM) derivatives and their uses.

BACKGROUND OF THE INVENTION

The innate immune system must recognize and destroy pathogenic bacteria while maintaining the proper balance of the trillion commensal bacteria. One method by which the innate immune system detects bacteria is via the peptidoglycan, a strong polymer of carbohydrates and peptides which provides protection to the vulnerable bacterial cell. Peptidoglycan, is specifically constructed from peptides and two monosaccharide units; while the peptides vary, N-acetyl-glucosamine (NAG) and N-acetyl-muramic acid (NAM), remain constant throughout all bacteria.

The unique structures and biochemical machinery of the bacterial cell wall offer selective targets in antibiotic design. The mammalian innate immune system has evolved to sense and respond to fragments of this polymer. However, there are deleterious consequences such as antibiotic resistance or uncontrollable inflammation that arise when either mechanism fails to work correctly. While many research fronts provide insight toward the mechanism of antibiotic resistance, understanding the misrecognition by the innate immune system proves complicated. The complexity arises because the mammalian host must distinguish the bacterial cell walls of the commensal (microbiome) and pathogenic bacteria. Although the bacterial cell wall polymer is conserved, we lack a fundamental understanding of the 3 dimensional architecture and moreover, the mechanism(s) by which the immune system dissects its structure to yield the appropriate immune-stimulatory fragments. There are many elegant ways to label the peptidoglycan of bacterial cell wall either through proteins that decorate the wall or through the incorporation of unnatural building blocks into the peptidoglycan biosynthetic machinery. Although these studies advanced the understanding of bacterial cell wall architecture, they were limited in that they all labeled on the peptide of the peptidoglycan. In order to understand these essential carbohydrates derived processes we developed a method to label on the conserved NAM unit of the polymer.

Peptidoglycan fragments such as N-acetyl-muramyl dipeptide (MDP) and N-glycolyl-MDP activate an immune response. N-acetyl-MDP is a highly conserved component of peptidoglycan and is found in both Gram-positive and Gram-negative bacteria, while N-glycolyl-MDP is specific to the Gram-positive bacteria *Mycobacterium avium*, the bacterium commonly found in patients suffering from Crohn's disease, a debilitating, non-curable, inflammatory bowel disease. In order to evade an innate immune response, pathogenic bacteria such as *Staphylococcus aureus*, *Listeria monocytogenes* and *Bacillus cereus* utilize acetylation and deacetylation strategies to avoid detection, generating fragments such as 2-amino-MDP. However it is not known how specific immune receptors respond to these peptidoglycan modifications.

Recently, N-acetyl-MDP was shown to directly interact with the human innate immune receptor protein Nod2, ultimately resulting in the activation of a signaling cascade known as the inflammatory response via the NF-κB and MAP kinase pathways, while N-glycolyl-MDP has been demonstrated to elicit a more robust Nod2-dependent inflammatory response via the same pathways. The differential effects of both the presence and identity of acyl substituents could have broad implications in immune recognition of bacteria. However it is not known how acetylation/deacetylation of these peptidoglycan fragments modulates molecular recognition by Nod2.

There remains a need for generation of various N-acetyl-muramic acid (NAM) derivatives and their corresponding peptidoglycan derivatives as they are essential tools for studying bacterial cell wall structure and function, and for modulating the innate immune response.

SUMMARY OF THE INVENTION

The present invention relates to N-acetyl-muramic acid (NAM) derivatives and methods for synthesizing and using the NAM derivatives.

An NAM derivative having Formula I is provided:

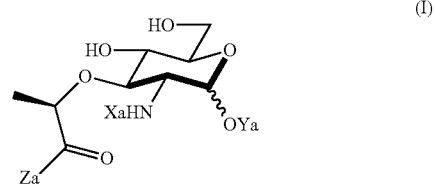

(I)

In the NAM derivative, Xa is selected from the group consisting of X1-X59 as shown in Table 1, Ya is selected from the group consisting of H, monophosphate, uridine diphosphate and ethyl azide linker prepared from 2-azido-ethanol, and Za is selected from the group consisting of OH, an ethylene diamine coupled fluorophore, a peptide and a peptide with an ethylene diamine coupled fluorophore, wherein the peptide is selected from the group consisting of a monopeptide, a dipeptide, a tripeptide and a pentapeptide. The NAM derivative may be a compound having a core structure as shown in Table 2.

Xa may be selected from the group consisting of X3-X8, X10-X22, X24-X25, X28, X30-X35 and X44-X59. Preferably, Xa is selected from the group consisting of X3-X8, X10-X21, X25, X28, X30, X31, X45-48 and X54-55.

Za may be OH. Where Za is a peptide, the NAM derivative may be selected from the group consisting of compounds E, F, H, J, L, M, O, P, R, S, AG, AH, AP, AQ, AS, AT, AV, or AW.

Where the NAM derivative is selected from the group consisting of compounds A, B, C, D, G, AH, AQ, AT, AW and BD, Xa may be selected from the group consisting of X3-X8, X10-X22, X24-X25, X28, X30-X35 and X44-X59, preferably selected from the group consisting of X3-X8, X10-X21, X25, X28, X30, X31, X45-48 and X54-55.

Where the NAM derivative is compound B or C, the NAM derivative may be synthesized in vitro in the presence of *P. putida* recycling enzymes AmgK and MurU.

Where Z is a peptide, the NAM derivative may be synthesized in vitro from compound B or C in the presence of *E. coli* biosynthetic enzymes MurC, MurD, MurE, and MurF.

In some preferred embodiments, the NAM derivative is compound A, C, D or BD.

In other preferred embodiments, the NAM derivative is unnatural, not naturally occurring. The NAM derivative may not be compound A1, A2, A9, D1, D2 or D9.

A method for synthesizing a NAM derivative is also provided. The method comprises (a) preparing imidazole-1-sulfonyl azide, (b) installing an azide protecting group at the 2-position of g to yield 2-azido-glucosamine, (c) acetylating the hydroxyl groups of 2-azido-glucosamine from step (b) to yield (2S,3R,4R,5S,6R)-6-(acetoxymethyl)-3-azido-tetrahydro-2H-pyran-2,4,5-triyl triacetate (I1), (d) selectively deacetylating the anomeric position of I1 from step (c) to yield (2R,3S,4R,5R)-2-(acetoxymethyl)-5-azido-6-hydroxytetrahydro-2H-pyran-3,4-diyl diacetate (I2), (e) installing a chloride at the anomeric position followed by performing a Koenigs-Knorr type reaction to place an O-benzyl protecting group in I2 from step (d) to yield (2R,3S,4R,5R)-2-(acetoxymethyl)-5-azido-6-(benzyloxy) tetrahydro-2H-pyran-3,4-diyl diacetate (I3), (f) removing the remaining acetates of I3 from step (e) by Zemplén deprotection to yield (2R,3S,4R,5R)-5-azido-6-(benzyloxy)-2-(hydroxymethyl)tetrahydro-2H-pyran-3,4-diol (I4), (g) installing a 4,6-O-benzylidene protecting group on I4 from step (f) to produce (2S,4aR,7R,8R,8aS)-7-azido-6-(benzyloxy)-2-phenylhexahydropyrano[3,2-d][1,3]dioxin-8-ol (I5), (h) adding sodium hydride and (S)-2-Chloropropionic acid to I5 from step (g) to produce (R)-2-(((2S,4aR,7R,8R,8aS)-7-azido-6-(benzyloxy)-2-phenylhexahydropyrano[3,2-d][1,3]dioxin-8-yl)oxy) propanoic acid (I6), and (j) deprotecting I6 from step (h) to yield a 2-amino-NAM. An NAM synthesized by the synthesis method is provided.

A method for modulating nucleotide-binding oligomerization domain-containing protein 2 (Nod2) in a cell is further provided. The method comprises exposing the cell with an effective amount of an NAM derivative. Preferably, the NAM derivative is not A2 or A9. The method may further comprise stabilizing the Nod2 in the cell. The method may further comprise activating nuclear factor kappa-light-chain-enhancer of activated B cells (NF-κB) in the cell.

A method for modifying the cell wall of a bacterial cell is further provided. The method comprises (a) exposing the bacterial cell to an effective amount of an NAM derivative, in which Za is OH, (b) making a peptidoglycan from the NAM derivative from step (a) in the bacterial cell, and (c) incorporating the peptidoglycan from step (b) into the cell wall of the bacterial cell. As a result, a modified peptidoglycan or a fragment thereof isolated from a modified cell wall of a bacterial cell is provided. In some embodiments, Xa is selected from the group consisting of X3-X8, X10-X22, X24-X25, X28, X30-X35 and X44-X59, preferably selected from the group consisting of X3-X8, X10-X21, X25, X28, X30, X31, X45-X48, X54 and X55.

A method for modulating an innate immune response of a subject to a bacterial cell is further provided. The method comprises exposing the subject to an effective amount of a modified cell wall of a bacterial cell obtained from the cell wall modulation method, or a fragment of the modified cell wall.

DETAILED DESCRIPTION OF THE INVENTION

Figure 1:
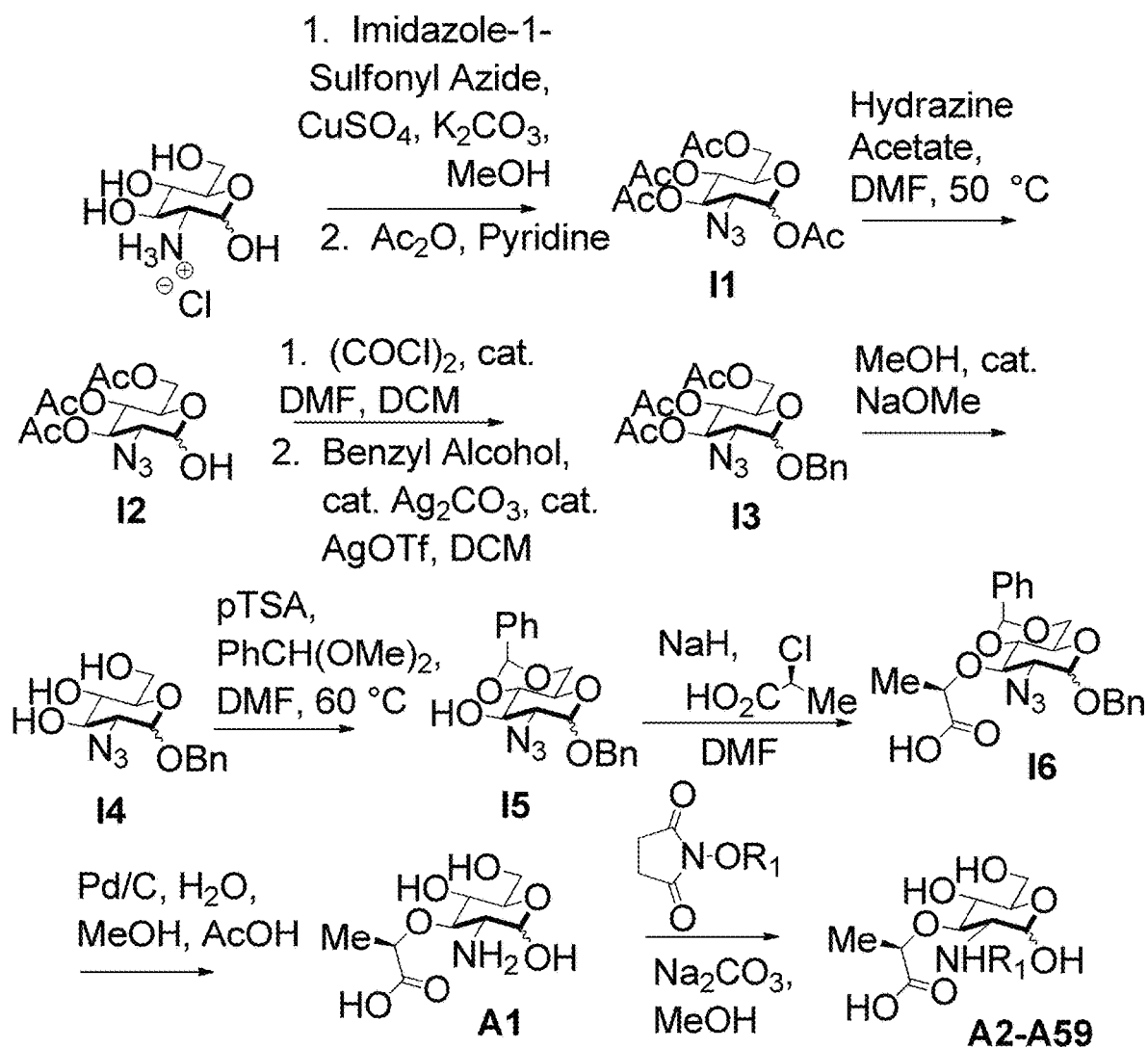
FIG. 1 illustrates Scheme S1 for synthesis of compounds A1-A59 and D1-D59.
Figure 1:
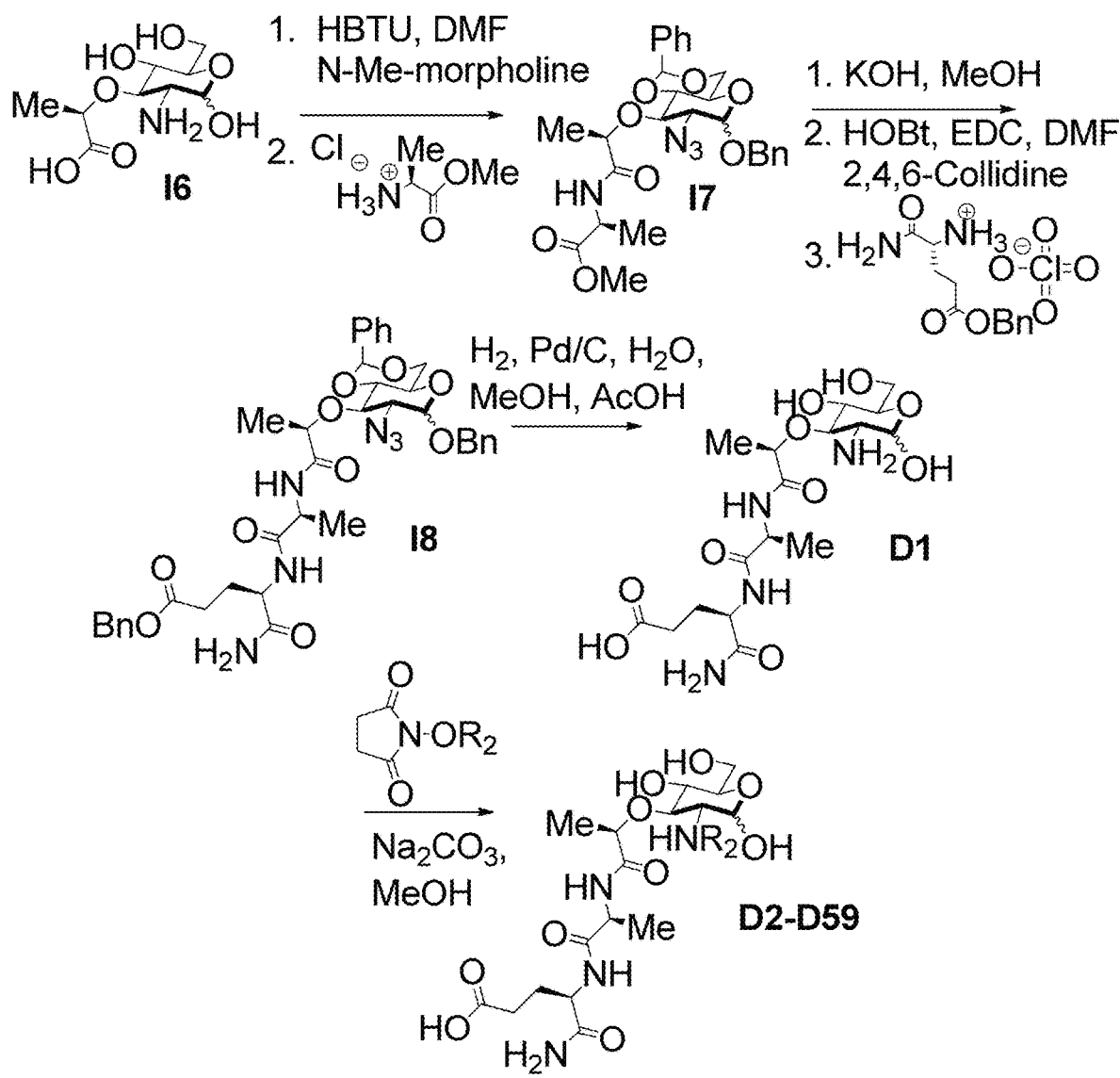

The present invention relates to N-acetyl-muramic acid (NAM) derivatives based on a newly developed synthetic process that allows the generation of various useful NAM derivatives. The NAM derivatives may be used in biological studies as, for example, NMR probes, imaging or affinity labels. The NAM derivatives may be used as the building blocks for making peptidoglycans in vitro or in vivo, which may be used to modify the cell wall of bacterial cells or modulate an innate immune response.

The term "peptide" used herein refers to a polymer of amino acids. A peptide having one, two, three or five amino acids, optional with one or more modifications such as an ethylene diamine linked fluorophore, is referred to as a mono, di, tri or penta peptide. The term "polypeptide" used herein refers to a peptide having at least 6 amino acids. The term "protein" used herein refers to a biological molecule comprising one or more polypeptides.

The term "derivative" used herein refers to a compound generated from an original compound by modifying one or more atoms or groups in the original compound via one or more chemical reactions, one or more biological reactions or a combination thereof. The original compound or the derivative may be either a natural product (i.e., naturally occurring) or an unnatural product (i.e, non-naturally occurring, artificial or recombinant). The original compound or the derivative may be either isolated (i.e., purified) or crude (i.e., unpurified). Preferably, the original compound is N-acetyl-muramic acid (NAM) and the derivative is an NAM derivative.

The term "N-acetyl-muramic acid (NAM) derivative" as used herein refers to a carbohydrate compound that is synthesized in vitro via chemical reactions, biological reactions, or a combination thereof. Preferably, the NAM derivative is an unnatural compound. The NAM derivative of the present invention is useful as a building block for making peptidoglycans. The NAM derivative may also be referred to as peptidoglycan fragments or peptidoglycan precursor. An NAM derivative may comprise a peptide, preferably a mono, di, tri or penta peptide.

The term "peptidoglycan" as used herein refers to a polymer in a bacterial cell wall that is composed of NAM and NAG with one or more amino acids attached to the NAM, and these peptides are further cross-linked by their amino acid residues, with or without glycine. An NAM derivative may be used to generate a corresponding peptidoglycan, which may be a natural product or an unnatural product, preferably an unnatural product.

According to a first aspect of the present invention, an N-acetyl-muramic acid (NAM) derivative is provided. The NAM derivative has Formula I:

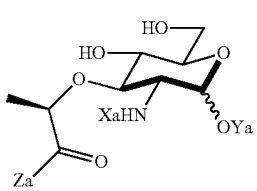

(I)

Xa may be selected from the group consisting of X1-X59 as shown in Table 1. Preferably, X is selected from the group consisting of X3-X8, X10X22, X24-X25, X28, X30-X35 and X44-X59. More preferably, X is selected from the group consisting of X3-X8, X10-X21, X25, X28, X30, X31, X45-48 and X54-55.

Ya may be selected from the group consisting of H, monophosphate, uridine diphosphate or ethyl azide linker, for example, prepared from 2-azido-ethanol.

Za may be selected from the group consisting of OH, an ethylene diamine coupled fluorophore, a peptide and a peptide with an ethylene diamine coupled fluorophore, wherein the peptide is selected from the group consisting of a monopeptide, a dipeptide, a tripeptide and a pentapeptide. The peptide may be coupled with fluorophore. Preferably, the peptide may have an ethylene diamine coupled fluorophore.

The NAM derivative may be a natural or an unnatural product. Preferably, the NAM derivative is an unnatural product.

Exemplary core structures with Ya and Za of NAM derivatives are shown in Table 2, wherein Xa may be selected from the group consisting of X1-X59 as shown in Table 1. An NAM derivative may be named by its compound name in Table 2 followed by its Xa group number in Table 1. For example, compound $A1_7$ is compound A as shown in Table 2 when Xa is X1 as shown in Table 1. In some preferred embodiments, the NAM derivative is not compound A1, A2, A9, D1, D2 or D9, i.e., compound A or D as shown in Table 2 when Xa is X1, X2 or X9 as shown in Table 1.

In one embodiment, the NAM derivative is selected from the group consisting of Compounds E, F, H, J, L, M, O, P, R, S, AG, AH, AP, AQ, AS, AT, AV and AW. In another embodiment, the NAM derivative is selected from the group consisting of Compounds A, B, C, D, G, AH, AQ, AT, AW and BD, in which Xa is selected from the group consisting of X3-X8, X10-X22, X24-X25, X28, X30-X35 and X44-X59, preferably selected from the group consisting of X3-X8, X10-X21, X25, X28, X30, X31, X45-48 and X54-55.

In some preferred embodiments, the NAM derivatives are 2-amino-muramyl dipeptide (MDP) derivatives, in which Xa is 1 and the peptide is di-peptide. Examples of 2-amino MDP are Compounds D and BD. In yet another preferred embodiment, the NAM derivatives are 2-amino NAM derivatives (A1), in which Xa is 1 without a peptide.

According to a second aspect of the present invention, a method for synthesizing the NAM derivative of the present invention is provided. The method comprises steps (a)-(j):

(a) preparing imidazole-1-sulfonyl azide, (b) installing an azide protecting group at the 2-position of g to yield 2-azido-glucosamine, (c) acetylating the hydroxyl groups of 2-azido-glucosamine from step (b) to yield (2S,3R,4R,5S,6R)-6-(acetoxymethyl)-3-azidotetrahydro-2H-pyran-2,4,5-triyl triacetate (I1), (d) selectively deacetylating the anomeric position of I1 from step (c) to yield (2R,3S,4R,5R)-2-(acetoxymethyl)-5-azido-6-hydroxytetrahydro-2H-pyran-3,4-diyl diacetate (I2), (e) installing a chloride at the anomeric position followed by performing a Koenigs-Knorr type reaction to place an O-benzyl protecting group in I2 from step (d) to yield (2R,3S,4R,5R)-2-(acetoxymethyl)-5-azido-6-(benzyloxy) tetrahydro-2H-pyran-3,4-diyl diacetate (I3), (f) removing the remaining acetates of I3 from step (e) by Zemplén deprotection to yield (2R,3S,4R,5R)-5-azido-6-(benzyloxy)-2-(hydroxymethyl)tetrahydro-2H-pyran-3,4-diol (I4), (g) installing a 4,6-O-benzylidene protecting group on I4 from step (f) to produce (2S,4aR,7R,8R,8aS)-7-azido-6-(benzyloxy)-2-phenylhexahydropyrano[3,2-d][1,3]dioxin-8-ol (3), (h) adding sodium hydride and (S)-2-Chloropropionic acid to I5 from step (g) to produce (R)-2-(a2S,4aR,7R,8R,8aS)-7-azido-6-(benzyloxy)-2-phenylhexahydropyrano[3,2-d][1,3]dioxin-8-yl)oxy)propanoic acid (I6), and (j) deprotecting I6 from step (h) to yield a 2-amino-NAM.

Figure 2:
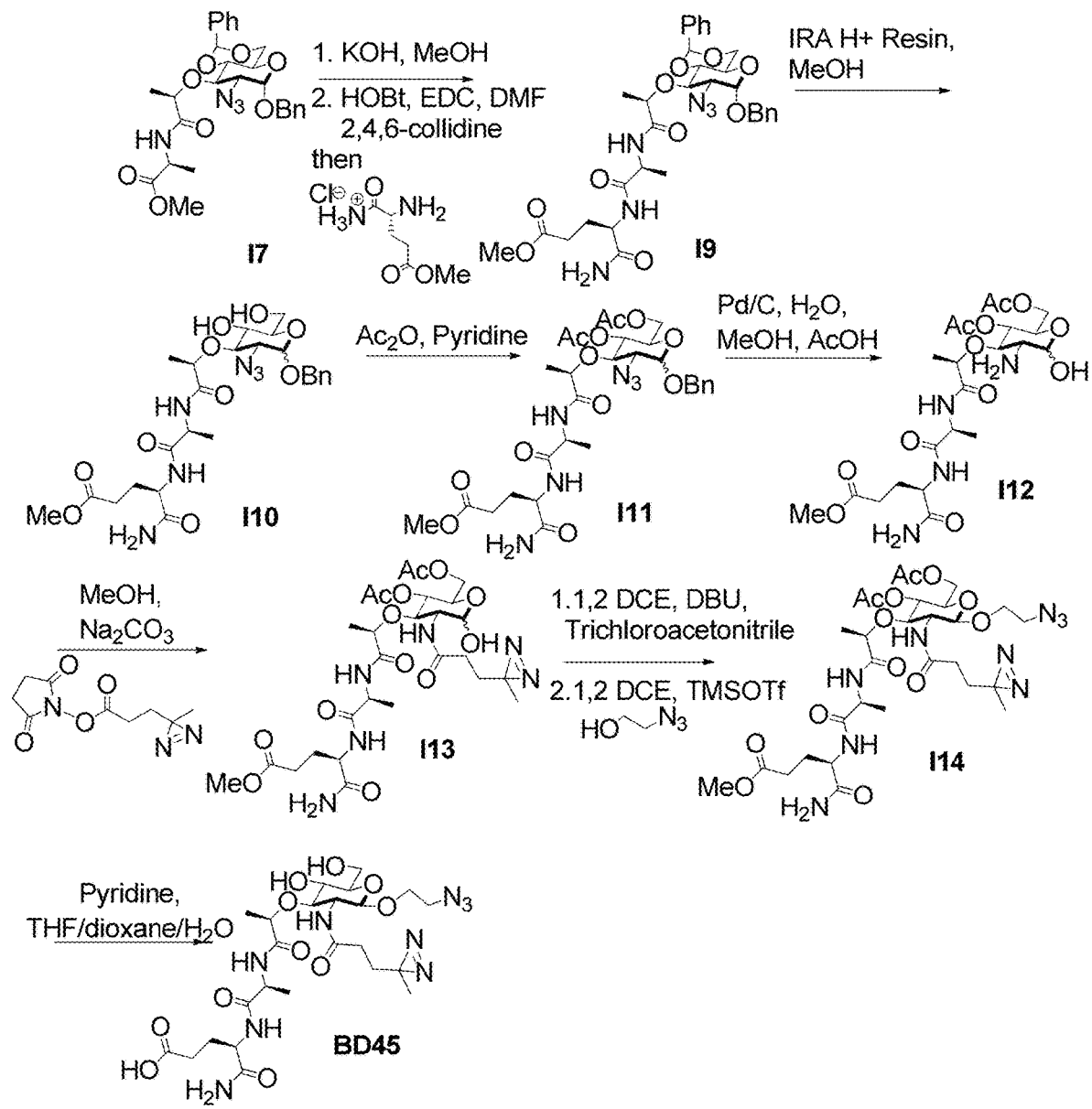
FIG. 2 illustrates Scheme S2 for synthesis of compounds BD45.

In some embodiments, NAM derivatives may be synthesized according to synthesis procedures as shown in Scheme S1 (FIG. 1) and Scheme S2 (FIG. 2). For example, Compounds A, wherein X is X1-X59 (also referred to as A1-A59), and Compounds D, wherein X is X1-X59 (also referred to as D1-D59) may be synthesized according to Scheme S1 while compound BD, wherein X is 45 (also referred as BD45) may be synthesized according to Scheme S2.

(2S,3R,4R,5S,6R)-6-(acetoxymethyl)-3-azidotetrahydro-2H-pyran-2,4,5-triyl triacetate (I1)

Preparation of Diazotransfer Reagent Imidazole-1-Sulfonyl Azide

To a solution of imidazole (79.00 g, 1.17 mol, 4.75 eq) in 633 mL of anhydrous dichloromethane was added a solution of sulfuryl chloride (20.0 mL, 0.25 mol, 1.0 eq) in 119 mL of anhydrous dichloromethane via cannulae transfer at 0° C. under $N_2$. Reaction warmed to room temperature and continued to stir under $N_2$ for 16 hours. The reaction was filtered and the filtrate condensed under reduced pressure to yield and off white solid. The solid was recrystallized in 80 mL of refluxing isopropanol to yield N,N'-sulfuryldiimidazole as a colorless crystalline solid (44.97 g 92%). $^1$H NMR (600 MHz, DMSO-d6) δ 8.51 (s, 1H), 7.92 (t, J=1.5 Hz, 1H), 7.26-7.24 (m, 1H), 3.33 (s, 1H). $^{13}$C NMR (151 MHz, DMSO-d6) δ 138.14, 132.38, 118.93.

N,N'-sulfuryldiimidazole (5.00 g, 25.2 mmol, 1.0 eq) was then suspended in 50 mL of anhydrous dichloromethane at 0° C. under $N_2$. Methyl trifluoromethanesulfonate (2.56 mL, 22.7 mmol, 0.9 eq) was added dropwise over 15 minutes at 0° C. The reaction stirred at 0° C. for 2 hours. The solvent was decanted off and 3-(imidazole-1-sulfonyl)-1-methyl-3H-imidazol-1-ium triflate was isolated as a white solid was washed three times each with 50 mL of cold dichloromethane and dried under high vacuum for 10 minutes and immediately used in the next reaction.

3-(Imidazole-1-sulfonyl)-1-methyl-3H-imidazol-1-ium triflate (9.31 g, 25.2 mmol, 1.0 eq) was dissolved in 30 mL of deionized $H_2O$ followed by 30 mL of ethyl acetate at 0° C. This solution stirred at 0° C. for 30 minutes. $NaN_3$ (1.97 g, 30.24 mmol, 1.2 eq) was added slowly and the reaction mixture stirred at 0° C. for 1 hour. The phases were separated and the organic layer was collected, dried over $Na_2SO_4$, and filtered. The filtrate containing the imidazole-1-sulfonyl azide was used directly in the diazotransfer reaction without further purification.

Preparation of (2S,3R,4R,5S,6R)-6-(acetoxymethyl)-3-azidotetrahydro-2H-pyran-2,4,5-triyl triacetate (I1)

To the imidazole-1-sulfonyl azide ethylacetate solution (40 mL, 25.2 mmol) was added sequentially N-acetyl D glucosamine HCl (6.52 g, 30.2 mmol, 1.2 eq), 82 mL of anhydrous methanol, $K_2CO_3$ (6.27 g, 45.4 mmol, 1.8 eq), and anhydrous $CuSO_4$ (0.0483 g, 0.302 mmol, 0.012 eq) at room temperature under $N_2$. The reaction continued to stir at room temperature for 16 hours. The reaction was filtered over celite and washed with 20 mL methanol. The solvent was then evaporated under reduced pressure and dried on the high vacuum overnight to yield a light yellow foam. To the light yellow foam was added 52 mL of anhydrous pyridine at 0° C. under $N_2$. To this mixture was added a solution of $Ac_2O$ (17 mL, 0.176 mol, 7.0 eq) and DMAP (0.2709 g, 2.22 mmol, 0.088 eq) dropwise at 0° C. The reaction warmed slowly to room temperature and continued to stir for 20 h. Product formation was confirmed by TLC (3:2 hexanes: ethyl acetate $r_f$ 0.5) with PAA staining. The reaction mixture was diluted with 100 mL of deionized water. The water layer was extracted three times with ethyl acetate (200 mL total). The organic layers were combined and washed three times with 1N HCl. The organic layer was dried over $Na_2SO_4$, filtered, and condensed. The brown oily residue was purified by flash chromatography 3:2 hexanes:ethyl acetate to yield tan foam (5.88 g, 63% over 4 steps). $^1$H NMR (400 MHz, Chloroform-d) δ 6.32 (d, J=3.7 Hz, 1H), 5.58 (d, J=8.6 Hz, 1H), 5.52-5.45 (m, 1H), 5.09 (dt, J=17.9, 9.4 Hz, 3H), 4.33 (dt, J=12.6, 3.8 Hz, 3H), 4.09 (td, J=12.4, 2.1 Hz, 4H), 3.83 (ddt, J=8.0, 4.3, 2.0 Hz, 2H), 3.73-3.67 (m, 2H), 2.22 (s, 4H), 2.13 (s, 1H), 2.12 (s, 3H), 2.10 (s, 4H), 2.07 (s, 1H), 2.05 (s, 3H). $^{13}$C NMR (101 MHz, Chloroform-d) δ 170.59, 170.10, 169.83, 169.65, 169.57, 168.60, 168.55, 92.57, 89.95, 72.72, 72.67, 70.74, 69.74, 67.81, 67.70, 62.53, 61.36, 60.26, 20.98, 20.93, 20.74, 20.72, 20.68, 20.60.

(2R,3S,4R,5R)-2-(acetoxymethyl)-5-azido-6-hydroxytetrahydro-2H-pyran-3,4-diyl diacetate (I2)

I1 (4.25 g, 11.4 mmol, 1.0 eq) and hydrazine acetate (1.26 g, 13.7 mmol, 1.2 eq) was dissolved in 11.7 mL of anhydrous N,N dimethylformamide under $N_2$. Reaction warmed to 50° C. and continued to stir under $N_2$ for 20 minutes. TLC 10% EtOAc/DCM confirmed product formation and disappearance of starting material. Reaction was cooled to room temperature, diluted with 12 mL of dichloromethane. The organic layer was washed with deionized water, saturated $NaHCO_3$ and brine. The organic layer was dried over $Na_2SO_4$, filtered and condensed to yield a yellow oil. The crude product was purified with flash chromatography with a gradient of 100% DCM to 10% EtOAC/DCM to 20% EtOAc/DCM. The purified product was isolated as a colorless oil (3.40 g, 90%). $^1$H NMR (600 MHz, Chloroform-d) δ 5.56-5.51 (m, 1H), 5.41-5.39 (m, 1H), 5.06 (t, J=9.6 Hz, 1H), 5.04-5.01 (m, 1H), 4.30-4.26 (m, 2H), 4.25-4.21 (m, 1H), 4.17-4.14 (m, 1H), 4.14-4.11 (m, 1H), 3.73 (ddt, J=7.2, 4.7, 2.2 Hz, 1H), 3.52-3.48 (m, 1H), 3.43 (dd, J=10.5, 3.4 Hz, 1H), 2.10 (s, 3H), 2.10 (s, 6H), 2.05 (s, 2H), 2.03 (s, 1H).

(2R,3S,4R,5R)-2-(acetoxymethyl)-5-azido-6-(benzyloxy)tetrahydro-2H-pyran-3,4-diyl diacetate (I3)

12 (4.97 g, 15.0 mmol, 1.0 eq) was dissolved in 150 mL of anhydrous dichloromethane under $N_2$ at room temperature with 4A activated molecular sieves. Anhydrous DMF (233 μL, 3.00 mmol, 0.2 eq) was added and the reaction stirred for 35 minutes. $(COCl)_2$ (2M, 9.01 mL) was added drop wise and the reaction stirred at room temperature for 1.5 hours. The reaction was filtered, washed with DCM and the solvent was evaporated under reduced pressure without heat. The yellow oil was then coevaporated twice with benzene and dried under high vacuum for 20 minutes. In a separate reaction flask, Ag$_2$CO$_3$ (41.4 g, 0.150 mol, 10 eq), AgOTf (0.088 g, 3.45 mmol, 0.23 eq), and anhydrous BnOH (7.77 mL, 75.1 mmol, 5.0 eq) were suspended in 400 mL of anhydrous dichloromethane under N$_2$ with 4A molecular sieves. The mixture was cooled to 0° C. and stirred for 15 minutes. At the same time, the yellow oily intermediate was dissolved in 170 mL of anhydrous dichloromethane under N$_2$ with 4A molecular sieves and stirred at room temperature for 15 minutes. The solution containing the intermediate was added dropwise to the reaction flask. The reaction slowly warmed to room temperature and continued to stir for 15 hours. The reaction mixture was filtered over celite. Product formation was confirmed by LC/MS and TLC (30% EtOAc/Hex). The organic layer was washed three times with deionized water, dried over Na$_2$SO$_4$, filtered and condensed. The resulting residue was purified with flash chromatography 100% hexanes to 5:1 hexanes:ethyl acetate. Purified product was isolated as a colorless oil (5.39 g, 85%). $^1$H NMR (600 MHz, Chloroform-d) δ 7.39 (d, J=5.0 Hz, 6H), 7.34 (qd, J=5.1, 3.1, 2.6 Hz, 3H), 5.56-5.48 (m, 1H), 5.07 (d, J=2.9 Hz, 1H), 5.06 (d, J=2.6 Hz, 2H), 5.04-5.00 (m, 1H), 4.96 (t, J=11.0 Hz, 1H), 4.75 (d, J=11.9 Hz, 1H), 4.64 (d, J=11.9 Hz, 1H), 4.26 (dd, J=12.1, 4.4 Hz, 1H), 4.06-4.00 (m, 2H), 3.99 (d, J=2.2 Hz, 1H), 3.63 (ddd, J=9.9, 4.6, 2.3 Hz, 1H), 3.34 (dd, J=10.8, 3.9 Hz, 1H), 2.10 (d, J=4.3 Hz, 5H), 2.08 (s, 3H), 2.03 (s, 3H), 2.01 (s, 1H). $^{13}$C NMR (151 MHz, Chloroform-d) δ 170.58, 169.99, 169.67, 136.03, 128.63, 128.59, 128.34, 128.27, 128.17, 100.25, 96.77, 72.52, 71.84, 71.28, 70.48, 70.22, 68.54, 68.45, 67.79, 63.71, 61.93, 61.78, 60.91, 20.75, 20.73, 20.71, 20.69, 20.60, 20.58.

(2R,3S,4R,5R)-5-azido-6-(benzyloxy)-2-(hydroxymethyl)tetrahydro-2H-pyran-3,4-diol (I4)

I3 (2.50 g, 5.93 mmol, 1.0 eq) was dissolved in anhydrous methanol under N$_2$. 0.5 M NaOMe (8.3 mL) was added dropwise. Reaction stirred at room temperature for 4 hours. Product formation was determined complete by TLC (10% MeOH/DCM). Reaction quenched with IRA H$^+$ resin in MeOH until reaction reached pH 4. The resin was filtered and the solvent was condensed under reduced pressure. Product was isolated as a colorless oil (1.67 g, 92%). $^1$H NMR (600 MHz, Chloroform-d) δ 7.39 (d, J=7.5 Hz, 4H), 7.33 (t, J=7.6 Hz, 4H), 7.28 (t, J=7.4 Hz, 2H), 4.96 (d, J=3.5 Hz, 2H), 4.93 (d, J=11.8 Hz, 1H), 4.76 (d, J=11.9 Hz, 2H), 4.69 (d, J=11.8 Hz, 1H), 4.59-4.54 (m, 3H), 4.40 (d, J=7.9 Hz, 1H), 3.91-3.84 (m, 2H), 3.80 (d, J=12.0 Hz, 1H), 3.69 (d, J=5.8 Hz, 2H), 3.65-3.61 (m, 1H), 3.35 (t, J=9.3 Hz, 1H), 3.24 (d, J=8.6 Hz, 1H), 3.21-3.17 (m, 1H), 3.11 (d, J=10.1 Hz, 1H). $^{13}$C NMR (151 MHz, Chloroform-d) δ 131.93, 131.62, 131.38, 100.95, 76.68, 75.13, 74.66, 72.84, 70.79, 67.10, 64.98, 51.96, 51.82, 51.68, 51.54, 51.40, 51.26, 51.11.

(2S,4aR,7R,8R,8aS)-7-azido-6-(benzyloxy)-2-phenylhexahydropyrano[3,2-d][1,3]dioxin-8-ol (I5)

I4 (2.70 g, 9.15 mmol, 1.0 eq), pTSA (0.348 g, 1.83 mmol, 0.2 eq), and PhCH(OMe)$_2$ (4.12 mL, 27.5 mmol, 3.0 eq) were dissolved in 22 mL DMF under N$_2$. The reaction was put under vacuum and heated to 60° C. for 1.5 hours. PhCH(OMe)$_2$ (4.12 mL, 27.5 mmol, 3.0 eq) was added to the reaction at 60° C. and continued to stir under vacuum for 1.5 hours. TLC (100% DCM) confirmed that the reaction was complete. Once the vacuum was removed and the flask cooled to room temperature, the reaction was quenched with mL of saturated NaHCO$_3$ and stirred for 20 minutes. The reaction was diluted with DCM and extracted three times. The organic layers were combined and washed three times with 1N HCl. The organic layer was dried over Na$_2$SO$_4$, filtered, and condensed to yield a yellow oil. The product was purified with column chromatography (100% hexanes to 5% EtOAc/hexanes to 50% EtOAc/hexanes). The clean product was isolated as a colorless oil (g, quantitative). $^1$H NMR (600 MHz, Chloroform-d) δ 7.52-7.46 (m, 3H), 7.42-7.37 (m, 10H), 7.34 (d, J=7.3 Hz, 1H), 5.55 (s, 1H), 5.54 (s, 1H), 5.00 (d, J=3.7 Hz, 1H), 4.94 (d, J=11.7 Hz, 1H), 4.77 (d, J=12.0 Hz, 1H), 4.71 (d, J=11.7 Hz, 1H), 4.62 (d, J=12.0 Hz, 1H), 4.37 (dd, J=10.5, 5.0 Hz, 1H), 4.28 (td, J=9.7, 2.5 Hz, 1H), 4.24 (dd, J=10.3, 4.9 Hz, 1H), 3.91 (td, J=10.0, 5.0 Hz, 1H), 3.82 (t, J=10.3 Hz, 1H), 3.74 (t, J=10.3 Hz, 1H), 3.66 (td, J=9.4, 2.5 Hz, 1H), 3.61-3.56 (m, 1H), 3.56-3.52 (m, 1H), 3.41 (td, J=9.6, 5.0 Hz, 1H), 3.31 (dd, J=10.0, 3.7 Hz, 1H), 2.66 (dd, J=12.3, 2.6 Hz, 1H). $^{13}$C NMR (151 MHz, Chloroform-d) δ 162.53, 129.29, 128.55, 128.33, 128.22, 128.19, 128.10, 128.07, 126.67, 126.29, 102.06, 97.60, 81.99, 69.91, 68.82, 68.73, 63.26, 62.68, 52.73, 36.47, 31.43.

(R)-2-(((2S,4aR,7R,5R,8aS)-7-azido-6-(benzyloxy)-2-phenylhexahydropyrano[3,2-d][1,3]dioxin-8-yl)oxy)propanoic acid (I6)

I5 (2.1448 g, 5.6 mmol, 1.0 eq) was dissolved in 30 mL of DMF under N$_2$. NaH (60% in oil, 1.399 g, 35.0 mmol, 6.25 eq) was added slowly and reaction stirred at room temperature under N$_2$ for 30 minutes. To the reaction was added (S)-(−)-2-chloropropionic acid (2.43 mL, 28.0 mmol, 5.0 eq), with H$_2$ gas evolution observed. The reaction stirred for 30 minutes then NaH (60% in oil, 1.399 g, 35.0 mmol, 6.25 eq) was added. The reaction stirred at room temperature for 16 hours. The reaction was quenched slowly with deionized water at 0° C. The pH of the solution was brought to 4 with the addition of 1N HCl. A gummy brown solid formed in the reaction flask. The aqueous liquid was decanted off and passed through a fine filter funnel. Any brown residue in the frit was dissolved in EtOAc and combined with the solid in the reaction flask. The aqueous filtrate was extracted three times with EtOAc. All organic solutions were combined and washed with 1N HCl, dried over Na$_2$SO$_4$, filtered and condensed to yield a brown oily solid. The residue was purified by flash chromatography with a gradient of 2.5% MeOH/DCM with 0.01% AcOH to 5% MeOH/DCM with 0.01% AcOH. Isolated product as a light yellow foam (2.25 g, 88%). $^1$H NMR (600 MHz, Chloroform-d) δ 8.03 (s, 1H), 7.43 (td, J=7.8, 3.7 Hz, 5H), 7.41-7.38 (m, 14H), 7.36-7.33 (m, 2H), 5.56 (d, J=5.3 Hz, 1H), 5.08 (d, J=3.7 Hz, 1H), 4.76 (d, J=11.8 Hz, 1H), 4.63 (d, J=11.8 Hz, 1H), 4.51-4.42 (m, 2H), 4.39 (dd, J=10.5, 5.1 Hz, 1H), 4.23 (dd, J=10.3, 4.9 Hz, 1H), 4.02 (t, J=9.5 Hz, 1H), 3.90 (td, J=10.0, 4.9 Hz, 1H), 3.83 (t, J=10.3 Hz, 1H), 3.75 (t, J=10.3 Hz, 1H), 3.69 (t, J=9.2 Hz, 1H), 3.67-3.61 (m, 1H), 3.56 (dd, J=9.7, 8.1 Hz, 1H), 3.45-3.38 (m, 2H), 2.17 (s, 1H), 1.47 (d, J=6.9 Hz, 4H). $^{13}$C NMR (151 MHz, Chloroform-d) δ 174.60, 162.73, 136.76, 136.05, 129.29, 129.22, 128.64, 128.39, 128.35, 128.27, 125.85, 125.80, 101.60, 101.52, 101.04, 96.86, 82.36, 81.32, 78.90, 76.58, 76.29, 71.56, 70.08, 68.74, 68.44, 66.18, 64.83, 62.69, 62.26, 36.56, 31.51, 30.93, 18.96.

(R)-2-(((3R,4R,5S,6R)-3-amino-2,5-dihydroxy-6-(hydroxymethyl)tetrahydro-2H-pyran-4-yl)oxy)propanoic acid (A1)

I6 (0.987 g, 2.17 mmol, 1.0 eq) was dissolved in a solution of 62 mL H$_2$O, 46 mL MeOH and 7.7 mL AcOH under N$_2$.

Pd/C (0.950 g) was added to the reaction under $N_2$ and then a hydrogen atmosphere was introduced. The reaction stirred at room temperature under $H_2$ for 16 hours. LC/MS confirmed product formation. The $H_2$ was removed and the Pd was filtered over celite and rinsed with MeOH, then water, being careful not to dry out the Pd. The filtrate was condensed and purified on the Waters preparative HPLC/MS with the method as follows: flow rate 20 mL/min, 0.1% formic acid in millipure $H_2O$ as eluent A and 0.1% formic acid in HPLC grade acetonitrile as eluent B with a 5 minute method of 0-4 min 95A-5A. The fractions were combined and lyophilized to give a white powder (0.350 g, 65%). $^1$H NMR (600 MHz, Chloroform-d) δ 5.30 (d, J=3.5 Hz, 1H), 4.77 (d, J=8.4 Hz, 1H), 4.42-4.38 (m, 1H), 4.38-4.34 (m, 1H), 3.85 (dd, J=11.9, 2.1 Hz, 1H), 3.79 (t, J=2.5 Hz, 1H), 3.78-3.77 (m, 2H), 3.72 (dd, J=12.3, 5.5 Hz, 1H), 3.68 (dd, J=11.9, 5.7 Hz, 1H), 3.63-3.58 (m, 1H), 3.50 (d, J=9.3 Hz, 1H), 3.48 (d, J=2.8 Hz, 1H), 3.46 (d, J=8.7 Hz, 1H), 3.37-3.33 (m, 1H), 3.07 (dd, J=10.5, 3.6 Hz, 1H), 2.79 (dd, J=10.6, 8.4 Hz, 1H), 1.46-1.38 (m, 7H). $^{13}$C NMR (151 MHz, Chloroform-d) δ 97.75, 93.25, 82.18, 81.98, 80.75, 75.84, 75.02, 64.55, 57.97, 51.96, 51.82, 51.68, 51.53, 51.39, 51.25, 51.11, 22.63. High Res LC/MS (S)-methyl-2-((R)-2-(((2S,4aR,6R,7R,5R,8aS)-7-azido-6-(benzyloxy)-2-phenylhexahydropyrano[3,2-d][1,3]dioxin-8-yl)oxy)propanamido)propanoate (I7)

I6 (300.0 mg, 0.659 mmol) dissolved in 6 mL anhydrous N,N-dimethylformamide under $N_2$ gas. N-methylmorpholine (218.0 μL, 1.98 mmol) and N,N,N',N'-Tetramethyl-O-(1H-benzotriazol-1-yl)uronium hexafluorophosphate (HBTU) (500.6 mg, 1.32 mmol) were subsequently added and the reaction was allowed to stir for 10 mins before L-alanine methyl ester hydrochloride (184.0 mg, 1.32 mmol) was added. The reaction stirred for 20 hours and was quenched with 6 mL water and then diluted with ethyl acetate. The phases were separated and the organic phase was washed with 1 N hydrochloride, saturated sodium bicarbonate, brine and was dried with sodium sulfate. The organic phase was evaporated and purified by column chromatography (2% methanol/dichloromethane) to yield a white powder (286.3 mg, 81%). $^1$H NMR (600 MHz, Chloroform-d) (Anomers—1.00 α: 0.48 β) δ 7.92 (d, J=7.7 Hz, 1H, β N—H), 7.69 (d, J=7.6 Hz, 1H, α N—H), 7.49-7.40 (m, 5H, aromatic), 7.40-7.32 (m, 15H, aromatic), 5.57 (s, 1H, β 4,6-benzylidene C—H), 5.56 (s, 1H, α 4,6-benzylidene C—H), 5.11 (d, J=3.6 Hz, 1H, α 1-H), 4.96 (d, J=11.5 Hz, 1H, β benzyl methylene), 4.77 (d, J=11.8 Hz, 1H, α benzyl methylene), 4.72 (d, J=11.5 Hz, 1H, β 4,6 benzylidene), 4.64-4.55 (m, 4H, α 4,6-benzylidene, α and β C—H alanine, β1-H), 4.42-4.28 (m, 3H, β 6-H, α and β C—H), 4.24 (dd, J=10.3, 4.9 Hz, 1H, α 6-H) 3.99-3.87 (m, 2H, α 3-H, α 5-H), 3.82 (t, J=10.3 Hz, 1H, β 6'-H), 3.75 (m, 7H, α 6'-H, α and β methyl ester), 3.67 (t, J=9.2 Hz, 1H, β 4-H), 3.62 (t, J=9.3 Hz, 1H, α 4-H), 3.55 (dd, J=9.5, 7.8 Hz, 1H, (β 2-H), 3.43-3.34 (m, 3H, α 2-H, β 5-H, β 5-H), 1.45 (d, J=7.2 Hz, 3H, α alanine methyl), 1.44 (d, J=7.1 Hz, 3H, β alanine methyl), 1.42 (d, J=6.8 Hz, 3H, α methyl), 1.41 (d, J=6.9 Hz, 3H, β methyl). $^{13}$C NMR (151 MHz, Chloroform-d) δ 173.34 (carbonyl), 173.19 (carbonyl), 172.88 (carbonyl), 172.66 (carbonyl), 136.91 (aromatic), 136.80 (aromatic), 136.25 (aromatic), 136.24 (aromatic), 129.36 (aromatic), 129.34 (aromatic), 128.76 (aromatic), 128.73 (aromatic), 128.55 (aromatic), 128.52 (aromatic), 128.47 (aromatic), 128.44 (aromatic), 128.38 (aromatic), 128.32 (aromatic), 126.02 (aromatic), 125.96 (aromatic), 101.80 (α 4,6-benzylidene C—H), 101.69 (β 4,6-benzylidene C—H), 101.55 (β1-C), 97.17 (α 1-C), 82.78 (α 4-C), 82.12 (β 4-C), 78.42 (α C—H), 78.33 (β3-C), 78.13 (β C—H), 76.31 (α 3-C), 71.72 (β benzyl methylene), 70.16 (α benzyl methylene), 68.89 (α 6-C), 68.63 (β 6-C), 66.23 (β 5-C), 65.43 (β 2-C), 62.88 (α 5-C), 62.79 (α 2-C), 52.57 (β methyl ester), 52.53 (a methyl ester), 47.95 (β alanine C—H), 47.84 (α alanine C—H), 19.74 (α methyl), 19.55 (β methyl), 18.52 (β alanine methyl), 18.21 (α alanine methyl). LRMS (ESI-Pos) for $C_{27}H_{32}N_4O_7$ (540.22): 541.20 $[M+H]^+$.

(R)-benzyl 5-amino-4-((S)-2-((R)-2-(((2S,4aR,6R,7R,8R,8aS)-7-azido-6-(benzyloxy)-2-phenylhexahydropyrano[3,2-d][1,3]dioxin-8-yl)oxy)propanamido)propanamido)-5-oxopentanoate (I8)

I7 (119.0 mg, 0.220 mmol) dissolved in 7 mL methanol. Subsequently 2 mL of 0.5M of potassium hydroxide was added and the reaction was monitored by TLC (7% methanol/dichloromethane) until complete. The solvent was then evaporated and the white solid was co-evaporated with toluene (3×) and subsequently dissolved in 4 mL of anhydrous N,N-dimethylformamide under $N_2$ gas. 1-Hydroxybenzotriazole hydrate (wetted with not less than 20 wt % water) (44.6 mg, 0.264 mmol), 2,4,6-trimethylpyridine (87.2 μL, 0.660 mmol) and then 1-ethyl-3-(3-dimethylaminopropyl)carbodiimide (63.3 mg, 0.330 mmol) were subsequently added and the reaction was allowed to stir for 2 mins before D-γ-benzyl Isoglutamine perchlorate (104.0 mg, 0.309 mmol) was added. The reaction stirred 16 hrs and was quenched with 4 mL water and then diluted with ethyl acetate. The phases were separated and the organic phase was washed with 1 N hydrochloride, saturated sodium bicarbonate, brine and was dried with sodium sulfate. The organic phase was evaporated and purified by column chromatography (5% methanol/dichloromethane) to yield a white powder (146.1 mg, 89% yield). $^1$H NMR (600 MHz, Chloroform-d) (Anomers—1.00 α: 0.61 β) δ 7.85 (d, J=6.0 Hz, 1H, β alanine N—H), 7.65 (d, J=6.1 Hz, 1H, α alanine N—H), 7.47-7.28 (m, 30H, aromatic), 7.14 (d, J=7.5 Hz, 2H, α and β isoglutamine N—H), 5.56 (s, 1H, β 4,6-benzylidene C—H), 5.55 (s, 1H, α 4,6-benzylidene C—H), 5.15-5.07 (m, 3H, α 1-H, α and β isoglutamine benzyl methylene), 4.95 (d, J=11.5 Hz, 1H, β benzyl methylene), 4.77 (d, J=11.8 Hz, 1H, α benzyl methylene), 4.71 (d, J=11.5 Hz, 1H, β benzyl methylene), 4.62 (d, J=11.8 Hz, 1H, α benzyl methylene), 4.56 (d, J=8.0 Hz, 1H, β1-H), 4.46 (td, J=8.2, 4.8 Hz, 2H, α and β isoglutamine C—H), 4.38 (dd, J=10.6, 5.0 Hz, 1H, β6-H), 4.33 (q, J=6.8 Hz, 1H, C—H), 4.30-4.22 (m, 4H, α C—H, α and β alanine C—H, α 6-H), 3.96-3.86 (m, 2H, α 3-H, α 5-H), 3.82 (t, J=10.3 Hz, 1H, β 6'-H), 3.75 (t, J=10.3 Hz, 1H, α 6'-H), 3.66 (t, J=9.2 Hz, 1H, (β 4-H), 3.61 (t, J=9.3 Hz, 1H, α 4-H), 3.54 (dd, J=9.8, 8.1 Hz, 1H, β2-H), 3.44-3.33 (m, 3H, α 2-H, β5-H, β3-H), 2.58 (ddd, J=17.3, 9.1, 5.0 Hz, 2H, α and β isoglutamine methylene), 2.51-2.41 (m, 2H, α and β isoglutamine methylene), 2.22 (dddd, J=14.4, 12.2, 7.8, 3.7 Hz, 2H, α and β isoglutamine methylene), 2.07-1.96 (m, 2H, α and β isoglutamine methylene), 1.40 (d, J=7.0 Hz, 6H, α and β alanine methyl), 1.38 (d, J=6.9 Hz, 6H, α and β methyl). $^{13}$C NMR (151 MHz, Chloroform-d) δ 174.32 (carbonyl), 174.14 (carbonyl), 173.71 (carbonyl), 173.69 (carbonyl), 173.28 (carbonyl), 173.27 (carbonyl), 172.38 (carbonyl), 172.35 (carbonyl), 136.86 (aromatic), 136.77 (aromatic), 136.15 (aromatic), 135.76 (aromatic), 135.73 (aromatic), 129.38 (aromatic), 129.35 (aromatic), 128.79 (aromatic), 128.74 (aromatic), 128.73 (aromatic), 128.55 (aromatic), 128.53 (aromatic), 128.52 (aromatic), 128.48 (aromatic), 128.41 (aromatic), 128.39 (aromatic), 128.36 (aromatic), 125.99 (aromatic), 125.93 (aromatic), 101.79 (α 4,6-benzylidene C—H), 101.68 (β 4,6-benzylidene C—H), 101.44 (β 1-C), 96.97 (α 1-C), 82.68 (α 4-C), 82.07 (β4-C), 78.27 (β3-C), 78.23 (α C—H), 77.90 (β C—H), 76.45 (α 3-C), 71.70 (β benzyl methylene), 70.21 (α benzyl methylene), 68.85 (α 6-C), 68.60 (β 6-C), 66.82 (α isoglutamine benzyl methylene), 66.80 (β isoglutamine benzyl methylene), 66.20 (β5-C), 65.15 (β2-C), 62.86 (α 5-C), 62.56 (α 2-C), 52.59 (α isoglutamine C—H), 52.52 (β isoglutamine C—H), 49.67 (α and β alanine C—H), 30.80 (α and β isoglutamine methylene), 26.89 (β isoglutamine methylene), 26.78 (α isoglutamine methylene), 19.74 (α methyl), 19.58 (β methyl), 16.99 (β alanine methyl), 16.89 (α alanine methyl). LRMS (ESI-Pos) for $C_{38}H_{44}N_6O_{10}$ (744.31): 745.25 [M+H]$^+$. IR (ATR probe): Azide-2105.90 cm$^{-1}$ (medium).

(R)-5-amino-4-((S)-2-((R)-2-(((2R,3R,4R,5S,6R)-3-amino-2,5-dihydroxy-6-(hydroxymethyl)tetrahydro-2H-pyran-4-yl)oxy)propanamido)propanamido)-5-oxopentanoic acid (D1)

I8 (108.0 mg, 0.145 mmol) dissolved in 6.4 mL water, 4.8 mL methanol and 0.80 mL acetic acid with stirring at room temperature. 10% palladium on carbon (60.0 mg, 0.054 mmol) added and the reaction was degassed and stirred under H$_2$ gas for 17 hrs. The reaction was monitored by mass-spectrometry and filtered through celite upon completion. Purified by HPLC (5% acetonitrile in water with 0.1% trifluoroacetic acid—isocratic flow for 30 mins). White solid (quantitative yield). $^1$H NMR (600 MHz, Deuterium Oxide) (Anomers—1.00α: 0.61β) δ 5.41 (d, J=3.5 Hz, 1H, α 1-H), 4.91 (d, J=8.4 Hz, 1H, β 1-H), 4.72 (q, J=6.9 Hz, 1H, β C—H), 4.67 (q, J=6.7 Hz, 1H, α C—H), 4.38-4.30 (m, 4H, α and β alanine C—H, α and β isoglutamine C—H), 3.89-3.84 (m, 2H, α 5-H, β 6-H), 3.82 (dd, J=12.3, 2.0 Hz, 1H, α 6-H), 3.76 (dd, J=12.3, 5.0 Hz, 1H, α 6'-H), 3.74-3.66 (m, 2H, α 3-H, β 6'-H), 3.64-3.58 (m, 2H, α 4-H, β 6-H), 3.56-3.51 (m, 1H, β 3-H), 3.48 (ddd, J=9.8, 5.6, 1.9 Hz, 1H, β 5-H), 3.30 (dd, J=10.4, 3.5 Hz, 1H, α 2-H), 3.01 (dd, J=10.4, 8.6 Hz, 1H, β 2-H), 2.53-2.43 (m, 4H, α and β isoglutamine methylene), 2.22-2.12 (m, 2H, α and β isoglutamine methylene), 2.04-1.94 (m, 2H, α and β isoglutamine methylene), 1.44-1.36 (m, 12H, α and β methyl, α and β alanine methyl). $^{13}$C NMR (151 MHz, Deuterium Oxide) δ 176.90 (carbonyl), 176.86 (carbonyl), 175.95 (carbonyl), 175.94 (carbonyl), 175.85 (carbonyl), 175.75 (carbonyl), 175.37 (carbonyl), 175.29 (carbonyl), 92.63 (β1-C), 88.85 (α 1-C), 78.51 (β 3-C), 76.81 (α 3-C), 76.36 (α C—H), 76.02 (β C—H), 75.86 (β 5-C), 71.38 (α 5-C), 70.48 (β 4-C), 70.19 (α 4-C), 60.16 (β 6-C), 59.98 (α 6-C), 55.65 (β 2-C), 53.37 (α 2-C), 52.85 (α isoglutamine C—H), 52.78 (β isoglutamine C—H), 49.98 (α alanine C—H), 49.81 (β alanine C—H), 30.06 (α and β isoglutamine methylene), 26.11 (β isoglutamine methylene) 26.00 (α isoglutamine methylene) 18.99 (β methyl), 18.90 (a methyl), 16.50 (β alanine methyl), 16.40 (α alanine methyl). HRMS (ESI-Pos) for $C_{12}H_{30}N_4O_{10}$ (450.19619): 451.20347 [M+H]$^+$.

General Procedure for R1 to Installation Through A) N Hydroxy Succinimide (NHS) Activated Ester Coupling Step 1—general preparation of NHS ester containing R1: Desired carboxyllic acid (1.0 eq) was dissolved in anhydrous DMF (0.5M) under N$_2$. N-hydroxysuccinimide (1.05 eq) was added to the reaction followed by N-(3-dimethylaminopropyl)-N'-ethylcarbodiimide hydrochloride (EDC) (1.2 eq). The reaction stirred under N$_2$ at room temperature for 14 hours. The reaction was concentrated, quenched with deionized water and extracted three times with EtOAc. The organic layers were combined and washed three times with 1N HCl, three times with saturated NaHCO$_3$, and brine. The organic layer was dried over Na$_2$SO$_4$, filtered and condensed to yield a solid product. The solid was washed three times with anhydrous Et$_2$O and dried under high vacuum to yield a white solid. Step 2—General Synthetic Preparation for all core structures: To a core structure containing one of the following (1.0 eq) and Na$_2$CO$_3$ (5 eq) was added anhydrous MeOH under N$_2$. NHS ester as prepared in Step 1 or anhydride above was added. Once complete, the reaction can be quenched with IRA H+ resin if desired. For purification, the solid was either triturated with Et$_2$O to give an off white crystalline solid.

General Procedure for R1 Installation Through B) Mild Acetylation Conditions Using Anhydrides Core structure (1.0 eq) and sodium bicarbonate (2.4 eq) dissolved in 1.0 mL water with stirring at room temperature. Acetic anhydride (1.1 eq) added dropwise and reaction stirred for 1.5 hrs. The reaction was subsequently quenched with Amberlite IR120, H form ion exchange resin. The mixture was filtered and evaporated and triturated with Et$_2$O if necessary for purification.

A1: $^1$H NMR (600 MHz, Methanol-d$_4$) δ 5.30 (d, J=3.5 Hz, 1H), 4.77 (d, J=8.4 Hz, 1H), 4.42-4.38 (m, 1H), 4.38-4.34 (m, 1H), 3.85 (dd, J=11.9, 2.1 Hz, 1H), 3.79 (t, J=2.5 Hz, 1H), 3.78-3.77 (m, 2H), 3.72 (dd, J=12.3, 5.5 Hz, 1H), 3.68 (dd, J=11.9, 5.7 Hz, 1H), 3.63-3.58 (m, 1H), 3.50 (d, J=9.3 Hz, 1H), 3.48 (d, J=2.8 Hz, 1H), 3.46 (d, J=8.7 Hz, 1H), 3.37-3.33 (m, 1H), 3.07 (dd, J=10.5, 3.6 Hz, 1H), 2.79 (dd, J=10.6, 8.4 Hz, 1H), 1.46-1.38 (m, 7H). $^{13}$C NMR (151 MHz, Methanol-d$_4$) δ 97.75, 93.25, 82.18, 81.98, 80.75, 75.84, 75.02, 64.55, 57.97, 51.96, 51.82, 51.68, 51.53, 51.39, 51.25, 51.11, 22.63. High Resolution LC/MS (ESI-pos [M+H]$^+$=252.10712, −2.62111 ppm)

A24. $^1$H NMR (600 MHz, Methanol-d$_4$) δ 5.36 (d, J=3.0 Hz, 1H), 4.69-4.64 (m, 1H), 4.62-4.58 (m, 1H), 4.55 (d, J=8.0 Hz, 0H), 3.87-3.81 (m, 1H), 3.76 (dt, J=9.8, 3.4 Hz, 3H), 3.72-3.65 (m, 4H), 3.61 (dd, J=10.9, 3.1 Hz, 2H), 3.51 (d, J=9.4 Hz, 1H), 3.47 (d, J=14.0 Hz, 1H), 2.78 (dq, J=14.1, 6.9 Hz, 4H), 2.54-2.48 (m, 4H), 2.17 (s, 4H), 1.42 (t, J=7.7 Hz, 4H). $^{13}$C NMR (151 MHz, Methanol-d$_4$) δ 212.44, 181.24, 177.52, 96.22, 94.31, 81.44, 81.39, 80.29, 79.37, 79.15, 76.99, 75.99, 75.55, 65.03, 58.38, 51.96, 51.82, 51.77, 51.68, 51.63, 51.53, 51.48, 51.39, 51.35, 51.30, 51.25, 51.19, 51.11, 41.74, 41.25, 33.30, 32.24, 31.25, 21.91. High Resolution LC/MS (ESI-neg [M−H]$^-$= 348.12961, −1.12420 ppm)

A25: $^1$H NMR (600 MHz, Methanol-d$_4$) δ 5.39 (d, J=3.0 Hz, 1H), 4.86 (s, 6H), 4.69 (q, J=7.0 Hz, 1H), 3.93-3.91 (m, 4H), 3.77 (t, J=2.7 Hz, 1H), 3.75 (d, J=2.5 Hz, 2H), 3.72 (d, J=2.1 Hz, 1H), 3.70 (d, J=3.7 Hz, 1H), 3.69-3.68 (m, 1H), 3.66 (d, J=3.2 Hz, 1H), 3.52 (t, J=9.0 Hz, 1H), 1.42 (d, J=7.0 Hz, 3H), 1.40 (d, J=7.0 Hz, 1H). $^{13}$C NMR (151 MHz, Methanol-d$_4$) δ 94.16, 81.20, 79.10, 76.03, 75.69, 65.13, 64.96, 58.46, 55.72, 51.96, 51.82, 51.68, 51.54, 51.25, 51.11, 21.86. High Resolution LC/MS (ESI-neg [M−H]$^-$= 333.10550, 1.02316 ppm)

A28: $^1$H NMR (600 MHz, Methanol-d$_4$) δ 5.43 (d, J=3.0 Hz, 1H), 4.58 (q, J=6.8 Hz, 1H), 4.55-4.52 (m, 1H), 3.85-3.80 (m, 1H), 3.79-3.73 (m, 3H), 3.73-3.65 (m, 4H), 3.61-

3.58 (m, 1H), 3.49 (t, J=9.1 Hz, 2H), 3.47-3.44 (m, 1H), 2.68 (d, J=3.3 Hz, 2H), 2.55-2.46 (m, 8H), 2.22 (d, J=6.6 Hz, 2H), 1.46-1.36 (m, 5H). $^{13}$C NMR (151 MHz, Methanol-d$_4$) δ 182.73, 177.42, 176.80, 101.09, 94.22, 86.19, 83.77, 80.98, 80.53, 80.17, 76.03, 75.60, 75.02, 72.64, 72.57, 65.09, 60.92, 58.57, 51.97, 51.83, 51.68, 51.54, 51.46, 51.40, 51.32, 51.26, 51.12, 38.77, 38.71, 28.82, 22.37, 22.24, 18.09, 18.03. High Resolution LC/MS (ESI-neg [M–H]$^-$= 330.11907, −1.13414 ppm)

A44: $^1$H NMR (600 MHz, Methanol-d$_4$) δ 5.44 (d, J=3.0 Hz, 1H), 4.65-4.61 (m, 3H), 4.60-4.57 (m, 2H), 4.52 (d, J=7.4 Hz, 1H), 4.48 (dd, J=7.6, 5.1 Hz, 2H), 4.31 (dd, J=7.8, 4.4 Hz, 2H), 3.84-3.80 (m, 1H), 3.77-3.73 (m, 2H), 3.72-3.66 (m, 3H), 3.57 (dd, J=10.9, 3.1 Hz, 1H), 3.50 (d, J=9.3 Hz, 1H), 3.46 (dd, J=11.1, 4.8 Hz, 1H), 3.21 (dt, J=10.1, 5.8 Hz, 2H), 2.92 (dd, J=12.7, 4.9 Hz, 2H), 2.69 (d, J=12.8 Hz, 1H), 2.28 (q, J=7.2 Hz, 3H), 1.72 (ddd, J=30.0, 14.1, 6.8 Hz, 6H), 1.60 (dq, J=14.7, 7.9 Hz, 2H), 1.47 (p, J=7.4 Hz, 4H), 1.40 (dd, J=10.0, 7.1 Hz, 4H). $^{13}$C NMR (151 MHz, Methanol-d$_4$) δ 179.00, 168.70, 94.19, 80.90, 76.02, 75.70, 65.84, 65.05, 64.17, 59.40, 58.56, 43.59, 39.49, 32.04, 29.20, 22.19.

A45: $^1$H NMR (400 MHz, Methanol-d$_4$) δ 5.41 (d, J=2.8 Hz, 1H), 4.56 (q, J=6.9 Hz, 2H), 4.50 (d, J=7.2 Hz, 1H), 3.76-3.70 (m, 3H), 3.69-3.62 (m, 3H), 3.58-3.51 (m, 2H), 3.51-3.43 (m, 3H), 2.97 (d, J=2.6 Hz, 1H), 2.84 (d, J=2.6 Hz, 1H), 2.66 (d, J=2.6 Hz, 1H), 2.25-2.11 (m, 3H), 1.96 (d, J=2.6 Hz, 1H), 1.61 (t, J=7.8 Hz, 2H), 1.37 (d, J=6.9 Hz, 3H), 0.99 (d, J=2.4 Hz, 3H). $^{13}$C NMR (101 MHz, Methanol-d$_4$) δ 177.46, 167.41, 94.14, 80.86, 80.22, 76.02, 75.60, 65.04, 58.63, 52.18, 51.97, 51.82, 51.75, 51.73, 51.61, 51.54, 51.49, 51.33, 51.26, 51.11, 50.90, 39.50, 34.21, 34.13, 28.84, 22.23, 22.13. High Resolution LC/MS (ESI-neg [M–H]$^-$=360.14157, 0.92350 ppm)

A49: $^1$H NMR (600 MHz, Methanol-d$_4$) δ 7.15 (t, J=9.7 Hz, 2H), 5.26 (d, J=2.3 Hz, 1H), 4.54 (q, J=6.5 Hz, 1H), 3.68-3.62 (m, 2H), 3.58 (dd, J=11.7, 5.2 Hz, 1H), 3.51-3.46 (m, 1H), 3.39 (t, J=9.4 Hz, 1H), 1.28 (d, J=6.0 Hz, 7H). $^{13}$C NMR (151 MHz, MeOD) δ 179.59, 178.21, 127.92, 111.03, 110.78, 110.67, 97.59, 90.36, 76.53, 76.19, 72.12, 72.04, 71.28, 61.15, 57.29, 54.91, 48.18, 48.03, 48.00, 47.89, 47.85, 47.75, 47.71, 47.61, 47.57, 47.47, 47.43, 47.33, 47.28, 47.18, 47.14, 21.96, 20.71, 20.67, 18.42, 18.22.

D1: $^1$H NMR (600 MHz, Deuterium Oxide) (Anomers—1.00α: 0.61β) δ 5.41 (d, J=3.5 Hz, 1H, α 1-H), 4.91 (d, J=8.4 Hz, 1H, β 1-H), 4.72 (q, J=6.9 Hz, 1H, β C—H), 4.67 (q, J=6.7 Hz, 1H, α C—H), 4.38-4.30 (m, 4H, α and β alanine C—H, α and β isoglutamine C—H), 3.89-3.84 (m, 2H, α 5-H, β 6-H), 3.82 (dd, J=12.3, 2.0 Hz, 1H, α 6-H), 3.76 (dd, J=12.3, 5.0 Hz, 1H, α 6'-H), 3.74-3.66 (m, 2H, α 3-H, β 6'-H), 3.64-3.58 (m, 2H, α 4-H, β 6-H), 3.56-3.51 (m, 1H, β 3-H), 3.48 (ddd, J=9.8, 5.6, 1.9 Hz, 1H, β 5-H), 3.30 (dd, J=10.4, 3.5 Hz, 1H, α 2-H), 3.01 (dd, J=10.4, 8.6 Hz, 1H, β 2-H), 2.53-2.43 (m, 4H, α and β isoglutamine methylene), 2.22-2.12 (m, 2H, α and β isoglutamine methylene), 2.04-1.94 (m, 2H, α and β isoglutamine methylene), 1.44-1.36 (m, 12H, α and β methyl, α and β alanine methyl). $^{13}$C NMR (151 MHz, Deuterium Oxide) δ 176.90 (carbonyl), 176.86 (carbonyl), 175.95 (carbonyl), 175.94 (carbonyl), 175.85 (carbonyl), 175.75 (carbonyl), 175.37 (carbonyl), 175.29 (carbonyl), 92.63 (β 1-C), 88.85 (α 1-C), 78.51 (β 3-C), 76.81 (α 3-C), 76.36 (α C—H), 76.02 (β C—H), 75.86 (β 5-H), 71.38 (α 5-C), 70.48 (β 4-C), 70.19 (α 4-C), 60.16 (β 6-C), 59.98 (α 6-C), 55.65 (β 2-C), 53.37 (α 2-C), 52.85 (α isoglutamine C—H), 52.78 (β isoglutamine C—H), 49.98 (α alanine C—H), 49.81 (β alanine C—H), 30.06 (α and β isoglutamine methylene), 26.11 (β isoglutamine methylene) 26.00 (α isoglutamine methylene) 18.99 (β methyl), 18.90 (α methyl), 16.50 (β alanine methyl), 16.40 (α alanine methyl). HRMS (ESI-Pos) for C$_{17}$H$_{30}$N$_4$O$_{10}$ (450.19619): 451.20347 [M+H]$^+$.

D2: $^1$H NMR (600 MHz, Methanol-d4) (Anomers—1.00α: 0.45β) δ 8.37 (d, J=7.8 Hz, 1H, α N—H), 8.28 (d, J=8.0 Hz, 1H, β N—H), 7.95 (d, J=5.9 Hz, 1H, α N—H), 7.87 (d, J=5.9 Hz, 1H, β N—H), 5.17 (d, J=3.3 Hz, 1H, α 1-H), 4.56 (d, J=8.3 Hz, 1H, β 1-H), 4.42-4.33 (m, 4H, α and β C—H, α and β isoglutamine methyne), 4.32-4.24 (m, 2H, α and β C—H alanine), 3.90-3.84 (m, 2H, α 2-H, β 6-H), 3.82-3.77 (m, 2H, α 5-H, α 6-H), 3.74-3.67 (m, 4H, α 6'-H, β 6'-H, β 2-H, β 4-H), 3.66-3.62 (dd, J=10.5, 8.9 Hz, 1H, α 3-H), 3.49 (t, J=9.4 Hz, 1H, α 4-H), 3.43 (t, J=9.2 Hz, 1H, β 3-H), 3.32-3.30 (m, 1H, β H-5), 2.40 (q, J=7.6 Hz, 4H, α and β isoglutamine methylene), 2.21 (ddd, J=21.0, 7.8, 4.8 Hz, 2H, α and β isoglutamine methylene), 1.96 (s, 3H β acetyl), 1.96 (s, 3H, α acetyl), 1.94-1.87 (m, 2H, α and β isoglutamine methylene), 1.44-1.34 (m, 16H, α and β methyl, α and β methyl alanine). $^{13}$C NMR (151 MHz, Methanol-d4) δ 176.57 (carbonyl), 176.39 (carbonyl), 176.35 (carbonyl), 176.26 (carbonyl), 176.18 (carbonyl), 176.16 (carbonyl), 175.32 (carbonyl), 174.32 (carbonyl), 173.45 (carbonyl), 173.44 (carbonyl), 97.24 (β 1-C), 92.47 (α 1-C), 83.40 (β 3-C), 80.35 (α 3-C), 78.40 (α methyl), 78.06 (β methyl), 77.88 (β 5-C), 73.26 (α 5-C), 71.68 (α 4-C), 71.32 (β 4-C), 62.75 (β 6-C), 62.67 (α 6-C), 58.07 ((β 2-C), 55.48 (α 2-C), 53.91 (α isoglutamine methyne), 53.76 (β isoglutamine methyne), 50.80 (α C—H alanine), 50.74 (β C—H alanine), 31.28 (α isoglutamine methylene), 31.26 (β isoglutamine methylene), 28.19 (α isoglutamine methylene), 27.99 (β isoglutamine methylene), 23.14 (β acetyl), 22.89 (α acetyl), 19.70 (α methyl), 19.59 (6 methyl), 17.76 (β methyl alanine), 17.66 (α methyl alanine). LRMS (ESI-Pos) for C$_{19}$H$_{32}$N$_4$O$_{11}$ (492.21): 493.20 [M+H]$^+$.

D9: $^1$H NMR (600 MHz, Methanol-d4) (Anomers—1.00α: 0.19β) δ 5.20 (d, J=3.4 Hz, 1H, α 1-H), 4.50 (q, J=6.7 Hz, 1H, α C—H), 4.29 (q, J=7.1 Hz, 1H, α alanine C—H), 4.22 (dd, J=9.0, 4.1 Hz, 1H, α isoglutamine methyne), 4.00 (s, 2H, α glycolyl methylene), 3.90 (dd, J=10.6, 3.4 Hz, 1H, α 2-H), 3.82 (dq, J=6.9, 2.1 Hz, 1H, α 5-H), 3.81-3.73 (m, 3H, α 3-H, 6-H, 6'-H), 3.55-3.46 (m, 1H, 4-H), 2.33-2.26 (m, 2H, α isoglutamine methylene), 2.15 (dtq, J=15.3, 7.6, 3.9 Hz, 1H, α isoglutamine methylene), 2.01-1.92 (m, 1H, α isoglutamine methylene), 1.39 (d, J=7.1 Hz, 3H, α alanine methyl), 1.38 (d, J=6.8 Hz, 3H, α methyl). $^{13}$C NMR (151 MHz, Methanol-d4) δ 179.01 (carbonyl), 174.93 (carbonyl), 174.43 (carbonyl), 173.46 (carbonyl), 173.43 (carbonyl), 90.40 (α 1-C), 77.57 (α 3-C), 75.76 (α C—H), 71.38 (α 5-C), 70.19 (α 4-C), 60.74 (α glycolyl methylene), 60.55 (α 6-C), 53.30 (α isoglutamine methyne), 53.04 (α 2-C), 48.84 (α alanine C—H), 32.81 (α isoglutamine methylene), 26.75 (α isoglutamine methylene), 17.75 (α methyl), 15.59 (α alanine methyl). LRMS (ESI-Neg) for C$_{19}$H$_{32}$N$_4$O$_{12}$ (508.20): 507.15 [M–H]$^-$.

D16: $^1$H NMR (600 MHz, Methanol-d4) (Anomers—1.00α: 0.33β) δ 5.35 (d, J=3.2 Hz, 1H, α 1-H), 4.66 (d, J=8.3 Hz, 1H, β 1-H), 4.55 (q, J=6.8 Hz, 1H, α C—H), 4.36 (dt, J=9.4, 4.2 Hz, 1H, β isoglutamine methyne), 4.33-4.28 (m, 2H, α alanine C—H, α isoglutamine methyne), 4.28-4.25 (m, 1H, β alanine C—H), 4.17 (q, J=6.9 Hz, 1H, β C—H), 3.88 (dd, J=11.9, 2.3 Hz, 1H, β 6-H), 3.86-3.82 (m, 1H, β 2-H), 3.82-3.77 (m, 3H, α 2-H, α 5-H, α 6-H), 3.75-3.70 (m, 3H, α 3-H, α 6'-H, β 6'-H), 3.52 (t, J=9.3 Hz, 1H, α 4-H), 3.50-3.46 (m, 2H, β 3-H, β 4-H), 3.36-3.31 (m, 1H, β 5-H), 2.51-2.34 (m, 4H, α and β isoglutamine methylene), 2.21 (ddt, J=15.9, 7.9, 4.8 Hz, 2H, α and β isoglutamine methylene), 1.98-1.86 (m, 2H, α and β isoglutamine methylene), 1.41-1.35 (m, 12H, α and β methyl, α and β methyl alanine). $^{13}$C NMR (151 MHz, Methanol-d4) δ 176.84 (carbonyl), 176.83 (carbonyl), 176.22 (carbonyl), 176.12 (carbonyl), 175.72 (carbonyl) 175.71 (carbonyl), 175.56 (carbonyl), 175.25 (carbonyl) 174.90 (carbonyl), 174.87 (carbonyl), 117.46 (q, J=287.0H, α and β CF$_3$) 96.26 (β 1-C), 91.35 (α 1-C), 83.42 (β 3-C), 78.74 (β C—H), 78.60 (α 3-C), 78.01 (β 5-C), 77.47 (α C—H), 73.39 (α 5-C), 72.03 (α 4-C), 70.75 (β 4-C), 62.68 (β 6-C), 62.36 (α 6-C), 58.26 (β 2-C), 56.49 (α 2-C), 53.95 (α isoglutamine methyne), 53.54 (β isoglutamine methyne), 50.83 (α alanine C—H), 50.61 (β alanine C—H), 31.18 (α isoglutamine methylene), 31.13 (β isoglutamine methylene), 28.05 (β isoglutamine methyne), 27.75 (α isoglutamine methylene), 19.95 (α methyl), 19.47 (β methyl), 17.51 (β alanine methyl), 17.33 (α alanine methyl). LRMS (ESI-Pos) for C$_{19}$H$_{29}$F$_3$N$_4$O$_{11}$ (546.18): 547.15 [M+H]$^+$.

D22: $^1$H NMR (600 MHz, Methanol-d4) (Anomers—1.00α: 0.15β) δ 5.26 (d, J=3.3 Hz, 1H, α 1-H), 4.60-4.48 (m, 2H, α acetoxycetic methylene, α C—H), 4.34 (dd, J=9.4, 4.7 Hz, 1H, α isoglutamine methyne), 4.31-4.25 (m, 1H, α alanine C—H), 3.84-3.76 (m, 3H, α 2-H, α 5-H, α 6-H), 3.72 (dd, J=11.8, 5.1 Hz, 1H, α 6'-H), 3.70-3.63 (m, 1H, α 3-H), 3.50 (t, J=9.4 Hz, 1H, α 4-H), 2.42 (t, J=7.5 Hz, 2H. α isoglutamine methylene), 2.21 (ddt, J=14.4, 7.7, 3.7 Hz, 1H, α isoglutamine methylene), 2.15 (s, 3H, α acetyl), 1.92 (ddt, J=12.5, 9.6, 6.3 Hz, 1H, α isoglutamine methylene), 1.39 (d, J=7.3 Hz, 3H, α alanine methyl), 1.37 (d, J=6.8 Hz, 3H, α methyl). $^{13}$C NMR (151 MHz, Methanol-d4) δ 176.67 (carbonyl), 176.49 (carbonyl), 176.25 (carbonyl), 175.57 (carbonyl), 172.01 (carbonyl), 170.47 (carbonyl), 92.07 (α 1-C), 79.14 (α 3-C), 77.65 (α C—H), 73.34 (α 5-C), 72.14 (α 4-C), 63.47 (α acetoxyacetic methylene), 62.51 (α 6-C), 55.63 (α 2-C), 53.99 (α isoglutamine methyne), 50.95 (α alanine C—H), 31.26 (α isoglutamine methylene), 27.86 (α isoglutamine methylene), 20.70 (α acetyl), 19.83 (α methyl), 17.52 (α alanine methyl). LRMS (ESI-Neg) for C$_{21}$H$_{34}$N$_4$O$_{13}$ (550.21): 549.10 [M–H]$^-$.

D23: $^1$H NMR (600 MHz, Methanol-d4) (Anomers—1.00α: 0.21β) δ 5.17 (d, J=3.3 Hz, 1H, α 1-H), 4.59 (d, J=8.3 Hz, 1H, β 1-H), 4.42 (q, J=6.6 Hz, 2H, α and β C—H), 4.37-4.32 (m, 2H, α and β isoglutamine methyne), 4.28 (q, J=7.0 Hz, 2H, α and β alanine C—H), 3.86 (dd, J=10.7, 3.3 Hz, 2H, α 2-H, β 6-H), 3.82-3.77 (m, 2H, α 5-H, α 6-H), 3.72 (dd, J=11.9, 5.2 Hz, 1H, α 6'-H), 3.70-3.68 (m, 2H, β 2-H, β 6'-H), 3.65 (dd, J=10.5, 8.9 Hz, 1H, α 3-H), 3.51-3.46 (m, 1H, α 4-H), 3.47-3.43 (m, 2H, β 3-H, β 4-H), 3.31 (m, 1H, β 5-H), 2.64-2.55 (m, 4H, α and β N-succinyl methylene), 2.55-2.46 (m, 4H, α and β N-succinyl methylene), 2.43-2.37 (m, 4H, α and β isoglutamine methylene), 2.26-2.16 (m 2H, α and β isoglutamine methylene), 1.97-1.88 (m, 2H, α and β isoglutamine methylene), 1.40 (d, J=7.2 Hz, 6H, α and β alanine methyl), 1.38 (d, J=6.8 Hz, 6H, α and β methyl). $^{13}$C NMR (151 MHz, Methanol-d4) δ 176.89 (carbonyl), 176.87 (carbonyl), 176.63 (carbonyl×2), 176.51 (carbonyl), 176.41 (carbonyl), 176.38 (carbonyl), 176.34 (carbonyl), 175.52 (carbonyl×2), 174.76 (carbonyl), 174.73 (carbonyl), 97.14 ((β 1-C), 92.47 (α 1-C), 82.91 (β 3-C), 79.91 (α 3-C), 78.07 (β C—H), 77.87 (β 5-C), 77.83 (α C—H), 73.25 (α 5-C), 71.71 (α 4-C), 71.29 (β 4-C), 62.76 (β 6-C), 62.64 (α 6-C), 58.22 (β 2-C), 55.51 (α 2-C), 54.05 (α isoglutamine methyne), 53.91 (β isoglutamine methyne), 50.91 (α alanine C—H), 50.86 (β alanine C—H), 32.07 (β succinyl methylene), 31.83 (α succinyl methylene), 31.60 (α isoglutamine methylene), 31.58 (β isoglutamine methylene), 30.38 (α succinyl methylene), 30.10 (β succinyl methylene), 27.97 (α isoglutamine methylene), 27.87 (β isoglutamine methylene), 19.61 (α methyl), 19.39 (β methyl), 17.61 (β alanine methyl), 17.52 (α alanine methyl). LRMS (ESI-Pos) for C$_{21}$N$_{34}$N$_4$O$_{13}$ (550.21): 551.20 [M+H]$^+$.

D24: $^1$H NMR (600 MHz, Methanol-d4) (Anomers—1.00α: 0.35β) δ 5.17 (d, J=3.3 Hz, 1H, α 1-H), 4.46 (q, J=6.7 Hz, 1H, α C—H), 4.31 (dd, J=9.3, 4.3 Hz, 1H, α isoglutamine methyne), 4.28 (q, J=7.0 Hz, 1H, α alanine C—H) 3.82 (dd, J=10.7, 3.4 Hz, 1H, α 2-H), 3.80-3.77 (m, 1H, α 5-H, α 6-H), 3.72 (dd, J=12.0, 5.2 Hz, 1H, α 6'-H), 3.69-3.65 (m, 1H, α 3-H), 3.50-3.46 (m, 1H, α 4-H), 2.76 (qq, J=13.2, 6.8 Hz, 2H, α levulinyl methylene), 2.47 (qq, J=13.6, 6.7 Hz, 2H, α levulinyl methylene), 2.41-2.35 (m, 2H, α isoglutamine methylene), 2.23-2.18 (m, 1H, α isoglutamine methylene), 2.16 (s, 3H, α levulinyl methyl), 1.97-1.90 (m, 1H, α isoglutamine methylene), 1.40 (d, J=7.1 Hz, 3H, α alanine methyl), 1.38 (d, J=6.7 Hz, 3H, α methyl). $^{13}$C NMR (151 MHz, Methanol-d4) δ 209.97 (carbonyl), 176.69 (carbonyl), 176.49 (carbonyl), 176.47 (carbonyl), 175.45 (carbonyl), 174.97 (carbonyl), 92.41 (α 1-C), 79.65 (α 3-C), 77.76 (a C—H), 73.26 (α 5-C), 71.91 (α 4-C), 62.63 (α 6-C), 55.57 (α 2-C), 54.34 (α isoglutamine methyne), 50.90 (α alanine C—H), 39.13 (α levulinyl methylene), 30.67 (α levulinyl methylene), 29.75 (α levulinyl methyl), 29.74 (a isoglutamine methylene), 28.16 (α isoglutamine methylene), 19.68 (α methyl), 17.54 (α alanine methyl). LRMS (ESI-Pos) for C$_{22}$H$_{36}$N$_4$O$_{12}$ (548.23): 549.20 [M+H]$^+$.

D25: $^1$H NMR (600 MHz, Methanol-d4) (Anomers—1.00α: 0.16β) δ 5.22 (d, J=3.4 Hz, 1H, α 1-H), 4.45 (q, J=6.8 Hz, 1H, α C—H), 4.32 (dd, J=9.3, 4.4 Hz, 1H, α isoglutamine), 4.30 (q, J=7.1, 6.5 Hz, 1H, α alanine C—H), 3.91 (d, J=15.9 Hz, 1H, α 2-azidoacetic acid methylene), 3.86 (d, J=16.0 Hz, 1H, α 2-azidoacetic acid methylene), 3.86 (dd, J=10.6, 3.3 Hz, 1H, α 2-H), 3.83-3.76 (m, 2H, α 5-H, α 6-H), 3.72 (dd, J=11.9, 5.2 Hz, 1H, α 6'-H), 3.70-3.65 (m, 1H, α 3-H), 3.53-3.46 (m, 1H, α 4-H), 2.46-2.32 (m, 2H, α isoglutamine methylene), 2.25-2.15 (m, 1H, α isoglutamine methylene), 1.98-1.88 (m, 1H, α isoglutamine methylene), 1.41 (d, J=7.1 Hz, 1H, α alanine methyl), 1.38 (d, J=6.7 Hz, 1H, α methyl). $^{13}$C NMR (151 MHz, Methanol-d4) δ 175.14 (carbonyl), 174.60 (carbonyl), 174.39 (carbonyl), 173.53 (carbonyl), 168.47 (carbonyl), 90.21 (α 1-C), 77.70 (α 3-C), 75.90 (α C—H), 71.33 (α 5-C), 69.96 (α 4-C), 60.55 (α 6-C), 53.68 (α 2-C), 52.19 (α isoglutamine methyne), 51.00 (α 2-azidoacetic acid methylene), 48.88 (α alanine C—H), 29.82 (α isoglutamine methylene), 26.03 (α isoglutamine methylene), 17.80 (α methyl), 15.54 (α alanine methyl). LRMS (ESI-Pos) for C$_{19}$H$_{31}$N$_7$O$_{11}$ (533.21): 534.20 [M+H]$^+$. IR (ATR probe): Azide-2114.74 cm$^{-1}$ (medium).

D29: $^1$H NMR (600 MHz, Methanol-d4) δ 8.54 (d, J=8.6 Hz, 1H, aromatic), 8.50 (d, J=8.7 Hz, 1H, aromatic), 8.29 (d, J=6.3 Hz, 1H, aromatic), 7.64-7.60 (m, 1H, aromatic), 7.59-7.55 (m, 1H, aromatic), 7.41 (d, J=7.6 Hz, 1H, aromatic), 4.89 (d, J=3.2 Hz, 1H, α 1-H), 4.47 (q, J=7.0 Hz, 1H, α C—H), 4.35-4.29 (m, 2H, α alanine methyl, α isoglutamine methyne), 3.68-3.64 (m, 2H, α 5-H, α 6-H), 3.63-3.59 (m, 1H, α 6'-H), 3.47 (dd, J=10.3, 8.8 Hz, 1H, α 3-H), 3.25 (t, J=9.2 Hz, 1H, α 4-H), 2.98 (s, 6H, N-methyl), 2.95 (dd, J=10.4, 3.2 Hz, 1H, α 2-H), 2.49-2.42 (m, 2H, α isoglutamine methylene), 2.32-2.22 (m, 1H, α isoglutamine methylene), 2.02-1.92 (m, 1H, α isoglutamine methylene), 1.43 (d, J=7.1 Hz, 3H, α alanine methyl), 0.93 (d, J=6.8 Hz, 3H, methyl). $^{13}$C NMR (151 MHz, Methanol-d4) δ 177.13 (carbonyl), 176.42 (carbonyl), 176.41 (carbonyl), 176.00 (carbonyl), 137.02 (aromatic), 130.97 (aromatic), 130.63 (aromatic), 130.52 (aromatic), 130.39 (aromatic), 130.38 (aromatic), 128.80 (aromatic), 124.84 (aromatic), 117.13

(aromatic), 114.04 (aromatic), 93.12 (α 1-C), 78.31 (α 3-C), 77.09 (α C—H), 73.06 (α 5-C), 72.66 (α 4-C), 62.21 (α 6-C), 59.10 (α 2-C), 54.34 (α isoglutamine methylene), 51.27 (α alanine C—H), 46.17 (α N-methyl), 31.48 (α isoglutamine methylene), 27.61 (α isoglutamine methylene), 19.33 (α methyl), 17.10 (α alanine methyl). LRMS (ESI-Pos) for $C_{29}H_{41}N_5O_{12}S$ (683.25): 684.20 [M+H]$^+$.

D44: $^1$H NMR (600 MHz, Methanol-d4) (Anomers— 1.00α: 0.21β) δ 5.21 (d, J=3.4 Hz, 1H, α 1-H), 4.50 (dd, J=7.7, 5.0 Hz, 1H, α 9-position), 4.45 (q, J=6.7 Hz, 1H, α C—H), 4.37-4.26 (m, 3H, α 10-position biotin, α isoglutamine methyne, a alanine C—H), 3.84 (dd, J=10.7, 3.4 Hz, 1H, α 2-H), 3.79 (m, 3H, α 5-H, α 6-H), 3.72 (dd, J=11.6, 5.0 Hz, 1H, α 6'-H), 3.65 (dd, J=10.5, 8.9 Hz, 1H, α 3-H), 3.53-3.46 (m, 1H, α 4-H), 3.24-3.18 (m, 1H, α 6-position biotin), 2.93 (dd, J=12.7, 5.0 Hz, 1H, α 8-position biotin), 2.72-2.67 (m, 1H, α 8-position biotin), 2.44-2.37 (m, 2H, α isoglutamine methlene), 2.24 (t, J=7.5 Hz, 2H, α 2-position biotin), 2.22-2.18 (m, 1H, α isoglutamine methylene), 1.92 (dtd, J=14.3, 8.8, 8.1, 4.6 Hz, 1H, isoglutamine methylene), 1.77-1.56 (m, 4H, α 3-position biotin, α 5-position biotin), 1.48-1.42 (m, 2H, α 4-position biotin), 1.40 (d, J=7.1 Hz, 3H, α alanine methyl), 1.38 (d, J=6.8 Hz, 3H, α methyl). $^{13}$C NMR (151 MHz, Methanol-d4) δ 176.68 (carbonyl), 176.58 (carbonyl), 176.29 (carbonyl), 176.24 (carbonyl), 175.45 (carbonyl), 166.16 (carbonyl), 92.40 (α 1-C), 79.60 (α 3-C), 77.72 (α C—H), 73.26 (α 5-C), 71.81 (α 4-C), 63.32 (α 10-position biotin), 62.61 (α 6-C), 61.65 (α 9-position biotin), 56.90 (α 6-position biotin), 55.53 (α 2-C), 54.00 (α isoglutamine methyne), 50.88 (α alanine C—H), 41.05 (α 8-position biotin), 36.95 (α 2-position biotin), 31.38 (α isoglutamine methylene), 29.71 (α 4-position biotin), 29.40 (α 3-position biotin), 28.00 (a isoglutamine methylene), 26.71 (α 5-position methylene), 19.73 (α methyl), 17.57 (a alanine methyl). LRMS (ESI-Pos) for $C_{27}H_{44}N_6O_{12}S$ (676.27): 677.20 [M+H]$^+$.

U2: $^1$H NMR (600 MHz, Methanol-d4) (Anomers— 1.00α: 0.15β) δ 8.46 (d, J=8.5 Hz, 1H, aromatic), 8.26 (d, J=8.6 Hz, 1H, aromatic), 8.10 (d, J=8.1 Hz, 1H, aromatic), 7.56-7.45 (m, 2H, aromatic), 7.22 (d, J=7.5 Hz, 1H, aromatic), 5.06 (d, J=3.4 Hz, 1H, α 1-H), 4.29 (q, J=6.7 Hz, 1H, α C—H), 4.22-4.13 (m, 2H, α alanine C—H, α isoglutamine methyne), 3.77 (dd, J=10.6, 3.4 Hz, 1H, α 2-H), 3.72-3.66 (m, 2H, α 5-H, α 6-H), 3.61 (dd, J=11.9, 5.3 Hz, 1H, α 6'-H), 3.54 (dd, J=10.5, 8.9 Hz, 1H, α 3-H), 3.41-3.36 (m, 1H, α 4-H), 3.12 (dt, J=12.3, 6.1 Hz, 1H, α ethylene linker methylene), 3.06 (dt, J=13.5, 6.2 Hz, 1H, α ethylene linker methylene), 2.84 (t, J=6.2 Hz, 2H, α ethylene linker methylene), 2.82 (s, 6H, α N-methyl), 2.10-1.98 (m, 3H, α isoglutamine methylene, α isoglutamine methylene), 1.85 (s, 2H, acetyl), 1.78-1.70 (m, 1H, α isoglutamine methylene), 1.30 (d, J=7.2 Hz, 3H, α Alanine methyl), 1.29 (d, J=6.8 Hz, 3H, α methyl). $^{13}$C NMR (151 MHz, Methanol-d4) δ 176.65 (carbonyl), 176.21 (carbonyl), 175.26 (carbonyl), 175.15 (carbonyl), 173.43 (carbonyl), 136.88 (aromatic), 131.04 (aromatic), 131.01 (aromatic), 130.86 (aromatic), 130.29 (aromatic), 130.28 (aromatic), 129.18 (aromatic), 124.52 (aromatic), 120.90 (aromatic), 116.69 (aromatic), 92.44 (α 1-C), 80.37 (α 3-C), 78.09 (α C—H), 73.26 (α 5-C), 71.59 (α 4-C), 62.63 (α 6-C), 55.50 (α 2-C), 53.87 (a isoglutamine methyne), 50.91 (α alanine C—H), 45.91 (N-methyl), 43.14 (α ethylene linker methylene), 40.62 (α ethylene linker methylene), 32.99 (α isoglutamine methylene), 28.55 (α isoglutamine methylene), 22.91 (a acetyl), 19.70 (α methyl), 17.63 (α alanine methyl). LRMS (ESI-Pos) for $C_{33}H_{49}N_7O_{12}S$ (767.32): 768.25 [M+H]$^+$.

U9: $^1$H NMR (600 MHz, Methanol-d4) (Anomers— 1.00α: 0.27β) δ 8.57 (d, J=8.5 Hz, 1H, aromatic), 8.33 (d, J=8.6 Hz, 1H, aromatic), 8.19 (d, J=7.2 Hz, 1H, aromatic), 7.59 (q, J=7.9 Hz, 2H, aromatic), 7.28 (d, J=7.5 Hz, 1H, aromatic), 5.16 (d, J=3.2 Hz, 1H, α 1-H), 4.40 (q, J=6.7 Hz, 1H, α C—H), 4.31-4.24 (m, 2H, α alanine C—H, α isoglutamine methyne), 3.99 (s, 1H, α glycolyl methylene), 3.96 (dd, J=10.5, 3.2 Hz, 1H, α 2-H), 3.84-3.77 (m, 2H, α 5-H, α 6-H), 3.73 (dd, J=11.9, 5.1 Hz, 1H, α 6'-H), 3.71-3.67 (m, 1H, α 3-H), 3.51 (t, J=9.4 Hz, 1H, α 4-H), 3.19-3.11 (m, 2H, α ethylene linker methylene), 2.94 (t, J=6.1 Hz, 2H, α ethylene linker methylene), 2.88 (s, 6H, α N-methyl), 2.20-2.10 (m, 3H, α isoglutamine methylene, α isoglutamine methylene), 1.91-1.82 (m, 1H, α isoglutamine methylene), 1.40 (d, J=7.1 Hz, 3H, α Alanine methyl), 1.38 (d, J=6.8 Hz, 3H, α methyl). $^{13}$C NMR (151 MHz, Methanol-d4) δ 178.80 (carbonyl), 176.41 (carbonyl), 175.35 (carbonyl), 175.19 (carbonyl), 175.15 (carbonyl), 136.77 (aromatic), 131.26 (aromatic), 131.25 (aromatic), 130.88 (aromatic), 130.23 (aromatic), 129.85 (aromatic), 129.20 (aromatic), 124.32 (aromatic), 120.46 (aromatic), 116.48 (aromatic), 92.49 (α 1-C), 80.21 (α 3-C), 77.92 (α C—H), 73.32 (α 5-C), 71.68 (α 4-C), 62.73 (a glycolyl methylene), 62.58 (α 6-C), 54.88 (α 2-C), 53.89 (α isoglutamine methyne), 50.97 (α alanine C—H), 45.81 (N-methyl), 43.15 (α ethylene linker methylene), 40.63 (α ethylene linker methylene), 33.01 (α isoglutamine methylene), 27.13 (α isoglutamine methylene), 19.63 (α methyl), 17.54 (α alanine methyl). LRMS (ESI-Pos) for $C_{33}H_{49}N_7O_{13}S$ (783.31): 784.30 [M+H]$^+$.

D53: $^1$H NMR (600 MHz, Methanol-d4) (Anomers— 1.00α: 0.31β) δ 5.20 (d, J=3.1 Hz, 1H, α 1-H), 4.66 (d, J=8.3 Hz, 1H, (β 1-H), 4.46-4.41 (m, 2H, α and β C—H), 4.33 (dd, J=9.6, 4.6 Hz, 2H, α and β isoglutamine methyne), 4.29-4.24 (m, 2H, α and β alanine C—H), 3.95-3.86 (m, 5H, α 2-H, α 5-H, β 6-H, α and β methoxyacetic methylene), 3.83-3.77 (m, 2H, α 6-H, β 2-H), 3.73 (dd, J=11.9, 5.2 Hz, 1H, α 6'-H), 3.71-3.66 (m, 2H, α 3-H, β 6'-H), 3.58-3.53 (m, 1H, (β 3-H), 3.50 (t, J=9.4 Hz, 1H, α 3-H), 3.45 (t, J=9.2 Hz, 1H, β 4-H), 3.41 (s, 6H, α and β O-methyl), 3.35-3.32 (m, 1H, β 5-H), 2.41 (td, J=14.2, 12.3, 7.9 Hz, 4H, α and β isoglutamine methylene), 2.21 (ddt, J=15.6, 7.9, 4.8 Hz, 2H, α and β isoglutamine methylene), 1.96-1.88 (m, 2H, α and β isoglutamine methylene), 1.39 (d, J=7.2 Hz, 6H α and β alanine methyl), 1.38 (d, J=6.9 Hz, 6H, α and β methyl). $^{13}$C NMR (151 MHz, Methanol-d4) δ 176.44 (carbonyl), 176.39 (carbonyl), 176.34 (carbonyl), 175.96 (carbonyl), 175.53 (carbonyl), 175.17 (carbonyl), 174.84 (carbonyl), 173.94 (carbonyl), 173.48 (carbonyl), 172.78 (carbonyl), 96.70 (β 1-C), 92.33 (α 1-C), 83.29 (β 3-C), 79.78 (α 3-C), 78.52 (β 5-C), 77.88 (β C—H), 77.84 (α C—H), 73.33 (α 5-C), 72.89 (β methoxyacetic methylene), 72.70 (a methoxyacetic methylene), 71.85 (α 4-C), 71.15 (β 4-C), 62.80 (β 6-C), 62.55 (α 6-C), 59.71 (α O-methyl), 59.63 (β O-methyl), 57.64 (β 2-C), 55.06 (α 2-C), 54.01 (α isoglutamine methyne), 53.80 (β isoglutamine methyne), 50.83 (α alanine C—H), 50.71 (β alanine C—H), 31.30 (α isoglutamine methylene), 31.26 (β isoglutamine methyne), 27.87 (α isoglutamine methyne), 27.83 (β isoglutamine methyne), 19.78 (α methyl), 19.51 (β methyl), 17.73 (α alanine methyl), 17.52 (β alanine methyl). LRMS (ESI-Pos) for $C_{20}H_{34}N_4O_{12}$ (522.22): 523.25 [M+H]$^+$.

(R)-methyl 5-amino-4-((S)-2-((R)-2-(((2S,4aR,6S, 7R,8R,8aS)-7-azido-6-(benzyloxy)-2-phenylhexahydropyrano[3,2-d][1,3]dioxin-8-yl)oxy)propanamido) propanamido)-5-oxopentanoate (I9)

I7 (530.0 mg, 0.980 mmol) dissolved in 31 mL methanol. Subsequently solution 8.84 mL 0.5M potassium hydroxide added and reaction monitored by TLC (7% methanol/dichloromethane) until complete. The reaction was quenched with Amberlite IR120, H form ion exchange resin, filtered and evaporated, then further dried under vacuum to yield a white solid (quantitative). (250.0 mg, 0.475 mmol) dissolved in 22 mL of anhydrous N,N-dimethylformamide under nitrogen. 1-Hydroxybenzotriazole hydrate (wetted with not less than 20 wt % water) (96.2 mg, 0.570 mmol), 2,4,6-collidine (188.2 µL, 1.42 mmol) and then 1-ethyl-3-(3-dimethylaminopropyl)carbodiimide (136.5 mg, 0.712 mmol) were subsequently added and the reaction was allowed to stir for 2 mins before D-γ-methyl isoglutamine hydrochloride (186.7 mg, 0.950 mmol) was added. The reaction stirred 18 hrs and was quenched with water and then diluted with ethyl acetate. The phases were separated and the organic phase was washed with 1 N hydrochloride, saturated sodium bicarbonate, brine and was dried with sodium sulfate. The organic phase was evaporated and the residue purified by column chromatography (5% methanol/dichloromethane). White powder (287.7 mg, 91% yield). $^1$H NMR (600 MHz, Chloroform-d) (Anomers—1.00 α: 0.51 β) δ 7.87 (d, J=6.0 Hz, 1H, β alanine N—H), 7.68 (d, J=6.2 Hz, 1H, α alanine N—H), 7.51-7.30 (m, 20H, aromatic), 7.26-7.18 (m, 2H, α and β isoglutamine N—H), 5.56 (s, 1H, β 4,6-benzylidene C—H), 5.55 (s, 1H, α 4,6-benzylidene C—H), 5.11 (d, J=3.7 Hz, 1H, α 1-H), 4.95 (d, J=11.5 Hz, 1H, β benzyl methylene), 4.77 (d, J=11.8 Hz, 1H, α benzyl methylene), 4.71 (d, J=11.5 Hz, 1H, β benzyl methylene), 4.62 (d, J=11.8 Hz, 1H, α benzyl methylene), 4.57 (d, J=8.0 Hz, 1H, β 1-H), 4.46 (td, J=8.2, 4.6 Hz, 2H, α and β isoglutamine C—H), 4.38 (dd, J=10.6, 5.0 Hz, 1H, β 6-H), 4.36-4.25 (m, 4H, α and β C—H, α and β alanine C—H), 4.24 (dd, J=10.3, 4.9 Hz, 1H, α 6-H), 3.93 (t, J=9.6 Hz, 1H, α 3-H), 3.89 (dt, J=9.9, 5.0 Hz, 1H, α 5-H), 3.82 (t, J=10.3 Hz, 1H, β 6'-H), 3.75 (t, J=10.3 HZ, 1H, α 6'-H), 3.69-3.67 (m, 1H, β 4-H), 3.66 (s, 6H, α and β methyl ester), 3.61 (t, J=9.3 Hz, 1H, α 4-H), 3.54 (dd, J=9.8, 8.1 Hz, 1H, β 2-H), 3.44-3.34 (m, 3H, α 2-H, β 5-H, β 3-H), 2.58-2.48 (m, 2H, α and β isoglutamine methylene), 2.45-2.37 (m, 2H, α and β isoglutamine methylene), 2.25-2.14 (m, 2H, α and β isoglutamine methylene), 2.05-1.96 (m, 2H, α and β isoglutamine methylene), 1.43 (d, J=7.0 Hz, 3H, α alanine methyl), 1.43 (d, J=6.9 Hz, 3H, β alanine methyl), 1.38 (d, J=6.8 Hz, 6H, α and β methyl). $^{13}$C NMR (151 MHz, Chloroform-d) δ 174.40 (carbonyl), 174.39 (carbonyl), 174.33 (carbonyl), 174.15 (carbonyl), 173.33 (carbonyl), 173.32 (carbonyl), 172.37 (carbonyl), 172.36 (carbonyl), 136.87 (aromatic), 136.78 (aromatic), 136.16 (aromatic ×2), 129.38 (aromatic), 129.36 (aromatic), 128.78 (aromatic), 128.74 (aromatic), 128.55 (aromatic), 128.53 (aromatic), 128.52 (aromatic ×2), 128.48 (aromatic), 128.36 (aromatic), 125.98 (aromatic), 125.93 (aromatic), 101.79 (α 4,6-benzylidene C—H), 101.68 (β 4,6-benzylidene C—H), 101.44 (β 1-C), 96.97 (α 1-C), 82.68 (α 4-C), 82.08 (β 4-C), 78.25 (β 3-C), 78.22 (α C—H), 77.90 (β C—H), 76.44 (α 3-C), 71.70 (β benzyl methylene), 70.20 (a benzyl methylene), 68.85 (α 6-C), 68.60 (β 6-C), 66.20 20 (β 5-C), 65.16 (β 2-C), 62.86 (α 5-C), 62.56 (α 2-C), 52.56 (α isoglutamine C—H), 52.50 (β isoglutamine C—H), 52.09 (a methyl ester), 52.08 (β methyl ester), 49.69 (α and β alanine C—H), 30.52 (β isoglutamine methylene), 30.51 (α isoglutamine methylene), 26.91 (β isoglutamine methylene), 26.80 (α isoglutamine methylene), 19.73 (α methyl), 19.57 (β methyl), 17.05 (β alanine methyl), 16.96 78 (α alanine methyl). LRMS (ESI-Pos) for $C_{32}H_{40}N_6O_{10}$ (668.28): 669.25 [M+H]$^+$.

(R)-methyl 5-amino-4-((S)-2-((R)-2-(((2S,3R,4R,5S,6R)-3-azido-2-(benzyloxy)-5-hydroxy-6-(hydroxymethyl)tetrahydro-2H-pyran-4-yl)oxy)propanamido)propanamido)-5-oxopentanoate (I10)

I9 (423.0 mg, 0.633 mmol) suspended in 25 mL of methanol. Amberlite IR120, H form ion exchange resin added and reaction refluxed at 60° C. for 4 hrs. Reaction determined complete by TLC (10% methanol/dicholoromethane) and cooled to room temperature. Reaction filtered and solvent evaporated to yield an oil which was purified by column chromatography (10% methanol/dichloromethane). White powder (263.7 mg, 72% yield). $^1$H NMR (600 MHz, Methanol-d4) (Anomers—1.00 α: 0.46 β) δ 7.41 (m, 4H, aromatic), 7.38-7.32 (m, 4H, aromatic), 7.33-7.27 (m, 2H, aromatic), 5.11 (d, J=3.5 Hz, 1H, α 1-H), 4.96 (d, J=11.7 Hz, 1H, β benzyl methylene), 4.78 (d, J=11.8 Hz, 1H, α benzyl methylene), 4.72 (d, J=11.7 Hz, 1H, β benzyl methylene), 4.59 (d, J=11.8 Hz, 1H, α benzyl methylene), 4.53 (d, J=8.1 Hz, 1H, (β 1-H), 4.44 (q, J=6.9 Hz, 1H, β C—H), 4.42-4.34 (m, 5H, α C—H, α and β alanine C—H, α and β isoglutamine C—H), 3.89 (dd, J=12.0, 2.2 Hz, 1H, β 6-H), 3.81 (dd, J=11.9, 2.2 Hz, 1H, α 6-H), 3.73-3.68 (m, 2H, α and β 6'-H), 3.68-3.65 (m, 7H, α and β methyl ester, α 3-H), 3.64 (td, J=4.9, 1.9 Hz, 1H, α 5-H), 3.53-3.48 (m, 2H, α and β 4-H), 3.46-3.40 (m, 2H, α and β 2-H), 3.28 (ddd, J=9.8, 5.6, 2.2 Hz, 1H, β 5-H), 3.18 (dd, J=9.9, 8.9 Hz, 1H, (β 3-H), 2.41 (t, J=7.6 Hz, 4H, α and β isoglutamine methyne), 2.25-2.17 (m, 2H, α and β isoglutamine methyne), 1.95-1.84 (m, 2H, α and β isoglutamine methyne), 1.44-1.39 (m, 12H, α and β methyl, a and alanine methyl). $^{13}$C NMR (151 MHz, Methanol-d4) δ 176.16 (carbonyl), 176.09 (carbonyl ×2), 176.07 (carbonyl), 175.02 (carbonyl), 175.01 (carbonyl), 174.80 (carbonyl ×2), 138.47 (aromatic), 138.42 (aromatic), 129.45 (aromatic), 129.40 (aromatic), 129.35 (aromatic), 129.20 (aromatic), 128.99 (aromatic), 128.95 (aromatic), 102.04 (β 1-C), 97.70 (α 1-C), 83.25 (β 3-C), 80.80 (α 3-C), 78.94 (β C—H), 78.89 (α C—H), 77.92 (β 5-C), 74.26 (α 5-C), 71.95 (β benzyl methylene), 71.92 (α 4-C), 71.83 (β 4-C), 70.42 (a benzyl methylene), 66.74 (β 2-C), 63.85 (α 2-C), 62.34 (β 6-C), 62.19 (α 6-C), 53.56 (α isoglutamine C—H), 53.49 (β isoglutamine C—H), 52.21 (α and β methyl ester), 50.51 (α alanine C—H), 50.49 (β alanine C—H), 31.12 (α isoglutamine methylene), 31.10 (β isoglutamine methylene), 28.10 (β isoglutamine methylene), 28.03 (α isoglutamine methylene), 19.81 (α methyl), 19.70 (β methyl), 18.16 (β alanine methyl), 18.02 (α alanine methyl). LRMS (ESI-Pos) for $C_{25}H_{36}N_6O_{10}$ (580.25): 581.20 [M+H]$^+$.

((R)-methyl 4-((S)-2-((R)-2-(((2R,3S,4R,5R,6S)-3-acetoxy-2-(acetoxymethyl)-5-azido-6-(benzyloxy)tetrahydro-2H-pyran-4-yl)oxy)propanamido)propanamido)-5-amino-5-oxopentanoate (I11)

I10 (245.0 mg, 0.422 mmol) dissolved in pyridine (2.45 mL) and acetic anhydride (2.45 mL) and stirred for 6 hrs under nitrogen. The reaction was subsequently evaporated and the residue was dissolved in dichloromethane and washed with 1 N hydrochloride (×2), saturated sodium bicarbonate and was dried with sodium sulfate. The organic phase was evaporated and the residue purified by column chromatography (5% methanol/dichloromethane). White powder (260.1 mg, 93% yield). $^1$H NMR (600 MHz, Methanol-d4) (Anomers—1.00 α: 0.42 β) δ 7.42-7.28 (m, 8H, aromatic), 5.15 (d, J=3.6 Hz, 1H α 1-H), 5.06-4.99 (m, 2H, α and β 4-H), 4.91 (d, J=11.7 Hz, 1H, β benzyl methylene), 4.75 (d, J=11.8 Hz, 1H, α benzyl methylene), 4.71 (d, J=11.7 Hz, 1H, β benzyl methylene), 4.62 (d, J=11.8 Hz, 1H, α benzyl methylene), 4.59 (d, J=8.1 Hz, 1H, β 1-H), 4.42-4.33 (m, 4H, α and β alanine C—H, α and β isoglutamine C—H), 4.26 (dd, J=12.3, 4.8 Hz, 1H, β 6-H), 4.20 (dd, J=12.3, 4.7 Hz, 1H, α 6-H), 4.18-4.13 (m, 2H, α and β C—H), 4.11 (dd, J=12.3, 2.3 Hz, 1H, β 6'-H), 4.02 (dd, J=12.3, 2.4 Hz, 1H, α 6'-H), 3.96 (ddd, J=10.2, 4.6, 2.5 Hz, 1H, α 5-H), 3.92-3.85 (m, 1H, α 3-H), 3.70 (ddd, J=10.0, 4.7, 2.5 Hz, 1H, β 5-H), 3.66 (s, 6H, α and β methyl ester), 3.65-3.61 (m, 2H, α and β 2-H), 3.52 (t, J=9.5 Hz, 1H, β 3-H), 2.41 (t, J=7.6 Hz, 4H, α and β isoglutamine methylene), 2.26-2.16 (m, 2H, α and β isoglutamine methylene), 2.11 (s, 3H, α acetyl), 2.10 (s, 3H, β acetyl), 2.07 (s, 3H, β acetyl), 2.05 (s, 3H, α acetyl), 1.96-1.85 (m, 2H, α and β isoglutamine methylene), 1.42 (d, J=7.1 Hz, 3H β alanine methyl), 1.41 (d, J=7.1 Hz, 3H, α alanine methyl), 1.31 (d, J=6.8 Hz, 3H, α alanine methyl), 1.29 (d, J=6.9 Hz, 3H, β methyl). $^{13}$C NMR (151 MHz, Methanol-d4) δ 176.03 (carbonyl), 176.00 (carbonyl), 175.42 (carbonyl), 175.23 (carbonyl), 174.86 (carbonyl), 174.85 (carbonyl), 174.80 (carbonyl), 174.79 (carbonyl), 172.35 (carbonyl), 172.34 (carbonyl), 171.50 (carbonyl), 171.45 (carbonyl), 138.18 (aromatic), 138.08 (aromatic), 129.56 (aromatic), 129.46 (aromatic ×2), 129.24 (aromatic), 129.20 (aromatic), 129.07 (aromatic), 101.93 (β 1-C), 97.79 (α 1-C), 81.20 (β 3-C), 79.55 (β C—H), 79.29 (α C—H), 78.80 (α 3-C), 72.94 (β 5-C), 72.25 (β benzyl methylene), 71.46 (α 4-C), 71.14 (β 4-C), 71.01 (α benzyl methylene), 69.39 (α C-5), 67.08 (β C-2), 64.21 (α C-2), 63.40 (α 6-C), 63.28 (β C-6), 53.52 (α isoglutamine C—H), 53.46 (β isoglutamine C—H), 52.22 (α and β methyl ester), 50.61 (α alanine C—H), 50.57 (β alanine C—H), 31.11 (α isoglutamine methylene), 31.09 (β isoglutamine methylene), 28.08 (β isoglutamine methylene), 28.01 (α isoglutamine methylene), 20.94 (α acetyl), 20.91 (β acetyl), 20.69 (α and β acetyl), 19.70 (α methyl), 19.59 (β methyl), 18.11 (β alanine methyl), 17.96 (α alanine methyl). LRMS (ESI-Pos) for C$_{29}$H$_{40}$N$_6$O$_{12}$ (664.27): 665.25 [M+H]+.

(R)-methyl 4-((S)-2-((R)-2-(((2R,3S,4R,5R,6S)-3-acetoxy-2-(acetoxymethyl)-5-amino-6-hydroxytetrahydro-2H-pyran-4-yl)oxy)propanamido)propanamido)-5-amino-5-oxopentanoate (I12)

I11 (130.0 mg, 0.196 mmol) dissolved in 6.4 mL water, 4.8 mL methanol and 0.80 mL acetic acid with stirring. 10% palladium on carbon (60.0 mg, 0.054 mmol) added and the reaction was degassed and stirred under hydrogen for 20 hrs. The reaction was monitored by mass-spectrometry and filtered through celite upon completion. Purified by HPLC (5% acetonitrile in water with 0.1% trifluoroacetic acid 10 min isocratic flow then 15 min gradient to 95% acetonitrile in water with 0.1% trifluoroacetic acid—5 mL/min). White solid (quantitative yield). $^1$H NMR (600 MHz, Methanol-d4) (Anomers—1.00 α: 0.32 β) δ 5.35 (d, J=3.6 Hz, 1H, α 1-H), 5.05-4.98 (m, 2H, α and (β 4-H), 4.93 (d, J=8.3 Hz, 1H, β 1-H), 4.41 (q, J=7.1 Hz, 1H, β alanine C—H), 4.38-4.31 (m, 4H, α and β C—H, α and β isoglutamine C—H), 4.26-4.21 (m, 2H, α and β 6-H), 4.15 (ddd, J=10.2, 4.6, 2.5 Hz, 1H, α 5-H), 4.07 (dd, J=12.3, 2.4 Hz, 1H, β 6'-H), 4.03 (dd, J=12.3, 2.4 Hz, 1H, α 6'-H), 3.91-3.86 (m, 1H, α 3-H), 3.76 (ddd, J=10.0, 4.8, 2.4 Hz, 1H, β 5-H), 3.69 (m, 7H, α and β methyl ester, β 3-H) 3.31-3.28 (m, 1H, α 2-H), 2.98 (dd, J=10.6, 8.4 Hz, 1H, β 2-H), 2.49-2.38 (m, 4H, α and β isoglutamine methylene), 2.23-2.18 (m, 2H, α and β isoglutamine methylene), 2.17 (s, 3H, α acetyl), 2.17 (s, 3H, β acetyl), 2.03 (s, 3H, β acetyl), 2.03 (s, 3H, α acetyl), 2.00-1.91 (m, 2H, α and β isoglutamine methylene), 1.38 (d, J=7.2 Hz, 3H, α alanine methyl), 1.37 (d, J=7.2 Hz, 3H, β alanine methyl), 1.32 (d, J=6.8 Hz, 6H, α and β methyl). $^{13}$C NMR (151 MHz, Methanol-d4) δ 176.54 (carbonyl), 176.44 (carbonyl), 176.08 (carbonyl), 175.99 (carbonyl), 175.28 (carbonyl), 175.27 (carbonyl), 174.93 (carbonyl), 174.87 (carbonyl), 172.36 (carbonyl), 172.30 (carbonyl), 171.30 (carbonyl), 171.25 (carbonyl), 94.79 (β 1-C), 90.53 (α 1-C), 78.12 (β 3-C), 77.23 (α C—H), 77.03 (β C—H), 76.69 (α 3-C), 72.91 (β 5-C), 72.56 (β 4-C), 72.49 (α 4-C), 68.55 (α 5-C), 63.26 (α 6-C), 63.16 (β 6-C), 57.63 (β 2-C), 55.31 (α 2-C), 53.76 (α isoglutamine C—H), 53.71 (β isoglutamine C—H), 52.29 (α and β methyl ester), 50.94 (α alanine C—H), 50.48 (β alanine C—H), 31.11 (α and β isoglutamine methylene), 28.37 (β isoglutamine methylene), 28.08 (α isoglutamine methylene), 20.80 (α acetyl), 20.74 (β acetyl), 20.62 (α acetyl), 20.61 (β acetyl), 20.25 (α methyl), 20.13 (β methyl), 17.46 (α alanine methyl), 16.94 (β alanine methyl). LRMS (ESI-Pos) for C$_{22}$H$_{36}$N$_4$O$_{12}$ (548.23): 549.20 [M+H]+.

(R)-methyl 4-((S)-2-((R)-2-(((2R,3S,4R,5R,6S)-3-acetoxy-2-(acetoxymethyl)-6-hydroxy-5-(3-(3-methyl-3H-diazirin-3-yl)propanamido)tetrahydro-2H-pyran-4-yl)oxy)propanamido)propanamido)-5-amino-5-oxopentanoate (I13)

3-(3-methyl-3H-diazirin-3-yl)propanoic acid 2,5-Dioxopyrrolidin-1-yl ester prepared as follows: 3-(3-methyl-3H-diazirin-3-yl)propanoic acid (60.0 mg, 0.468 mmol) and N-hydroxysuccinimide (56.6 mg, 0.491 mmol) dissolved in 600 μL anhydrous dimethylformamide with stirring under nitrogen. 1-ethyl-3-(3-dimethylaminopropyl)carbodiimide 107 mg, 0.562 mmol) was subsequently added and the reaction stirred 16.5 hrs and then was diluted with chloroform. The reaction was washed with water, aqueous 1N HCl (3×) and aqueous saturated sodium chloride. The organic layer was dried with sodium sulfate and evaporated to yield a yellow, semi-viscous oil. Anhydrous diethyl ether was added to the oil to yield a white precipitate. The ether layer was decanted and the precipitate was dried. White powder (78.4 mg, 74%). $^1$H NMR (600 MHz, Chloroform-d) δ 2.83 (s, 4H, NHS methylene (×2)), 2.53-2.50 (m, 2H, methylene), 1.82-1.75 (m, 2H, methylene), 1.07 (s, 3H, methyl). $^{13}$C NMR (151 MHz, Chloroform-d) δ 169.04 (NHS carbonyl (×2)), 167.71 (carbonyl), 29.64 (methylene), 25.85 (methylene), 25.70 (NHS methylene (×2), 24.85 (diazirine), 19.61 (methyl).

I12 (40.0 mg, 0.073 mmol) and sodium carbonate (15.5 mg, 0.146 mmol) suspended in 600 μL anhydrous methanol with stirring under nitrogen. 3-(3-methyl-3H-diazirin-3-yl) propanoic acid 2,5-Dioxopyrrolidin-1-yl ester (37.8 mg, 0.146 mmol) dissolved in 900 μL and 300 μL added at 15 min intervals (3×). The reaction stirred a total of 45 mins and was subsequently quenched with Amberlite IR120, H form ion exchange resin. The mixture was filtered, evaporated and the residue purified by column chromatography (3% methanol/dichloromethane, 5% methanol/dichloromethane then 10% methanol/dichloromethane). White powder (26.0 mg, 54% yield). $^1$H NMR (600 MHz, Methanol-d4) (Anomers—1.00 α: 0.09 β) δ 5.14 (d, J=3.4 Hz, 1H, α 1-H), 5.01-4.94 (m, 1H, α 4-H), 4.34 (dd, J=9.5, 4.7 Hz, 1H, α isoglutamine C—H), 4.25-4.12 (m, 4H, α alanine C—H, α C—H, α 5-H, α 6-H), 4.07-4.02 (m, 2H, α 2-H, α 6'-H), 3.84 (dd, J=10.3, 9.4 Hz, 1H, α 3-H), 3.67 (s, 3H, α methyl ester), 2.42 (t, J=7.6 Hz, 2H, α isoglutamine methylene), 2.23 (ddt, J=14.2, 8.1, 4.0 Hz, 1H, α isoglutamine methylene), 2.15-2.05 (m, 5H, α acetyl, α diazirine linker methylene), 2.04 (s, 3H, α acetyl), 1.91 (ddt, J=14.2, 9.4, 7.1 Hz, 1H, α isoglutamine methylene), 1.70-1.55 (m, 2H, α diazirine linker methylene), 1.39 (d, J=7.2 Hz, 3H, α alanine methyl), 1.29 (d, J=6.8 Hz, 3H, α methyl), 1.01 (s, 3H, α diazirine linker methyl). $^{13}$C NMR (151 MHz, Methanol-d4) δ 176.09 (carbonyl), 175.65 (carbonyl), 175.19 (carbonyl), 174.85 (carbonyl), 174.59 (carbonyl), 172.53 (carbonyl), 171.71 (carbonyl), 92.52 (α 1-C), 78.54 (α C—H), 78.06 (α 3-C), 71.71 (α 4-C), 68.62 (α 5-C), 63.83 (α 6-C), 55.59 (α 2-C), 53.57 (α isoglutamine C—H), 52.22 (α methyl ester), 50.96 (α alanine C—H), 31.41 (a diazirine linker methylene), 31.37 (α diazirine linker methylene), 31.15 (α isoglutamine methylene), 27.94 (α isoglutamine methylene), 26.32 (α diazirine), 20.97 (α acetyl), 20.67 (α acetyl), 19.68 (α diazirine linker methyl), 19.49 (α methyl), 17.52 (α alanine methyl). LRMS (ESI-Pos) for $C_{27}H_{42}N_6O_{13}$ (658.28): 659.20 [M+H]$^+$.

(R)-methyl 4-((S)-2-((R)-2-(((2R,3S,4R,5R,6R)-3-acetoxy-2-(acetoxymethyl)-6-(2-azidoethoxy)-5-(3-(3-methyl-3H-diazirin-3-yl)propanamido)tetrahydro-2H-pyran-4-yl)oxy)propanamido)propanamido)-5-amino-5-oxopentanoate (I14)

I13 (25.0 mg, 0.038 mmol) dissolved in anhydrous 1,2-dichloroethane. Trichloroacetonitrile (38.1 μL, 0.380 mmol) and 1,8-Diazabicycloundec-7-ene (2.8 μL, 0.019 mmol) added and reaction stirred 1.5 hrs. Reaction evaporated and residue purified by column chromatography (ethyl acetate). Clear oil (21.8 mg, 73% yield). Azeotroped with toluene (3×), dissolved along with 2-azidoethanol (9.5 mg, 0.108 mmol) in 800 μL 1,2-dichloroethane and stirred over 4A molecular sieves for 1 hr. Reaction cooled to −10° C. and trimethylsilyl trifluoromethanesulfonate (2.5 μL, 0.014 mmol) added dropwise. Reaction allowed to stir and warm to room temperature. Additional 2-azidoethanol (9.5 mg, 0.108 mmol per addition) added at 1 hr intervals (8×) and reaction allowed to stir for 9 hrs total before quenching with triethylamine and subsequent evaporation of the solvent. The residue was purified by column chromatography (10% methanol/dichloromethane). White solid (13.7 mg, 69% yield). $^1$H NMR (600 MHz, Methanol-d4) (Anomers—0.19 α: 1.00 β) δ 4.97 (t, J=9.6 Hz, 1H, β 4-H), 4.56 (d, J=8.4 Hz, 1H, (β 1-H), 4.35 (dd, J=9.5, 4.7 Hz, 1H, β isoglutamine C—H), 4.25 (dd, J=12.3, 4.7 Hz, 1H, β 6-H), 4.20 (q, J=7.1 Hz, 1H, β alanine C—H), 4.13 (dd, J=12.3, 2.3 Hz, 1H, β 6'-H), 4.05 (q, J=6.7 Hz, 1H, β C—H), 3.95 (ddd, J=10.9, 5.3, 3.4 Hz, 1H, β azide linker methylene), 3.92-3.88 (m, 1H, β 2-H), 3.78-3.74 (m, 1H, β 3-H), 3.74-3.71 (m, 1H, β 5-H), 3.71-3.68 (m, 1H, β azide linker methylene), 3.67 (s, 3H, β methyl ester), 3.45 (ddd, J=11.2, 7.9, 3.3 Hz, 1H, β azide linker methylene), 3.35 (ddd, J=13.4, 5.2, 3.3 Hz, 1H, β azide linker methylene), 2.41 (t, J=7.6 Hz, 2H, p isoglutamine methylene), 2.23 (dtd, J=12.8, 8.0, 4.8 Hz, 1H, β isoglutamine methylene), 2.10 (s, 3H, β acetyl), 2.09-2.03 (m, 5H, β acetyl, β diazirine linker methylene), 1.91 (ddt, J=14.3, 9.1, 7.2 Hz, 1H, β isoglutamine methylene), 1.71-1.56 (m, 2H, β diazirine linker methylene), 1.41 (d, J=7.2 Hz, 3H, β alanine methyl), 1.29 (d, J=6.7 Hz, 3H, β methyl), 1.01 (s, 4H, diazirine linker methyl). $^{13}$C NMR (151 MHz, Methanol-d4) δ 176.06 (carbonyl), 175.07 (carbonyl), 175.00 (carbonyl), 174.83 (carbonyl), 174.70 (carbonyl), 172.41 (carbonyl), 171.59 (carbonyl), 102.20 (β 1-C), 80.69 (β 3-C), 79.20 (β C—H), 73.08 (β 5-C), 70.97 (β 4-C), 69.43 (β azide linker methylene), 63.45 (β 6-C), 56.93 (β 2-C), 53.50 (β isoglutamine C—H), 52.21 (β methyl ester), 51.84 (β azide linker methylene), 50.91 (β alanine C—H), 31.61 (β diazirine linker methylene), 31.14 (β diazirine linker methylene), 31.11 (β isoglutamine methylene), 28.03 (β isoglutamine methylene), 26.33 (β diazirine), 20.95 (β acetyl), 20.67 (β acetyl), 19.73 (β diazirine linker methyl), 19.25 (β methyl), 17.54 (β alanine methyl). LRMS (ESI-Pos) for $C_{29}H_{45}N_9O_{13}$ (727.31): 728.30 [M+H]$^+$.

(BD45)

I14 (1 eq) and pyridine (20 eq) dissolved in THF/dioxane/$H_2O$ (4:2:1) and approximately 3 hrs. Upon completion the reaction is evaporated and can be purified by LCMS.

Our synthesis begins with the inexpensive and readily obtainable starting material glucosamine hydrochloride. Imidazole-1-sulfonyl azide was prepared and a diazo-transfer was performed to install an azide protecting group to the 2-position, followed by acetylation of the hydroxyl groups to yield I1. The anomeric position was selectively deacetylated, a chloride was installed and subsequently a Koenigs-Knorr type reaction was performed to place the O-benzyl protecting group. A Zemplén deprotection removed the remaining acetates and a 4,6-O-benzylidene protecting group was installed to produce I5. In the presence of sodium hydride and (S)-2-Chloropropionic acid, the modularly protected muramic acid intermediate I6 was produced in moderate yield. Our first coupling was performed using HBTU, N-methylmorpholine and L-Alanine methyl ester hydrochloride. The L-Alanine ester was subsequently deprotected and D-Isoglutamine benzyl ester perchlorate was coupled using HOBt/EDC and 2,4,6-Collidine to provide us with I9. With modularly protected MDP in hand we were ready to deprotect our carbohydrate and expose the 2-amino functionality. Global deprotection was performed using Pd/C and $H_2$ to yield D1. Finally, acetylation of the 2-amino position under mild conditions with acetic anhydride furnished our N-acetyl-MDP target (D2), providing a simplified route to the minimal peptidoglycan fragment known to activate an immune response in 10 linear steps from glucosamine hydrochloride with an overall yield of 33%.

Having established a synthesis that allowed for the late-stage modification of the 2-amino position and the potential to yield a variety of N-substituted MDPs via intermediate D1 we set out to produce other peptidoglycan and peptidoglycan-like derivatives. Functionality was chosen for coupling that would produce MDP derivatives applicable for use as chemical tools for the study of biological systems from peptidoglycan biosynthesis to peptidoglycan induced innate immune system activation. Moreover, our scheme allows for installation of orthogonal modification, permitting the synthesis of peptidoglycan derivatives with chemical tools attached at the carboxylic acid functionality in addition to the 2-position.

The synthesis can be easily adapted for the production of N-acetylmuramic acid derivatives as well. A global deprotection of I6 produces the 2-amino muramic acid fragment A1, which can be functionalized on the 2-position with a variety of functional groups in the same manner as above.

The NAM derivatives may also be generated via a chemoenzymatic route. For example, some NAM derivatives may be generated in vitro in the presence of bacterial enzymes. In some embodiments, compound B and C may be synthesized in vitro in the presence of P. putida recycling enzymes AmgK and MurU. In other embodiments, compound B or C may be used to synthesize other NAM derivatives in vitro in the presence of E. coli biosynthetic enzymes MurC, MurD, MurE, and MurF.

The synthesis process according to the present invention generates a variety of NAM derivatives useful for production of a large number of peptidoglycan fragments. The NAM derivatives and peptidoglycan composed of these NAM derivatives are useful for biological studies of bacterial cell wall structures and modulating innate immune response.

According to a third aspect of the present invention, a method for modulating nucleotide-binding oligomerization domain-containing protein 2 (Nod2) in a cell is provided. The method comprises exposing the cell with an effective amount of an NAM derivative of the present invention. Za maybe OH or a peptide selected from the groups consisting of monopeptides, dipeptides, tripeptides and pentapeptides, which peptide may or may not have an ethylene diamine coupled fluorophore. The NAM derivative is preferably not A2 or A9. Preferably, the NAM derivative is compound A, C, D or BD.

The modulation may be carried out in vitro or in vivo. The cell may be either isolated from an organism or in an organism. The cell is preferably isolated from an organism. In some embodiments, the organism expresses Nod2 or a homolog thereof. Examples of a Nod2 homolog include those expressed by zebra fish, fungi and other non-mammals. The organism may be an animal, fish or fungi. The animal may be selected from the group consisting of a human being, mouse, rat, horse and cow. Preferably, the animal is a mammal. More preferably, the animal is a human being. In some embodiments, the organism is in need for up-regulation of Nod2 activity. In some other embodiments, the organism is in need for down-regulation of Nod2 activity.

The term "modulating" as used herein refers to changing or influencing the activity of Nod2. The Nod2 activity may be up-regulated by stabilizing Nod2 or down-regulated by destabilizing Nod2 in the cell exposed to the NAM derivative by, for example, at least about 1, 2, 5 or 10 folds. The Nod2 activity may be regulated by post-translational modifications (e.g., O-glcnacylation). A Nod2 regulated signal pathway such as NF-κB pathway in the cell exposed to the NAM derivative may be up-regulated or down-regulated in the cell upon exposure to an NAM derivative by, for example, at least about 1%, 5%, 10%, 20% or 50%.

The method may further comprise stabilizing the Nod2 in the cell exposed to the NAM derivative. The half-life of the Nod2 may be increased by, for example, at least about 1, 2, 5 or 10 folds, preferably at least about 2 folds, compared to Nod2 without stimulation.

The method may further comprise activating nuclear factor kappa-light-chain-enhancer of activated B cells (NF-κB) in the cell exposed to the NAM derivative. The activity of the NF-κB may be increased by at least about 1%, 5%, 10%, 20% or 50%, preferably at least about 20%.

According to a fourth aspect of the present invention, a method for modifying the cell wall of a bacterial cell is provided. The method comprises (a) exposing the bacterial cell to an effective amount of an NAM derivative, in which Za is OH, (b) making a peptidoglycan from the NAM derivative in the bacterial cell, and (c) incorporating the peptidoglycan from step b into the cell wall of the bacterial cell. As a result, the modified cell wall of the bacterial cell is obtained. In some embodiments, Xa is selected from the group consisting of X3-X8, X10-X22, X24-X25, X28, X30-X35 and X44-X59, preferably selected from the group consisting of X3-X8, X10-X21, X25, X28, X30, X31, X45-X48, X54 and X55

The bacterial cell may be a cell of a bacterium of E. coli, P. put, B. subtilis, S. aureus, human pathogen or any member of the microbiome. The term "microbiome" used herein refers to the community of commensal, symbiotic and pathogenic microorganisms that colonize a mammalian body. An example of a microbiome is the human microbiome.

In some embodiments, an NAM derivative is incorporated into bacterial cell wall intermediates in vitro via AmgK, MurU, MurC, MurD, MurE and MurF. The bacterial cell may or may not express any or all of enzymes AmgK, MurU, MurC, MurD, MurE and MurF.

Where the NAM derivative incorporated into the bacterial cell wall is labeled with, for example, a fluorophore, the corresponding bacterial cell peptidoglycan is also labeled and may be visualized. Preferably, the bacterial cell is live and labeled by its cell wall via bioorthogonal reactions, in the presence or absence of mammalian cells. Such a labeled bacterial cell may, preferably modified with NAM derivatives A28, A25, A45, A46, or A47 as described in this aspect, be introduced to a mammalian host for study of peptidoglycan interactions.

According to a fifth aspect of the present invention, a modified peptidoglycan or a fragment thereof is provided. The modified peptidoglycan is isolated from a modified cell wall of a bacterial cell obtained according to the method of the present invention. The isolation of the modified peptidoglycan may be achieved by techniques known in the art. According to a sixth aspect of the present invention, a method to modulate an innate immune response of a subject to a bacterial cell is provided. The method comprises exposing the subject to an effective amount of a modified bacterial cell wall or a fragment thereof according to the present invention. The subject may be any an animal, for example, a human being, mouse, rat, horse, cow or any other Nod2 (or homologue) expressing organism. Preferably, the animal is a human being. The bacterial cell may be a cell of E. coli, P. put, B. subtilis, S. aureus, human pathogen or any member of the microbiome.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Example 1. Peptidoglycan Modifications Tune the Stability and Function of the Innate Immune Receptor Nod2

We investigated how acetylation/deacetylation of these peptidoglycan fragments modulates molecular recognition by Nod2.

In order to further study the interaction of N-substituted MDPs, for example, naturally occurring muramyl dipeptides (MDP), N-acetyl-MDP (compound D2), N-glycolyl-MDP (compound D9) and 2-amino-MDP (compound D1), and Nod2, we required a synthetic route for MDP that offers selective functionalization of the 2-position. Existing synthetic strategies require extensive carbohydrate manipulation, troublesome dipeptide couplings, or expensive carbohydrate starting materials and to date, no existing syntheses allow for a facile, late-stage modification at the 2-position. Additionally, no syntheses exist for the deacetylated peptidoglycan derivatives. We therefore examined a rapid and modular synthesis that would allow for alterations at the 2-position and provide a divergent route for a variety of peptidoglycan and peptidoglycan-like derivatives. We present here a synthetic route that: (1) allows general exploration of function via acylation at the carbohydrate 2-position and (2) utilizes an azide, a sterically unobtrusive acid and base stable protecting group to mask the amine in the synthetic approach.

Figure 3:
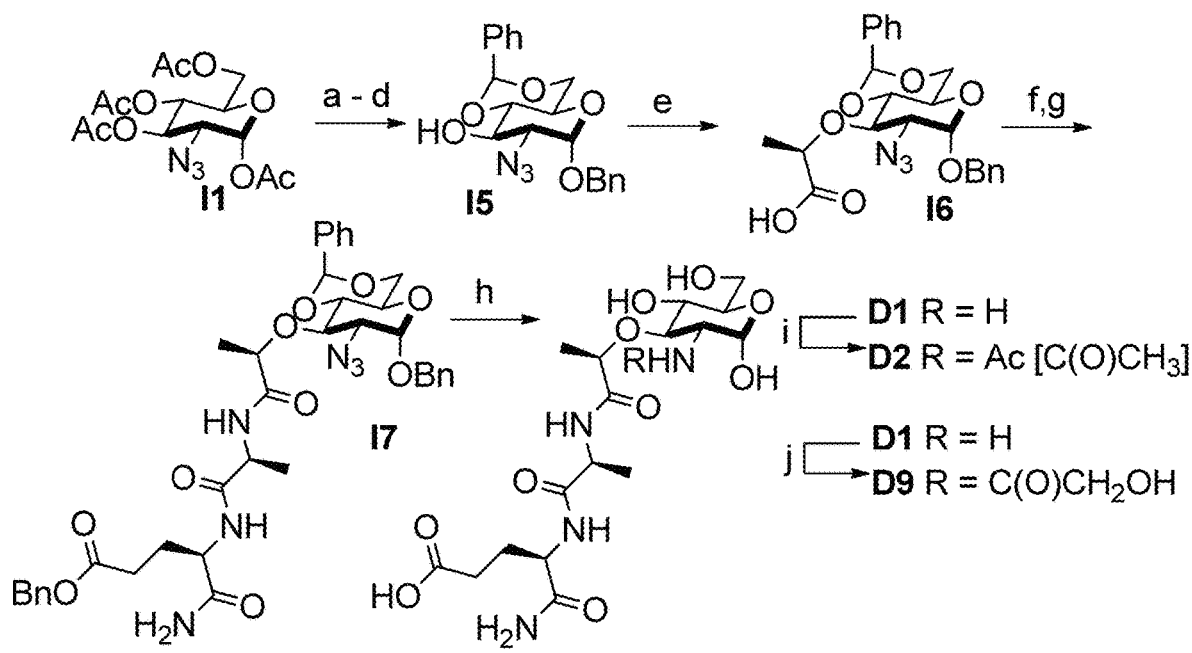
FIG. 3 illustrates Scheme 1 for synthesis of naturally occurring muramyl dipeptides (MDP), N-acetyl-MDP (compound D2), N-glycolyl-MDP (compound D9) and 2-amino-MDP (compound D1). Reagents and conditions: (a) Hydrazine acetate, DMF, 80%; (b) 1. Oxalyl chloride, cat. DMF, DCM; 2. Benzyl alcohol, cat. Ag2CO3, cat. AgOTf, DCM, 85%; (c) cat. NaOMe, MeOH, quantitative; (d) cat. pTSA, benzaldehyde dimethyl acetal, DMF, 95%; (e) NaH, (S)-2-chloropropionic acid, DMF, 76%; (f) 1. HBTU, N-methylmorpholine, DMF, 2. L-alanine methyl ester hydrochloride, 81%; (g) 1. KOH, MeOH, 2. HOBt, EDC, DMF, 2,4,6-collidine, 3. D-isoglutamine benzyl ester perchlorate, 89%; (h) Pd/C, H2O, MeOH, AcOH, quantitative; (i) H2O, NaHCO3, Ac2O, quantitative (j) MeOH, Na2CO3, acetoxyacetic acid NHS ester, 85%.

The synthesis (FIG. 3) begins with the inexpensive and readily obtainable starting material glucosamine hydrochloride, which is easily converted to I5 in six high yielding steps using notably a diazo-transfer to install the azide (I1) and a Koenigs-Knorr type reaction to protect the anomeric position. The coupling reactions of a dipeptide fragment to modularly protected muramic acid derivatives were low yielding; therefore, we opted to perform the amino acid couplings sequentially. Global deprotection was performed using Pd/C and $H_2$ to expose the 2-amino functionality and yield D1, a N-deacetylated naturally occurring MDP. Acetylation of the 2-amino position under mild conditions furnished the N-acetyl-MDP target (D2) and the N-glycolyl-MDP target (D9) in ten linear steps from glucosamine hydrochloride with overall yields of 33% and 28% respectively. The synthesis provides a simplified route to the minimal peptidoglycan fragments known to activate Nod2.

Having established a synthesis that allowed for the late-stage modification of the 2-amino position and the potential to yield a variety of new, 2-amino functionalized MDPs via the naturally occurring deacetylated MDP (D1), we set out to produce other peptidoglycan-like derivatives (Table 3) in order to explore their effect on Nod2 signaling. Functionality was chosen for coupling that would produce MDP derivatives applicable for use as chemical tools to study biological systems from peptidoglycan biosynthesis to peptidoglycan induced innate immune system activation. We synthesized the acetylated (D22) and methyl ether D53) versions of D9 to probe how altering the glycolyl substitution affects Nod2 recognition. compound D16 inverses the electronics from the parent compound D2. Compounds D23 and D24 represent extended acetylations reminiscent of D2 and D9. Finally D25, D29 and D44 represent MDP derivatives that are applicable to click-chemistry, fluorophore-based assays and anchoring to avidin/streptavidin, respectively. Additionally, this strategy allows for installation of orthogonal modification, permitting the synthesis of peptidoglycan derivatives with chemical tools at locations other than the 2-position. Finally, one can envision the installation of a $^{13}C$ or $^{14}C$ labeled acetate to yield the isotopes of D2, tools that are important in studying innate immunity, for NMR analysis and other biological studies.

Figure 4:
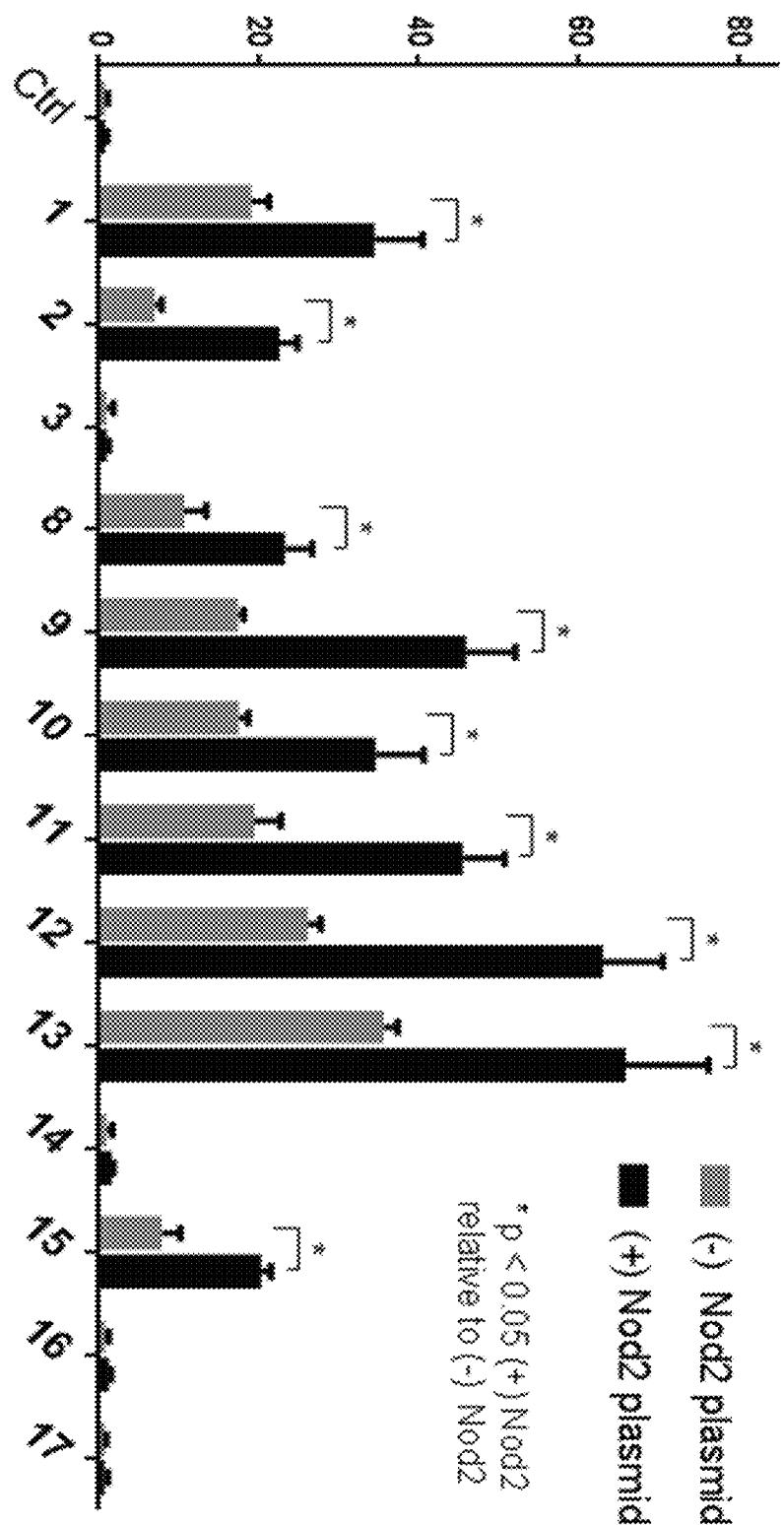
FIG. 4 shows NF-κB activation with standard deviation for peptidoglycan derivatives: HEK293T cells were transfected using Lipofectamine with (+) or without (−) Nod2 plasmid, NF-κB reporter, and a *renilla* control for 16 h. The cells were treated with stimuli (Ctrl, water; 1, compound D2; 2, compound D9; 3, compound D1; 8, compound D22; 9, compound D53; 10, compound D16; 11, compound D23; 12, compound D24; 13, compound D25; 14, compound D29; 15, compound D44; 16, compound AI2; 17, compound AI9) for 12 h, harvested, and tested for luciferase activity (*=P<0.05, activates in a Nod2-dependent manner). All compounds were tested at 20 μM. Two effects are seen: (1) the native effect of the MDP derivatives (gray bar vs. control) on NF-κB signaling, which could be due to native Nod2 or other targets activated by MDP; and (2) the induced effect of the MDP derivatives (gray bars vs. black bars for a given compound) on overexpressed Nod2.

To directly determine how modification at the 2-position affects innate immune system activation, the MDP derivatives (D2, D9, D1, D22, D53, D16, D23, D24, D25, D29, D44, AI2 and AI9 were assayed for activity (as products 1-3 and 8-18, respectively, in FIG. 4, Table 4) using a Nod2-dependent NF-κB reporter assay. All compounds were tested at 20 µM, as we have shown in an in vitro binding assay that Nod2 binds to D2 with a $K_D$ of 51 nM. compound D1, the N-deacetylated-MDP, did not activate NF-κB thus suggesting that N-acylation is an important feature for recognition by the Nod2 signaling cascade. Most modifications are tolerated at the 2-position with Compounds D53, D16, D23, D24, D25 activating Nod2 approximately 2-fold greater than then the untreated control. The fluorescent derivatives (D29, AI2, AI9) do not activate regardless of fluorophore position. In contrast, placement of a biotin molecule, containing four methylenes (separating the amide from the heterocycle), at the 2-position (D44) still allows activation of NF-κB, albeit to a lesser extent than the other acylated derivatives. These data suggest that the installation of a fluorophore is possible with increased linker length. The data also shows that there is significant NF-κB activation in HEK293T cells, which follows the same trend as the Nod2 induced effect. This could be from either the endogenous Nod2 and/or other targets of the bacterial cell wall ligands. Overall these data demonstrate that modification of the 2-position can be used for optimization/modulation of the Nod2 response.

Figure 5:
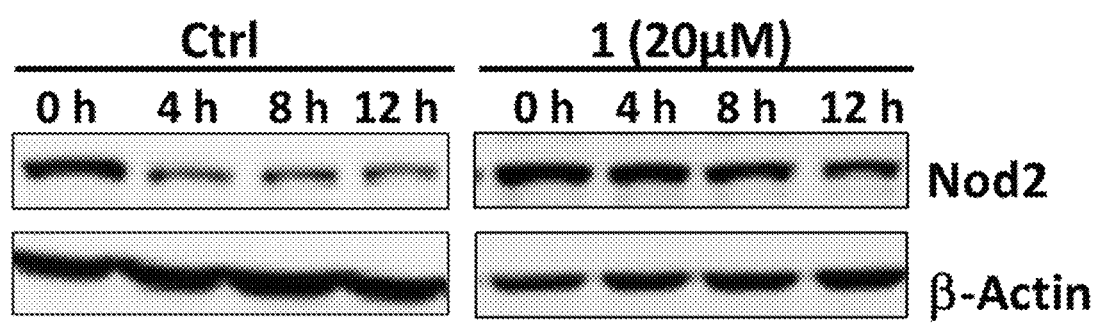
FIG. 5 shows that peptidoglycan derivatives stabilize Nod2. HEK 293T-Nod2myc/Tet-op cells were incubated with MDP derivatives (compound D2 is shown) or water (Ctrl) and lysates were collected after cycloheximide treatment during the indicated time intervals. Equal amount of lysates were subjected to western blot and probed using rabbit anti-myc antibody. β-actin was used as a loading control.

Nod2 is a transiently stable protein. It is well-known that ligand binding can affect the stability of a receptor. We considered that the interaction of peptidoglycan derivatives with Nod2 could alter the stability of the protein. In order to determine if ligand interaction changes the half-life of Nod2, we analyzed the naturally occurring MDPs (D2, D9, D1), and a subset of the peptidoglycan derivatives with increased activity (D24, D25) or structural similarity (D53, D16) to D2 or D9. We made use of a tetracycline-induced Nod2 expressing cell line, an excellent match for endogenous Nod2 cell lines, and cycloheximide inhibition of protein synthesis to determine the half-life of Nod2 in the presence of the MDP derivatives. Half-life was determined by first order decay according to literature precedent. Treatment with either D2 or D9 significantly increases the Nod2 half-life (FIG. 5, Table 4). When Nod2 is not treated with a peptidoglycan derivative, the half-life is 7.1±1.4 hours. However, when cells are treated with D2, the half-life is 15.9±4.1 hours, and if cells are treated with D9, the half-life is 23.1±2.2 hours. The N-deacetylated derivative (D1) provided no stabilization of Nod2 (Table 4). Notably, the N-glycolyl derivative (D9) promotes greater stabilization of Nod2 than the N-acetyl derivative (D2), suggesting that Nod2-dependent NF-κB activation and Nod2 stabilization are correlated for the naturally occurring Compounds D2, D9, D1) (Table 4). As compound D1 is the only compound tested that contains an amine, which will be positively charged at cellular pH, we were concerned that cell permeability may be a factor. We analyzed the ability of 6-amino-MDP (18 in Table 4), a MDP derivative that replaces the 6-primary-hydroxy group with an amine. This compound is known to activate NF-κB in a Nod2-dependent manner. Despite the presence of the charged ammonium ion, 6-amino-MDP increased the half-life of Nod2 by nearly 3-fold (Table 4), indicating that the presence of a free amine does not prevent cellular access.

Other N-substituted derivatives tested significantly stabilized Nod2 compared to the untreated control (Table 4), indicating that these modifications likely do not alter the ability of the ligand to bind and/or stabilize Nod2. The correlation between Nod2 dependent NF-κB activation and Nod2 stabilization was not as strong for these compounds as the natural compounds (D2, D9, D1), indicating that these compounds may have differential permeabilites and/or cell degradation pathways. It is important to note that compounds (D1, AI2) that did not activate also did not stabilize (Table 4). The half-life data demonstrate that peptidoglycan derivatives are capable of altering the stability of the receptor, implying that ligand recognition is important for the signaling processes by initiating and maintaining the response. We note earlier studies using mouse Nod2 showed that treatment with very high concentrations (200 µM) of D2 led to the degradation of Nod2 when protein synthesis is not inhibited, thus suggesting there are other feedback mechanisms to control Nod2 levels in the cell. The data presented here demonstrate the ability to modulate Nod2 stability via natural or unnatural variation at the site of acetylation.

In their natural environments, virulent bacteria modify their peptidoglycan to evade detection by the innate immune system. Acetylation of the 6-position of the carbohydrate and deacetylation of the 2-position prevents cell wall degradation by lysozyme. Interestingly, these data demonstrate that deacetylation of the 2-position also eliminates the ability of the peptidoglycan fragment to signal through the Nod2-dependent pathway. Acetylation of the 6-position does not affect the ability to stimulate the Nod2-dependent immune response. These data suggests that the deacetylation strategy used by bacteria is two pronged in that the modification (D1) yields lysozyme resistant peptidoglycan that does not elicit an immune response via the Nod2-dependent pathway.

In addition to its role in recognizing pathogenic bacteria, Nod2 is critical for maintaining the proper balance of commensal bacteria. Interestingly, Nod2 mutations that correlate with development of the inflammatory bowel disease, Crohn's disease, are unable to activate Nod2[1]. Previous experiments have shown that these mutations are unstable compared to the wild type protein and signaling can be restored via stability of Nod2 by the chaperone protein, Hsp70. This report shows that: (1) simple peptidoglycan derivatives stabilize Nod2 and (2) modifications at the 2-position alter the stability of Nod2. Therefore, peptidoglycan derivatives produced by these methods may stabilize Crohn's associated Nod2 mutations, providing therapeutic leads.

In conclusion, acylation of peptidoglycan derivatives at the 2-position allows for the tuning of Nod2 stability and NF-κB response. This new, rapid, tunable, high yielding synthesis of peptidoglycan derivatives allowed the production of analogues to probe the substrate requirements for activation and stabilization effects on the protein. Nature produces ligands (D2, D9) that are capable of stabilizing Nod2 and other ligands (D1) that produce no stabilizing effect. Moreover, synthetic, novel peptidoglycan-like derivatives can activate and stabilize Nod2, informing on requirements for modulating the innate immune signaling cascade in response to bacterial cell wall fragments.

Figure 6:
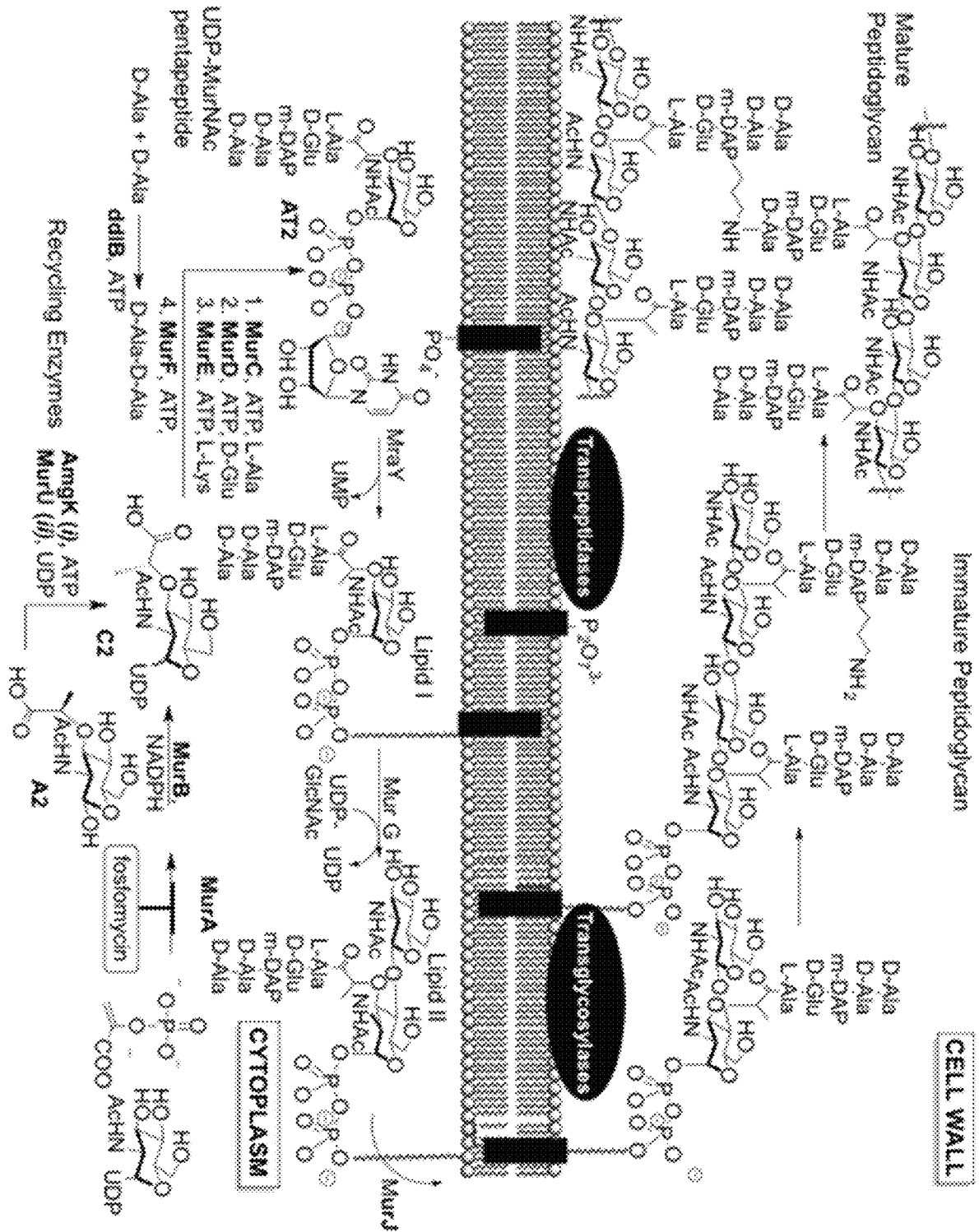
FIG. 6 illustrates peptidoglycan biosynthesis and glycoengineered building blocks. a, Peptidoglycan biosynthesis begins with the formation of UDP-N-acetyl-muramic acid (UDP-MurNAc) either through MurA/B and UDP-N-acetyl glucosamine (UDP-GlcNAc) or *P. putida* recycling enzymes AmgK, MurU and building block NAM. UDP-MurNAc is converted into Park's nucleotide through enzymes MurC-F. Then enzyme MraY links Park's nucleotide to the cell membrane where MurG then glycosylates this fragment to form Lipid II. MurJ transports Lipid II into the periplasmic space where transglycosylases (TGase) and transpeptidases (TPase) further crosslink the polymer to form the mature peptidoglycan. b, Library of NAM derivatives A2, A25, A28, A24, and A45 treated with i) AmgK and ii) MurU to yield compounds B2, B25, B28, B24, B45, and C2, C25, C28, C24, C45, respectively.
Figure 6:
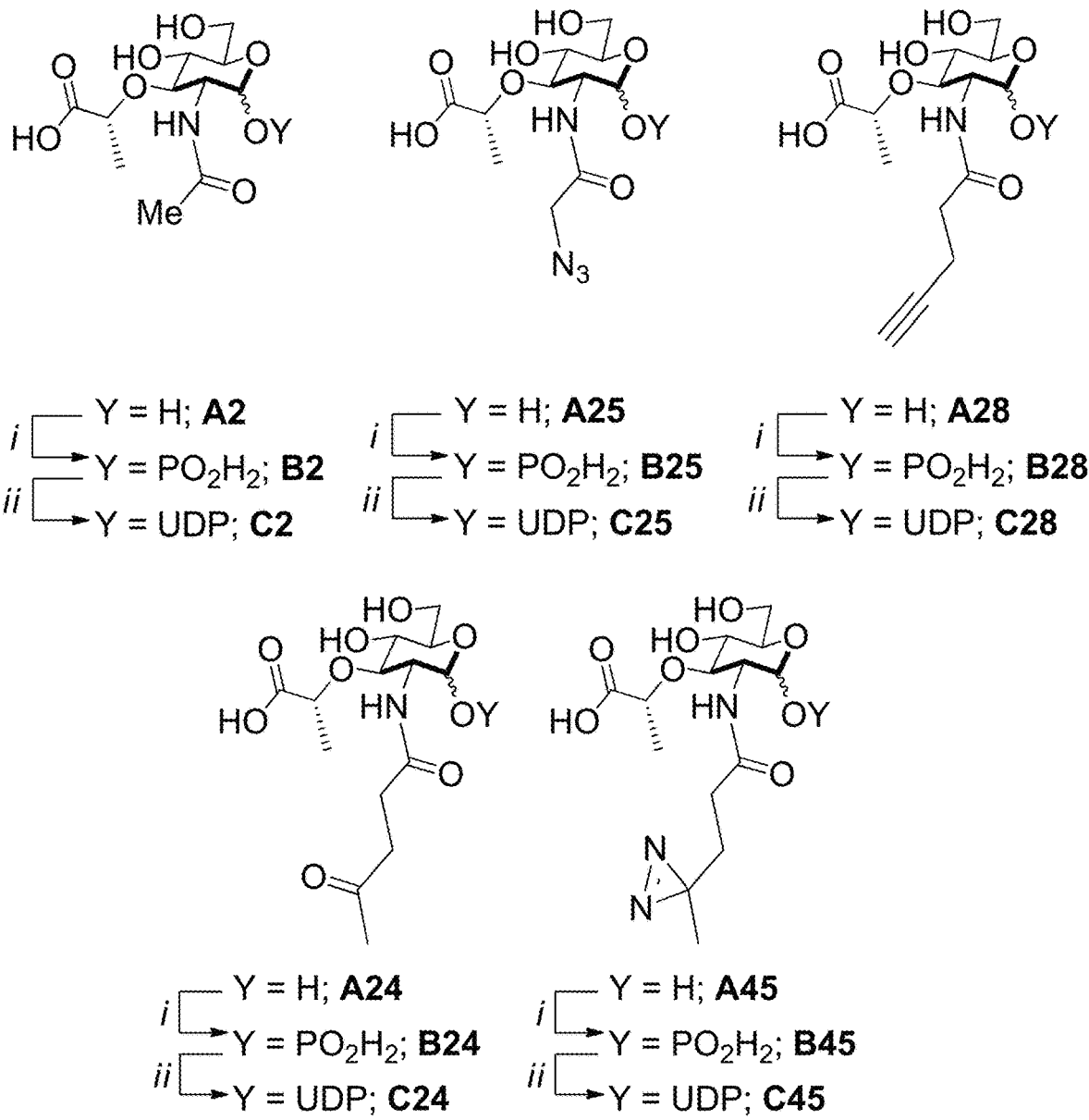

Example 2. Glycoengineering of Peptidoglycan to Study Bacterial Cell Wall Structure and Function The fundamental building blocks of bacterial cell wall are the glycans NAG and NAM. NAM is exclusively used as a peptidoglycan building block. This monosaccharide is introduced during the first committed step to bacterial cell wall biosynthesis with the formation of UDP-N-acetyl-muramic acid (UDP-MurNAc) (FIG. 6a). It was at this intermediate that our bioorthogonal handle was installed. To circumvent the synthesis of the gram quantities of the UDP-sugar derivatives and complicated delivery strategies for the diphosphate moiety, we utilized cell wall recycling machinery. The recycling enzyme anomeric NAM/NAG kinase (AmgK) converts NAM into MurNAc 1-phosphate that is then converted to UDP-MurNAc by MurNAc α-1-phosphate uridylyl transferase (MurU) (FIG. 6a). Intrigued by the functionality of these two enzymes, a modular synthetic strategy was implemented to build a library of NAM derivatives (FIG. 6b). This library was then used to demonstrate that recycling and biosynthetic enzymes are able to accept unnatural substrates.

Knowing that the recycling and biosynthesizing pathways are promiscuous, we moved to a cell based assay to label the peptidoglycan polymer using a strain of E. coli previously reported by Mayers and coworkers that contained an altered cell wall machinery. We started our in vivo remodeling and labeling work with the incubation of 0.2% (w/v) sugar substrates with exponentially growth E. coli ΔmurQ-KU cells in the presence of fosfomycin (200 μg/mL) and IPTG (1 mM). After incubation, a subsequent CuAAC reaction was applied to introduce a fluorophore molecule into remodeled peptidoglycan polymer which contains Azide or Alkyne functional group. We checked the labeling result by visualizing fluorescent signals under Structured Illumination Microscopy (SIM). In A25 and A28, we could see that most cells were successfully labeled with our fluorophore (rhodamine or Cy-5). For the control group which E. coli ΔmurQ-KU cells were incubated with A2 sugar, we couldn't detect any fluorescence but only some background signal and very weak cell self-fluorescence. E. coli K12 wild type cells without recycling enzymes AmgK/MurU also couldn't get labeled by this method. From the SIM images we could clearly visualize the Z-ring of dividing E. coli cells. Which indicates that nascent peptidoglycan were assembled and loaded in the middle of dividing E. coli cells. Previous studies about Z-ring were focused on GFP labeled FtsZ, which is a bacterial cell division protein. Our study is the first to show that peptidoglycan sugar components were directly loaded into this ring area during cell division.

We chose to measure the labeling efficiency of this method through fluorescence activated cell sorting (FACS). The E. coli cells with AmgK, MurU and ΔMurQ were incubated with A28 and following "click chemistry" treatment, a Cy-5 fluorochrome was installed. The cells were then analyzed by flow cytometry. After counting 100,000 cells, the fluorescent signal in the gated cy5 channel increased dramatically, indicating the incorporation of the Cy-5 fluorochrome on the bacterial cell surface. As a control, we also used flow cytometry to measure the fluorescence intensity of E. coli cells containing AmgK, MurU and ΔMurQ that were incubated with A2 after CUAAC with a Cy-5 fluorochrome. Compared to untreated E. coli cells, there was a slight fluorescence intensity in the gated Cy-5 channel of this control. The labeling efficiency of the cells with incorporated A28 was further calculated to be above 90% when compared to the MurNAc control (compound A2). To the best of our knowledge, our method has the highest Gram negative bacterial cell wall labeling efficiency to date.

This highly efficient cell wall remodeling and labeling method aided the investigate into the details about bacterial cell wall biosynthesis during cell division process and the architecture of bacterial cell wall. From the SIM images we could identify bacterial cells in different dividing stages. To further study the dividing process, a time course study was launched by incubating the A25 substrate with bacterial cells for different time length. The accumulation of fluorescent signal started from Z-ring area, which happened within the first 15 minutes. About half number of cells was fully labeled at 30 minutes which fits the doubling time of E. coli growth. Most cells were getting fully labeled at 45 minutes and 60 minutes. We are also interested in the dynamic distribution process of the new incorporated compound, so we carried out a pulse-chase study, started with the incubation of A25 for 15 minutes, and then switched to A2 for different time length. After 30 minutes of MurNAc incubation, some of the fully labeled cells showed a disappeared Z-ring. However, most cells remained fully labeled even after 45 minutes of MurNAc incubation.

We performed a Stochastic Optical Reconstruction Microscopy (STORM) experiment with the labeled bacterial cells. The STORM images reveled small regions with cell wall detailed structure. Labeled cell samples with less time of sugar incorporation (from 30 s to 5 min), showed low incorporation of the unnatural substrates. Bright fluorescent dots could be visualized at Z-ring area, evenly distributed dots appeared in the outline of cells, and some dots were linked by fluorescent signal across the surface of cell wall.

These linking signal formed parallel lines on cell wall surface, which indicates that new made peptidoglycan are spiral on the outside.

Our method extended to bacterial invasion of mammalian cells. J774 macrophage cells were infected with our genetically modified *E. coli* cells after incubation with the bioorthogonal A28 modified peptidoglycan. After infection, any extracellular bacteria were removed and all cells were fixed with paraformaldehyde. Then CUAAC was used to incorporate a rhodamine 488 fluorphore selectively into the *E. coli* bacterial cell walls. After nuclear DAPI staining, the cells were visualized under superresolution SIM microscopy. Three-dimensional analysis confirms bacterial invasion into the macrophage cytosol. In addition, this label reveals deformed structural features of the invading bacteria once inside the host. A time course study of infection was also performed. At 20 min infection, whole bacteria were seen in most of the infected macrophage cells. As time progressed, we generally saw an increase in fluorescently labeled fragments present in the macrophage cells, indicating cell wall breakdown. This said labeling method allows selective tracking of the bacterial cell consumption upon macrophage infection.

Selective and efficient methods to label the bacterial cell wall are essential in order to gain a fundamental understanding of the mechanisms of antibiotic resistance and innate immune activation. Herein, we present a method to efficiently and selectively label bacterial peptidoglycan on the NAM unit. Fluorescent labels were introduced into the bacterial peptidoglycan in vivo. The data demonstrate that the label was not lost during the growth of the bacteria. Incorporation was tracked through SIM and STORM experimentation. Furthermore, the label was able to withstand macrophage infection and thus provided the ability to visually track the breakdown of PG in vivo. This complimentary labeling approach advances the way in which we visualize the bacterial cell wall and fragments therein.

Bacterial cell wall remolding and labeling. The model bacterial strains in this study are *E. coli* ΔmurQ-KU and *P. putida*. *E. coli* ΔmurQ-KU cell lines were constructed by transforming pBBR-KU vector into *E. coli* ΔmurQ competent cells. Expression and function of AmgK and MurU enzymes in this bacterium were studied in a fosfomycin-susceptible agar diffusion assay. An agar LB plate was streaked with 50 µL of overnight-incubated-*E. coli* ΔmurQ-KU cells with 0.2% (w/v) NAM sugar A2, and 1 mM IPTG. 6 mm filter discs which contain 200 µg fosfomycin were air dried and placed on each plate. Water or 100 µg carbenicillin were used in control discs. After incubation at 37° C. overnight, the inhibition zone diameters were measured. For cell remolding and labeling in vivo, overnight pre-cultured *E. coli* ΔmurQ-KU cells or *P. putida* cells were inoculated into fresh LB medium and were incubated until the OD600 was about 0.600. 1 mL of cells were collected by centrifugation at 8,000 rpm for 5 min. *E. coli* ΔmurQ-KU cells were resuspended in 200 µL LB medium and *P. putida* cells were resuspended in same amount of M9 minimal medium. 0.2% (w/v) of one NAM sugar A2-A59 or C2-59, where X is preferably selected from the group consisting of X3-X8, X10-X22, X24, X25, X28, X30-X35 and X44-X59, more preferably selected from the group consisting of X3-X8, X10-X21, X25, X28, X30, X31, X45-X48, X54 and X55, and 200 µg/mL fosfomycin were added into both cell samples while 1 mM IPTG was only added to the *E. coli* cell samples. All cells were incubated at 37° C. for time ranging from 15-60 min, depending on the experiment. Then cells were collected (8,000 rpm, 5 min) and washed with 500 µL PBS buffer twice. Cells were resuspended in 200 µL 1:2 tert-butanol:water to prepare for the click reaction. To the bioorthogonally tagged bacterial cells was sequentially added 1 mM $CuSO_4$ solution, 128 µM Tris[(1-benzyl-1H-1, 2,3-triazol-4-yl)methyl]amine (TBTA), 1.2 mM freshly prepared sodium ascorbate, and either 40 µM of azide or alkyne fluor 488 or 2 µM azide or alkyne Cy5 2 µM. Cells were incubated at room temperature for 45 min. Cells were washed four times with 1×PBS. The cells were resuspended in 100 µL 1×PBS and prepared for imaging.

Example 3. Generation of NAM Derivatives Via a Chemoenzymatic Route

Enzymatic reaction conditions. Activity and promiscuity of purified enzymes were studied in the enzymatic reactions. Products were analyzed by HRLC/MS (Table 5). Conditions for each enzymatic reaction are as follows:

Generation of Compounds B1-B59: To 100 mM Tris buffer, pH 7.9, 2.0 mM of a single A1-A52 NAM substrate, 4.0 mM ATP, and 1.0 mM $MgCl_2$ was added 1.0 µg purified AmgK enzyme per 100 µL reaction sample. The reaction was incubated at room temperature for 2 h.

Generation of Compounds C1-059 To 100 mM Tris buffer, pH 7.9, 2.0 mM of a single B1-B52 MurNAc-1P substrate, 4.0 mM UTP (Sigma-Aldrich), and 0.5 U of baker's yeast inorganic pyrophosphatase (Sigma-Aldrich) was added 1.0 µg purified MurU enzyme per 100 µL reaction sample. The reaction was incubated at 37° C. for 3 h.

Generation of Compounds AH1-AH59: To 100 mM Tris buffer, pH 7.9, 2.0 mM of one C1-052 UDP MurNAc derivative, 15 mM $(NH_4)_2SO_4$, 15 mM $MgCl_2$, 2.5 mM 2-mercaptoethanol, 4.0 mM L-Ala, 4.0 mM ATP, and 1.0 mM DTT was added 1.0 µg purified MurC enzyme per 100 µL reaction sample. The reaction was incubated at room temperature for 3 h.

Generation of Compounds AW1-AW59: To 100 mM Tris buffer, pH 7.9, 2.0 mM of one AH1-AH52 UDP-MurNAc-L-Ala, 4.0 mM D-Glu, 4.0 mM ATP, and 2.0 mM $MgCl_2$ was added 1.0 µg purified MurD enzyme per 100 µL reaction sample. The reaction was incubated at room temperature for 3 h.

Generation of Compounds AQ1-AQ59: To 100 mM Tris buffer, pH 7.9, 2.0 mM of one AW1-AW52 UDP-MurNAc-L-Ala-D-Glu derivative, 4.0 mM meso-DAP (Sigma-Aldrich), 4.0 mM ATP, 2.0 mM $MgCl_2$, and 1.0 mM DTT, was added 1.0 µg purified MurE enzyme per 100 µL reaction sample. The reaction was incubated at room temperature for 3 h.

Generation of Compounds AT1-AT59: To 100 mM Tris buffer, pH 7.9, 2.0 mM of one AQ1-AQ52 UDPMurNAc-L-Ala-D-Glu-m-DAP derivative, 4.0 mM D-Ala-D-Ala (Sigma-Aldrich), 4.0 mM ATP, and 2.0 mM $MgCl_2$ was added 1.0 µg purified MurF enzyme per 100 µL reaction sample. The reaction was incubated at room temperature for 3 h.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

TABLE 1

Structures of Xa Groups 1-59

| Xa | Structure |
|---|---|
| X1 | H |
| X2 | (acetyl) — C(=O)CH$_3$ |
| X3 | $^{13}$C(=O)CH$_3$ |
| X4 | $^{13}$C(=O)$^{13}$CH$_3$ |
| X5 | C(=O)$^{13}$CH$_3$ |
| X6 | $^{14}$C(=O)CH$_3$ |
| X7 | $^{14}$C(=O)$^{14}$CH$_3$ |
| X8 | C(=O)$^{14}$CH$_3$ |
| X9 | (glycolyl) — C(=O)CH$_2$OH |
| X10 | $^{13}$C(=O)CH$_2$OH |
| X11 | $^{13}$C(=O)$^{13}$CH$_2$OH |
| X12 | C(=O)$^{13}$CH$_2$OH |

TABLE 1-continued

Structures of Xa Groups 1-59

| Xa | Structure |
|---|---|
| X13 | $^{14}$C(=O)CH$_2$OH |
| X14 | $^{14}$C(=O)$^{14}$CH$_2$OH |
| X15 | C(=O)$^{14}$CH$_2$OH |
| X16 | C(=O)CF$_3$ |
| X17 | C(=O)CH$_2$F |
| X18 | C(=O)CHF$_2$ |
| X19 | C(=O)C$^{18}$F$_3$ |
| X20 | C(=O)CH$_2^{18}$F |
| X21 | C(=O)CH$^{18}$F$_2$ |
| X22 | C(=O)CH$_2$OAc |
| X23 | C(=O)CH$_2$CH$_2$C(=O)OH |
| X24 | C(=O)CH$_2$CH$_2$C(=O)CH$_3$ |

TABLE 1-continued

Structures of Xa Groups 1-59

| Xa | Structure |
|---|---|
| X25 | acetyl-azide (C(=O)CH₂N₃) |
| X26 | acetyl-alkyne (C(=O)C≡CH) |
| X27 | propargyl ketone (C(=O)CH₂C≡CH) |
| X28 | but-3-ynyl ketone (C(=O)CH₂CH₂C≡CH) |
| X29 | dansyl sulfonyl (5-(dimethylamino)naphthalene-1-sulfonyl) |
| X30 | triazole-Cy5 conjugate (C(=O)CH₂CH₂-triazole-N-Cy5) |
| X31 | triazole-Alexa 488 conjugate |
| X32 | triazole-TAMRA conjugate |
| X33 | triazole-Rhodamine conjugate |
| X34 | triazole-Flourescein conjugate |
| X35 | triazole-Dansyl conjugate |
| X36 | C(=O)CH₂CH₂NH-Cy5 |
| X37 | C(=O)CH₂CH₂NH-Alexa 488 |
| X38 | C(=O)CH₂CH₂NH-TAMRA |
| X39 | C(=O)CH₂CH₂NH-Rhodamine |
| X40 | C(=O)CH₂CH₂NH-Flourescein |
| X41 | C(=O)CH₂CH₂NH-Dansyl |
| X42 | nanoparticle-azide functionalized (via triazole linker) |
| X43 | nanoparticle-alkyne functionalized (via triazole linker) |
| X44 | biotin amide |

TABLE 1-continued

Structures of Xa Groups 1-59

| Xa | Structure |
|---|---|
| X45 | (ketone-linked methyl diazirine with methyl) |
| X46 | (ketone-linked diazirine with butynyl) |
| X47 | (ketone-linked diazirine with azidoethyl) |
| X48 | (benzoyl-benzoyl group) |
| X49 | (ketone-linked methylcyclopropene) |
| X50 | (ester-linked trans-cyclooctene) |
| X51 | (ketone-linked bicyclononyne, BCN) |
| X52 | (ester-linked tetrazine-ethanol) |
| X53 | (ketone with CH$_2$OMe) |
| X54 | (triazole-linked Cy5) |
| X55 | (triazole-linked Alexa 488) |
| X56 | (triazole-linked TAMRA) |
| X57 | (triazole-linked Rhodamine) |
| X58 | (triazole-linked Fluorescein) |
| X59 | (triazole-linked Dansyl) |

TABLE 2

NAM Derivatives

| Compound # | Structure |
|---|---|
| A | (NAM sugar with XaHN substituent and lactic acid) |

TABLE 2-continued

NAM Derivatives

| Compound # | Structure |
|---|---|
| B | (structure: NAM with lactyl group and phosphate) |
| C | (structure: UDP-NAM with lactyl group) |
| D | (structure: NAM-tripeptide, lactyl-Ala-Glu-NH₂) |
| E | (structure: NAM-tripeptide-phosphate) |

TABLE 2-continued
NAM Derivatives
| Compound # | Structure |
|---|---|
| F | 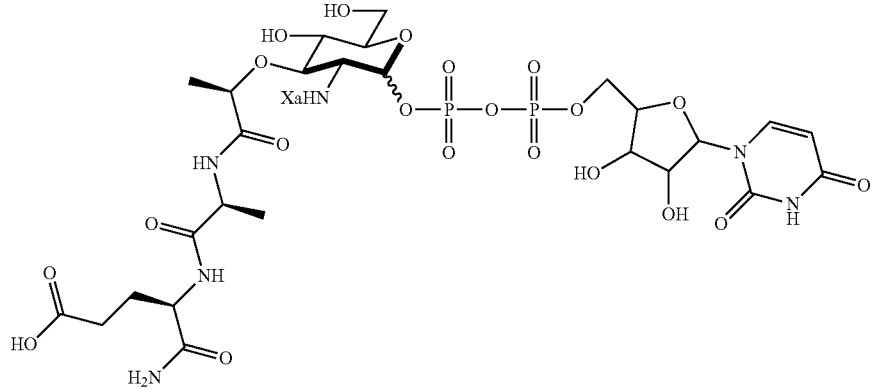 |
| G | 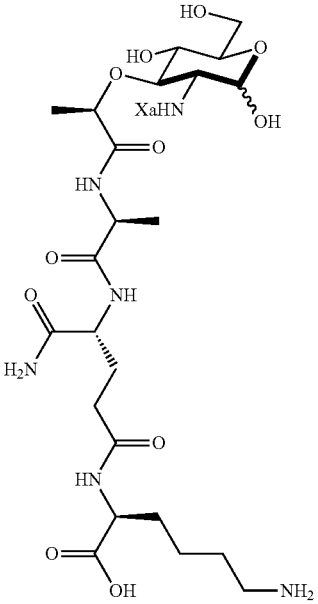 |

TABLE 2-continued
NAM Derivatives
| Compound # | Structure |
|---|---|
| H | 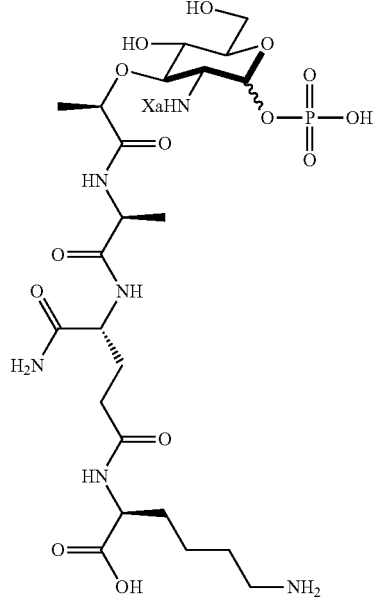 |
| J | 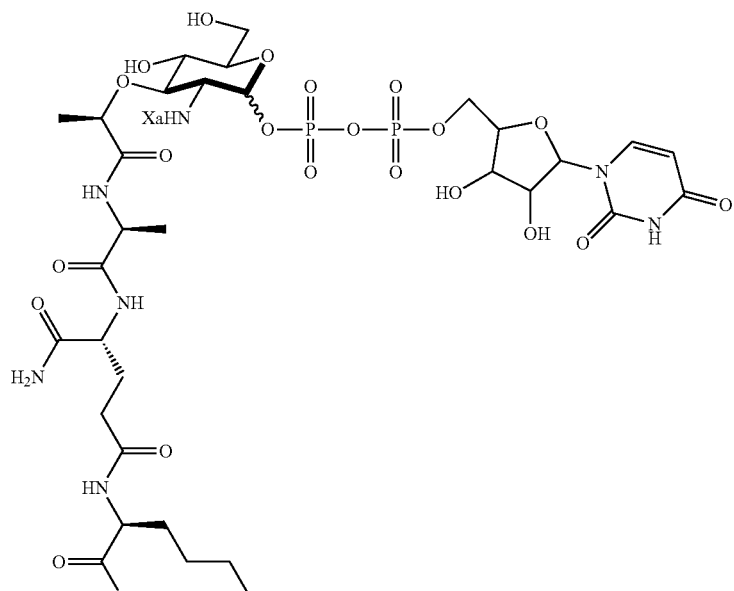 |

TABLE 2-continued
NAM Derivatives
| Compound # | Structure |
|---|---|
| K | 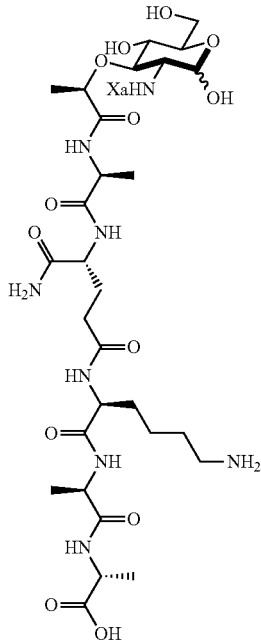 |
| L | 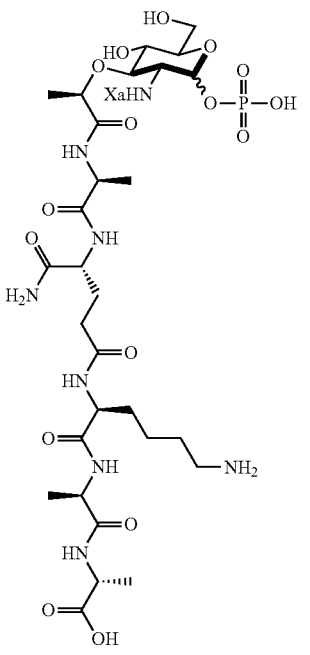 |

TABLE 2-continued
NAM Derivatives
| Compound # | Structure |
|---|---|
| M | 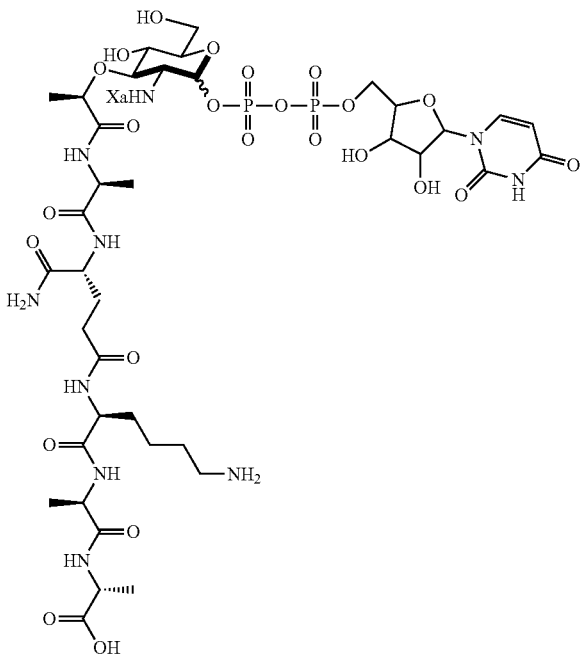 |
| N | 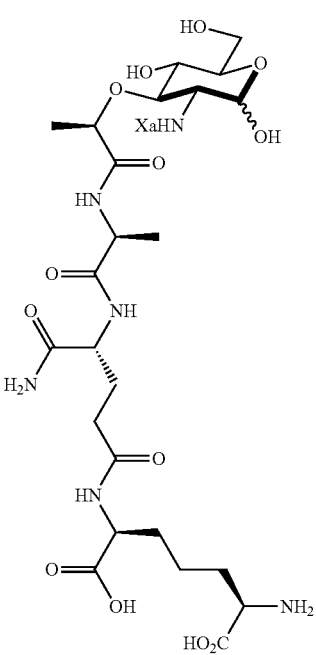 |

TABLE 2-continued

NAM Derivatives

| Compound # | Structure |
|---|---|
| O | (chemical structure) |
| P | (chemical structure) |

TABLE 2-continued
NAM Derivatives
| Compound # | Structure |
|---|---|
| Q | 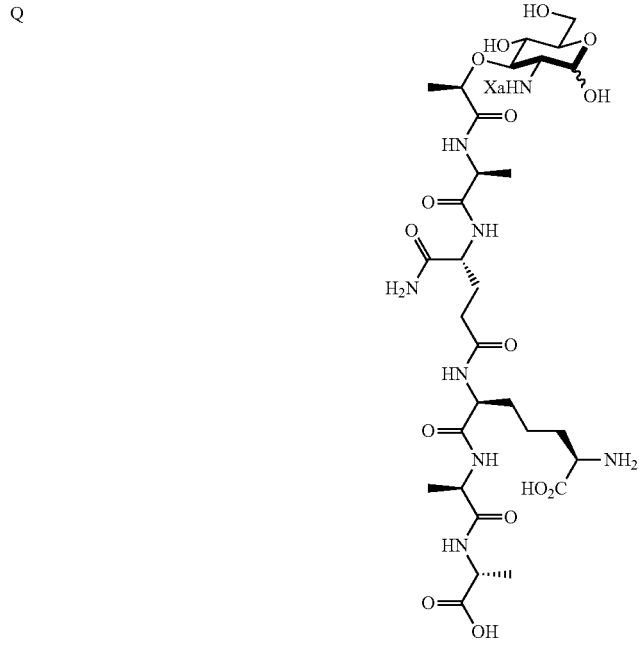 |
| R | 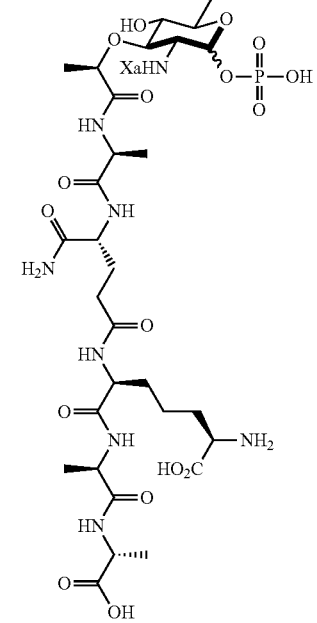 |

TABLE 2-continued
NAM Derivatives
| Compound # | Structure |
|---|---|
| S | 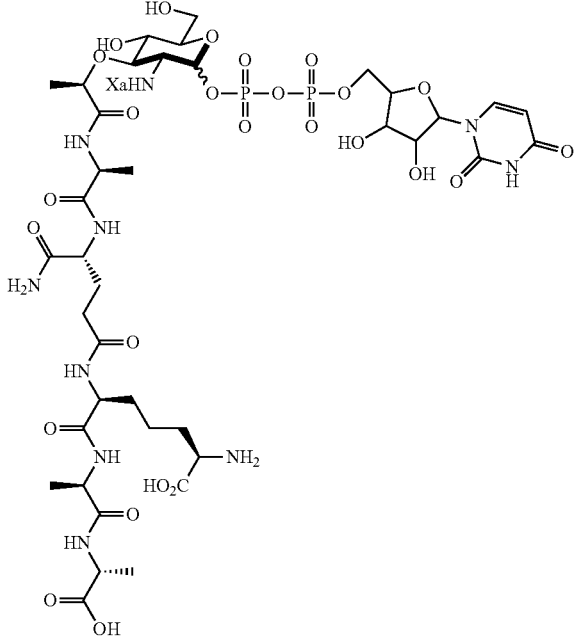 |
| T | 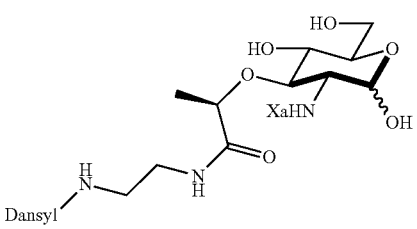 |
| U | 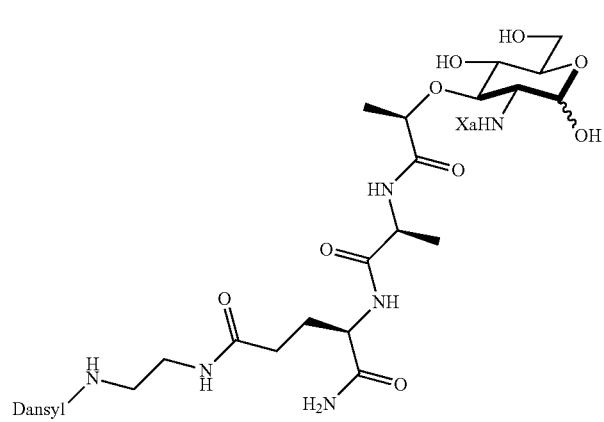 |
| V | 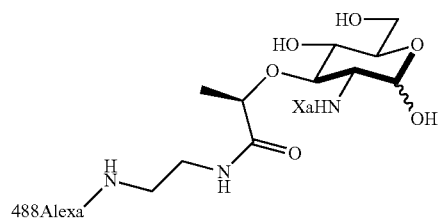 |

TABLE 2-continued
NAM Derivatives
| Compound # | Structure |
|---|---|
| W | 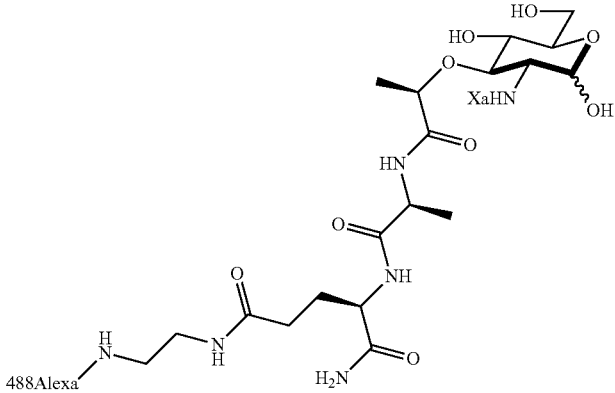 |
| X | 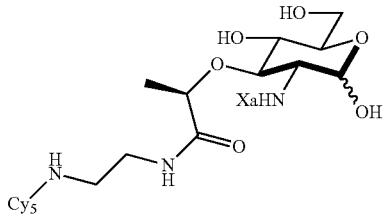 |
| Y | 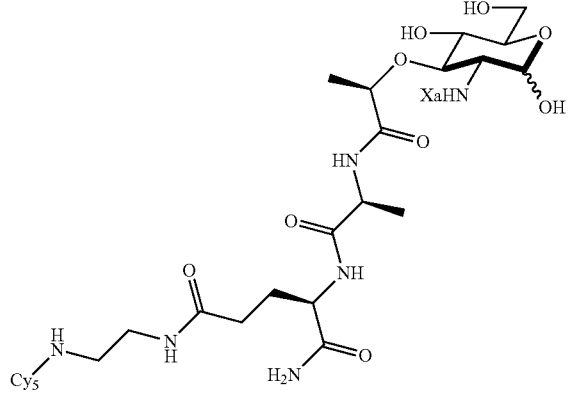 |
| Z | 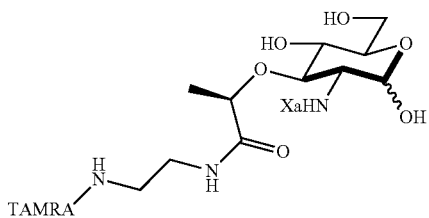 |

TABLE 2-continued

NAM Derivatives

| Compound # | Structure |
|---|---|
| AA | (structure: NAM sugar with XaHN, linked via lactyl-Ala-Gln(CONH2)-ethylenediamine-TAMRA) |
| AB | (structure: NAM sugar with XaHN, linked via lactyl-ethylenediamine-Fluorescein) |
| AC | (structure: NAM sugar with XaHN, linked via lactyl-Ala-Gln(CONH2)-ethylenediamine-Fluorescein) |
| AD | (structure: NAM sugar with XaHN, linked via lactyl-ethylenediamine-Rhodamine) |

TABLE 2-continued
NAM Derivatives
| Compound # | Structure |
|---|---|
| AE | 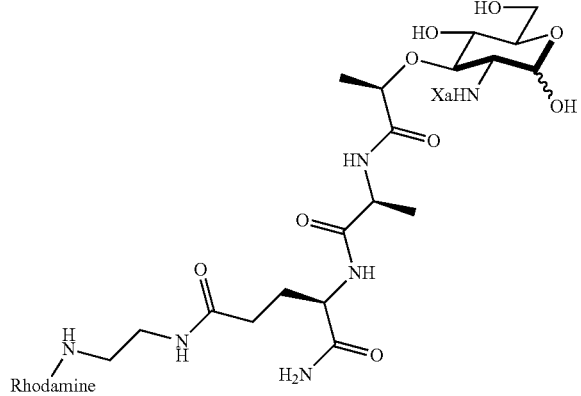 |
| AF | 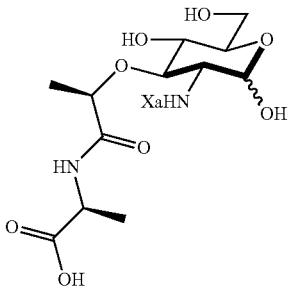 |
| AG | 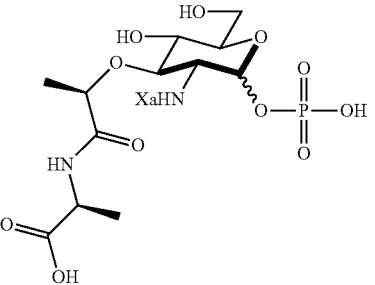 |
| AH | 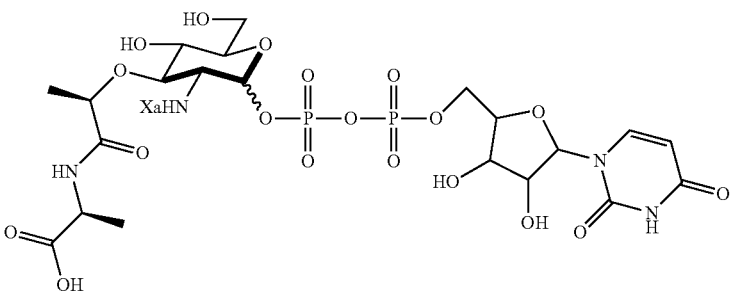 |

TABLE 2-continued

NAM Derivatives

| Compound # | Structure |
|---|---|
| AI | Muramic acid derivative with D-Ala-D-Ala-ethylenediamine-Dansyl |
| AJ | Muramic acid derivative with D-Ala-D-Ala-ethylenediamine-Alexa488 |
| AK | Muramic acid derivative with D-Ala-D-Ala-ethylenediamine-Cy5 |

TABLE 2-continued
NAM Derivatives
| Compound # | Structure |
|---|---|
| AL | 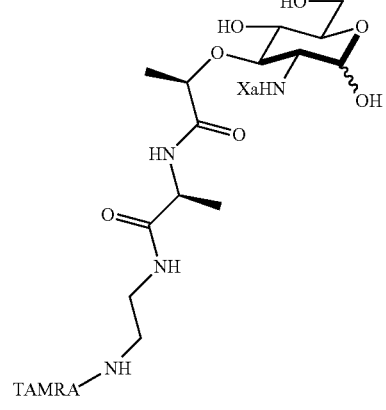 |
| AM | 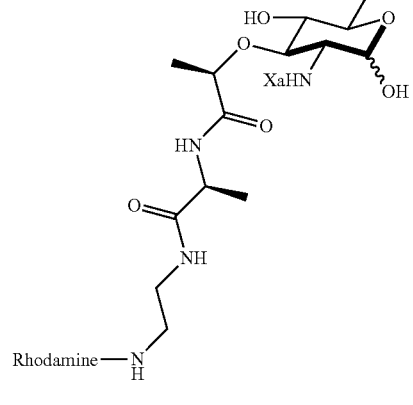 |
| AN | 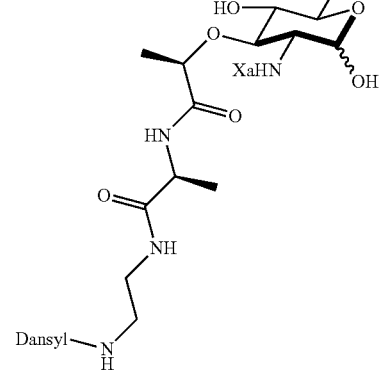 |

TABLE 2-continued
NAM Derivatives
| Compound # | Structure |
|---|---|
| AO | 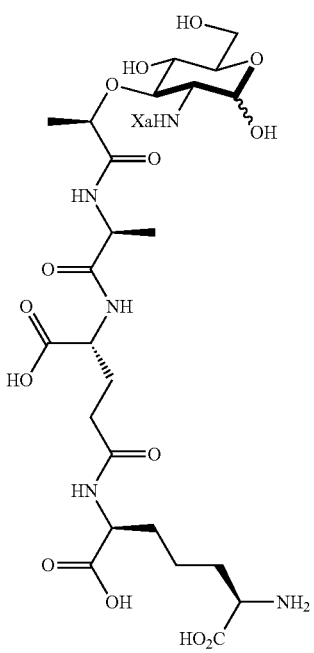 |
| AP | 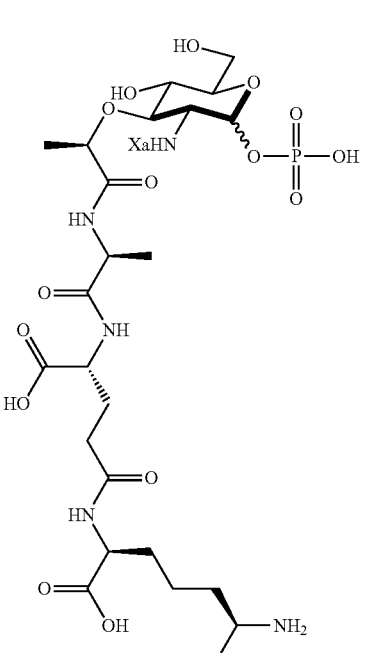 |

TABLE 2-continued
NAM Derivatives
| Compound # | Structure |
|---|---|
| AQ | 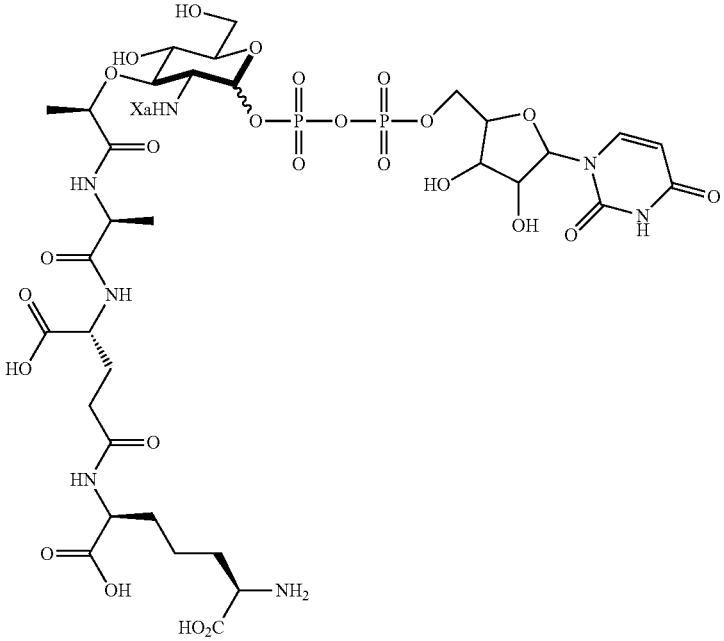 |
| AR | 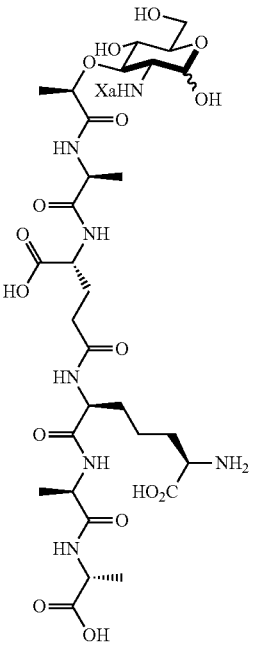 |

TABLE 2-continued
NAM Derivatives
| Compound # | Structure |
|---|---|
| AS | 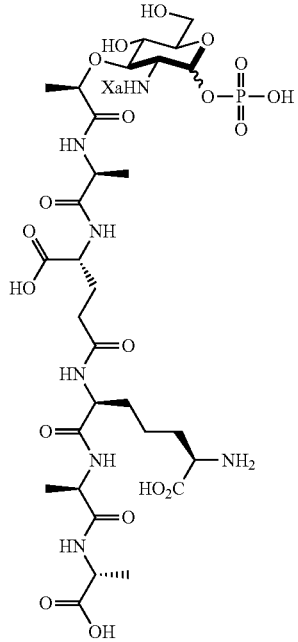 |
| AT | 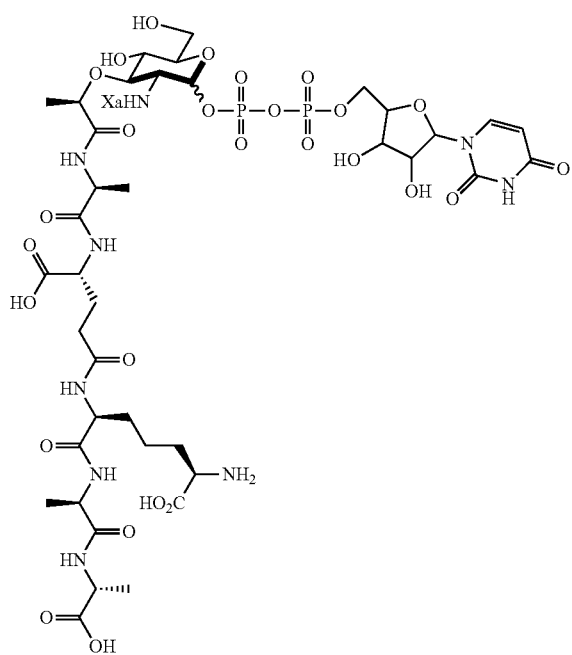 |

TABLE 2-continued

NAM Derivatives

| Compound # | Structure |
|---|---|
| AU | (structure shown) |
| AV | (structure shown) |
| AW | (structure shown) |

TABLE 2-continued

NAM Derivatives

| Compound # | Structure |
|---|---|
| AX | (structure: NAM derivative with Dansyl label) |
| AY | (structure: NAM derivative with 488Alexa label) |
| AZ | (structure: NAM derivative with Cy5 label) |

TABLE 2-continued

NAM Derivatives

| Compound # | Structure |
|---|---|
| BA | *(structure: NAM derivative with TAMRA label)* |
| BB | *(structure: NAM derivative with Rhodamine label)* |
| BC | *(structure: NAM derivative with Flourescein label)* |

TABLE 2-continued

NAM Derivatives

| Compound # | Structure |
|---|---|
| BD | (structure) |

TABLE 3

Generation of Peptidoglycan Derivatives from 2-Amino-MDP (3)

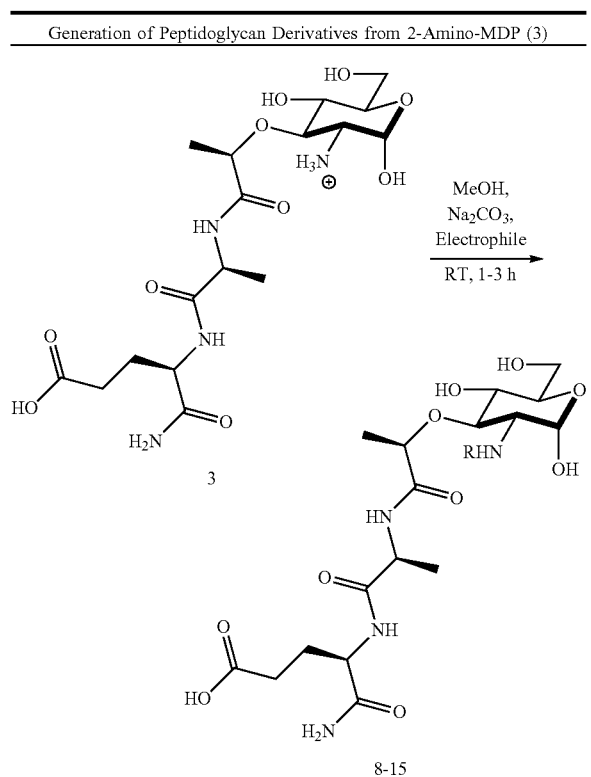

| Entry | Electrophile | Product | Yield |
|---|---|---|---|
| 1[a,b] | Acetoxyacetic acid NHS anhydride | D22, R = C(O)CH$_2$OAc | 48% |
| 3 | Ethyl triflouroacetate | D16, R = C(O)CF$_3$ | 92% |
| 4[c] | Succinic anhydride | D23, R = C(O)(CH$_2$)$_2$CO$_2$H | 66% |
| 5[d] | Levulinic acid NHS ester | D24, R = C(O)(CH$_2$)$_2$C(O)Me | 77% |
| 6[d] | 2-Azidoacetic acid NHS ester | D25, R = C(O)CH$_2$N$_3$ | 88% |
| 7[c,e] | Dansyl chloride | D29, R = Dansyl | 48% |
| 8 | Biotin NHS ester | D44, R = Biotin | 79% |

[a]Electrophile prepared according to literature precedent.

[b]Performed in H$_2$O with NaHCO$_3$.

[c]Stirred 24 h.

[d]Electrophile prepared with EDC/NHS.

[e]Performed in H$_2$O/DMF.

TABLE 4

Cellular Effects of Peptidoglycan Derivatives on Nod2 Signaling and Stability

| compound | NF-KB Fold Activation ± SD | Half-life (h) ± SD |
|---|---|---|
| Control | No activation | 7.1 ± 1.4 |
| D2 | 1.8 ± 0.3 | 15.9 ± 4.1 * |
| D9 | 3.1 ± 0.3 | 23.1 ± 2.2 * |
| D1 | No activation | 7.7 ± 0.7 |
| D22 | 2.2 ± 0.3 | Not tested |
| D53 | 2.6 ± 0.4 | 10.5 ± 2.6 * |

TABLE 4-continued

Cellular Effects of Peptidoglycan Derivatives on Nod2 Signaling and Stability

| compound | NF-KB Fold Activation ± SD | Half-life (h) ± SD |
|---|---|---|
| D16 | 1.9 ± 0.3 | 15.0 ± 1.8 * |
| D23 | 2.3 ± 0.3 | Not tested |
| D24 | 2.4 ± 0.3 | 11.7 ± 2.7 * |
| D25 | 1.8 ± 0.3 | 8.9 ± 0.9 * |
| D29 | 2.5 ± 0.3 | Not tested |
| D44 | No activation | 8.0 ± 0.7 |
| 18 | 2.8 ± 0.1[19] | 19.0 ± 1.8 * |

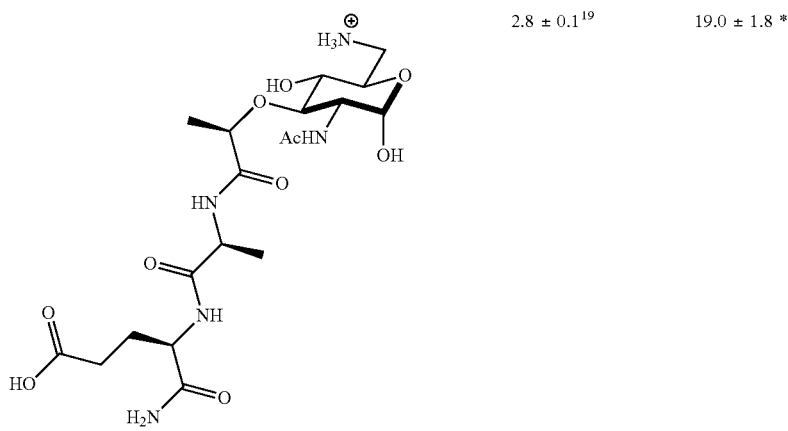

(+) Nod2 plasmid NF-κB activation normalized to the (−) Nod2 plasmid. Nod2 band intensities were plotted against time assuming first order decay (ln(I$_r$) vs. time). The rate constant was calculated using the negative slope of the line (k = −slope), and the corresponding half-life was calculated (T$_{1/2}$ = ln(2)/k)[35].
SD = Standard Deviation.
* = P < 0.05, stabilizes compared to the untreated control. The control, 3, and 16 did not significantly activate.

What is claimed:

1. An N-acetyl-muramic acid (NAM) derivative having formula I:

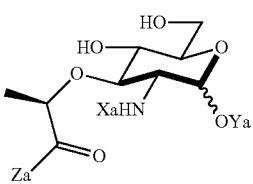

(I)

wherein Xa is selected from the group consisting of X22-X52 and X54-X59 as defined in table 1,
wherein Ya is selected from the group consisting of H, monophosphate, uridine diphosphate and ethyl azide linker prepared from 2-azido-ethanol, and
wherein Za is selected from the group consisting of OH, an ethylene diamine coupled fluorophore, a peptide and a peptide with an ethylene diamine coupled fluorophore, wherein the peptide is selected from the group consisting of a monopeptide, a dipeptide, a tripeptide and a pentapeptide.

2. The NAM derivative of claim 1, wherein Za is OH.

3. The NAM derivative of claim 1, wherein Xa is selected from the group consisting of X22, X24-X25, X28, X30-X35, X44-X52 and X54-X59 as defined in table 1.

4. The NAM derivative of claim 1, wherein Xa is selected from the group consisting of X25, X28, X30, X31, X45-X48 and X54-X55 as defined in table 1.

5. The NAM derivative of claim 1, wherein Za is a peptide, and wherein the NAM derivative is selected from the group consisting of compounds E, F, H, J, L, M, O, P, R, S, AG, AH, AP, AQ, AS, AT, AV, or AW as defined in table 2.

6. The NAM derivative of claim 3, wherein the NAM derivative is selected from the group consisting of compounds A, B, C, D, G, AH, AQ, AT, AW and BD as defined in table 2.

7. The NAM derivative of claim 1, wherein the NAM derivative is compound B or C as defined in table 2, and wherein the NAM derivative is synthesized in vitro in the presence of *P. putida* recycling enzymes AmgK and MurU.

8. The NAM derivative of claim 1, wherein Za is a peptide, and wherein the NAM derivative is synthesized in vitro from compound B or C as defined in table 2 in the presence of *E. coli* biosynthetic enzymes MurC, MurD, MurE, and MurF.

9. The NAM derivative of claim 1, wherein the NAM derivative is selected from the group consisting of compounds A, C, D and BD as defined in table 2.

10. A method for modulating nucleotide-binding oligomerization domain-containing protein 2 (Nod2) in a cell, comprising exposing the cell with an effective amount of the NAM derivative of claim 1.

11. The method of claim 10, further comprising stabilizing the Nod2 in the cell.

12. The method of claim 10, further comprising activating nuclear factor kappa-light-chain-enhancer of activated B cells (NF-κB) in the cell.

13. A method for modifying the cell wall of a bacterial cell, comprising (a) exposing the bacterial cell to an effective amount of the NAM derivative of claim 2,
(b) making a peptidoglycan from the NAM derivative from step (a) in the bacterial cell, and
(c) incorporating the peptidoglycan from step (b) into the cell wall of the bacterial cell, whereby the modified cell wall of the bacterial cell is obtained.

14. The method of claim 13, wherein Xa is selected from the group consisting of X22, X24-X25, X28, X30-X35, X44-X52 and X54-X59 as defined in table 1.

15. The method of claim 13, wherein Xa is selected from the group consisting of X25, X28, X30, X31, X45-X48, X54 and X55 as defined in table 1.

* * * * *